US010590440B2

(12) United States Patent
Jendresen et al.

(10) Patent No.: US 10,590,440 B2
(45) Date of Patent: *Mar. 17, 2020

(54) PROCESS FOR PRODUCING A FERMENTATION PRODUCT FROM A LIGNOCELLULOSE-CONTAINING MATERIAL

(71) Applicant: CysBio ApS, Kgs. Lyngby (DK)

(72) Inventors: Christian Bille Jendresen, Copenhagen (DK); Alex Toftgaard Nielsen, Rungsted Kyst (DK)

(73) Assignee: CysBio ApS, Kgs. Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/502,328

(22) PCT Filed: Aug. 21, 2015

(86) PCT No.: PCT/EP2015/069299
§ 371 (c)(1),
(2) Date: Feb. 7, 2017

(87) PCT Pub. No.: WO2016/026977
PCT Pub. Date: Feb. 25, 2016

(65) Prior Publication Data
US 2017/0183693 A1    Jun. 29, 2017

(30) Foreign Application Priority Data

Aug. 22, 2014 (EP) .................................... 14182040

(51) Int. Cl.
| | |
|---|---|
| *C12P 7/14* | (2006.01) |
| *C12P 5/00* | (2006.01) |
| *C12N 9/10* | (2006.01) |
| *C12P 7/10* | (2006.01) |
| *C12N 15/81* | (2006.01) |
| *C12N 15/52* | (2006.01) |

(52) U.S. Cl.
CPC ............... *C12P 7/14* (2013.01); *C12N 9/13* (2013.01); *C12N 15/52* (2013.01); *C12N 15/81* (2013.01); *C12P 5/005* (2013.01); *C12P 7/10* (2013.01); *C12Y 207/01025* (2013.01); *C12Y 207/07004* (2013.01); *C12Y 208/02001* (2013.01); *C12Y 301/03004* (2013.01); *C12P 2201/00* (2013.01); *C12P 2203/00* (2013.01); *Y02E 50/16* (2013.01)

(58) Field of Classification Search
CPC ........... C12P 7/14; C12P 7/10; C12P 2203/00; C12P 2201/00; C12Y 208/02001; C12Y 207/01025; C12Y 301/03004; C12Y 207/07004; C12N 15/81; C12N 15/52
See application file for complete search history.

(56) References Cited

U.S. PATENT DOCUMENTS

| | | |
|---|---|---|
| 8,546,106 B2 | 10/2013 | Merino |
| 2002/0164730 A1 | 11/2002 | Ballesteros Perdices et al. |
| 2007/0077630 A1 | 4/2007 | Harris et al. |
| 2011/0296543 A1* | 12/2011 | Chang ............ C12Y 302/01004 800/13 |
| 2012/0108855 A1* | 5/2012 | Ingram .................... C12N 1/22 568/840 |
| 2017/0226543 A1* | 8/2017 | Jendresen ............... C12P 11/00 |

FOREIGN PATENT DOCUMENTS

| | | |
|---|---|---|
| EP | 0 562 003 B1 | 9/2002 |
| WO | WO 98/03636 A1 | 1/1998 |
| WO | WO 02/095014 A2 | 11/2002 |
| WO | WO 2005/074647 A2 | 8/2005 |
| WO | WO 2005/074656 A2 | 8/2005 |
| WO | WO 2006/110891 A2 | 10/2006 |
| WO | WO 2006/110899 A2 | 10/2006 |
| WO | WO 2006/110900 A2 | 10/2006 |
| WO | WO 2006/110901 A2 | 10/2006 |
| WO | WO 2008/057637 A2 | 5/2008 |
| WO | WO 2008/076738 A2 | 6/2008 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Malojcic et al., Structural and mechanistic insights int PAPS-independent sulfotransfer catalyzed by bacterial aryl sulfotransferase and the role of DsbL/DsbI system in folding. Biochemistry, 2014, vol. 53: 1870-1877. (Year: 2014).*
Miller et al., Furfural inhibits growth by limiting sulfur assimilation in ethanologenic *Escherichia coli* strain LY180. Appl. Environ. Microbiol., 2009, vol. 25(19): 6132-6141. (Year: 2009).*
Parawira et al., Biotechnological strategies to overcome inhibitors in lignocellulose hydrolysates for ethanol production: review. Crit. Rev. Biotechnol., 2011, vol. 31(1): 20-31. (Year: 2011).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*

(Continued)

*Primary Examiner* — Ganapathirama Raghu
(74) *Attorney, Agent, or Firm* — Knobbe Martens Olson & Bear LLP

(57) ABSTRACT

The present invention relates to the production of hydrolyzates from a lignocellulose-containing material, and to fermentation of the hydrolyzates. More specifically, the present invention relates to the detoxification of phenolic inhibitors and toxins formed during the processing of lignocellulose-containing material by enzymatically sulfating the phenolic inhibitors and toxins using aryl sulfotransferases.

15 Claims, 9 Drawing Sheets

Specification includes a Sequence Listing.

(56) References Cited

OTHER PUBLICATIONS

Guo et al., Protein tolerance to random amino acid change. PNAS., 2004, vol. 101 (25): 9205-9210. (Year: 2004).*

Ghose, T.K. "International Union of Pure and Applied Chemistry—Applied Chemistry Division Commission on Biotechnology—Measurement of Cellulase Activities" Pure & Appl. Chem., 1987, pp. 257-268, vol. 59, No. 2.

Ghosh, Purnendu et al., "Physicochemical and Biological Treatments for Enzymatic/Microbial Conversion of Lignocellulosic Biomass" Advances in Applied Microbiology, 1993, pp. 295-333, vol. 39.

Gong, C.S. et al., "Ethanol Production from Renewable Resources" Advances in Biochemical Engineering / Biotechnology, 1999, pp. 207-241, vol. 65.

Guo, Xiang et al., "Comparison of methods for detoxification of spruce hydrolysate for bacterial cellulose production" Microbial Cell Factories, 2013, pp. 1-14, vol. 12, No. 93.

Hsu, Teh-An "Pretreatment of Biomass" Handbook on Bioethanol Production and Utilization, 1996, pp. 179-212, Chapter 10.

Li, Hao et al., "The Isolation and Characterization of cDNA Encoding the Mouse Bifunctional ATP Sulfurylase-Adenosine 5'-Phosphosulfate Kinase" The Journal of Biological Chemistry, Dec. 8, 1995, pp. 29453-29459, vol. 270, No. 49.

Logan, Helen M. et al., "Cloning of a cDNA Encoded by a Member of the Arabidopsis thaliana ATP Sulfurylase Multigene Family" The Journal of Biological Chemistry, May 24, 1996, pp. 12227-12233, vol. 271, No. 21.

Luo, Caidian et al., "Identification of potential fermentation inhibitors in conversion of hybrid poplar hydrolyzate to ethanol" Biomass and Bioenergy, 2002, pp. 125-138, vol. 22.

McMillan, James D. et al., "Pretreatment of Lignocellulosic Biomass" Enzymatic Conversion of Biomass for Fuels Production, 1994, pp. 292-324.

Mosier, Nathan et al., "Features of promising technologies for pretreatment of lignocellulosic biomass" Bioresource Technology, 2005, pp. 673-686, vol. 96.

Olsson, Lisbeth et al., "Fermentation of lignocellulosic hydrolysates for ethanol production" Enzyme and Microbial Technology, 1996, pp. 312-331, vol. 18.

Schell, Daniel J. et al., "Dilute—Sulfuric Acid Pretreatment of Corn Stover in Pilot-Scale Reactor" Applied Biochemistry and Biotechnology, 2003, pp. 69-85, vol. 105-108.

Vallander, L. et al., "Production of Ethanol from Lignocellulosic Materials: State of the Art" Advances in Biochemical Engineering / Biotechnology, 1990, pp. 63-95, vol. 42.

Venturi, Leandra Lórice et al., "Extracellular β-D-glucosidase from Chaetomium thermophilum var. coprophilum: production, purification and some biochemical properties" J. Basic Microbiol., 2002, pp. 55-66, vol. 42, No. 1.

Yanagisawa, Ken et al., "cDNA Cloning, Expression, and Characterization of the Human Bifunctional ATP Sulfurylase/ Adenosine 5'-Phosphosulfate Kinase Enzyme" Biosci. Biotechnol. Biochem., 1998, pp. 1037-1040, vol. 62, No. 5.

U.S. Appl. No. 60/832,511, filed Jul. 21, 2006, titled: Methods of Increasing Secretion of Beta-Glucosidases.

U.S. Appl. No. 60/941,251, filed May 31, 2007, titled: Compositions for Degrading Cellulosic Material.

International Search Report for PCT/EP2015/069299 dated Oct. 20, 2015.

* cited by examiner

SEQUENCE LISTING

```
<160> NUMBER OF SEQ ID NOS: 48

<210> SEQ ID NO 1
<211> LENGTH: 291
<212> TYPE: PRT
<213> ORGANISM: Rattus norvegicus

<400> SEQUENCE: 1

Met Glu Phe Ser Arg Pro Pro Leu Val His Val Lys Gly Ile Pro Leu
1               5                   10                  15

Ile Lys Tyr Phe Ala Glu Thr Ile Gly Pro Leu Gln Asn Phe Thr Ala
            20                  25                  30

Trp Pro Asp Asp Leu Leu Ile Ser Thr Tyr Pro Lys Ser Gly Thr Thr
        35                  40                  45

Trp Met Ser Glu Ile Leu Asp Met Ile Tyr Gln Gly Gly Lys Leu Glu
    50                  55                  60

Lys Cys Gly Arg Ala Pro Ile Tyr Ala Arg Val Pro Phe Leu Glu Phe
65                  70                  75                  80

Lys Cys Pro Gly Val Pro Ser Gly Leu Glu Thr Leu Glu Glu Thr Pro
                85                  90                  95

Ala Pro Arg Leu Leu Lys Thr His Leu Pro Leu Ser Leu Leu Pro Gln
            100                 105                 110

Ser Leu Leu Asp Gln Lys Val Lys Val Ile Tyr Ile Ala Arg Asn Ala
        115                 120                 125

Lys Asp Val Val Val Ser Tyr Tyr Asn Phe Tyr Asn Met Ala Lys Leu
130                 135                 140

His Pro Asp Pro Gly Thr Trp Asp Ser Phe Leu Glu Asn Phe Met Asp
145                 150                 155                 160

Gly Glu Val Ser Tyr Gly Ser Trp Tyr Gln His Val Lys Glu Trp Trp
                165                 170                 175

Glu Leu Arg His Thr His Pro Val Leu Tyr Leu Phe Tyr Glu Asp Ile
            180                 185                 190

Lys Glu Asn Pro Lys Arg Glu Ile Lys Lys Ile Leu Glu Phe Leu Gly
        195                 200                 205

Arg Ser Leu Pro Glu Glu Thr Val Asp Ser Ile Val His His Thr Ser
    210                 215                 220

Phe Lys Lys Met Lys Glu Asn Cys Met Thr Asn Tyr Thr Thr Ile Pro
225                 230                 235                 240

Thr Glu Ile Met Asp His Asn Val Ser Pro Phe Met Arg Lys Gly Thr
                245                 250                 255

Thr Gly Asp Trp Lys Asn Thr Phe Thr Val Ala Gln Asn Glu Arg Phe
            260                 265                 270

Asp Ala His Tyr Ala Lys Thr Met Thr Asp Cys Asp Phe Lys Phe Arg
        275                 280                 285

Cys Glu Leu
    290

<210> SEQ ID NO 2
<211> LENGTH: 295
<212> TYPE: PRT
<213> ORGANISM: Homo sapiens
```

<400> SEQUENCE: 2

```
Met Glu Leu Ile Gln Asp Thr Ser Arg Pro Leu Glu Tyr Val Lys
1               5                   10                  15

Gly Val Pro Leu Ile Lys Tyr Phe Ala Glu Ala Leu Gly Pro Leu Gln
            20                  25                  30

Ser Phe Gln Ala Arg Pro Asp Leu Leu Ile Ser Thr Tyr Pro Lys
        35                  40                  45

Ser Gly Thr Thr Trp Val Ser Gln Ile Leu Asp Met Ile Tyr Gln Gly
    50                  55                  60

Gly Asp Leu Glu Lys Cys His Arg Ala Pro Ile Phe Met Arg Val Pro
65                  70                  75                  80

Phe Leu Glu Phe Lys Ala Pro Gly Ile Pro Ser Gly Met Glu Thr Leu
                85                  90                  95

Lys Asp Thr Pro Ala Pro Arg Leu Leu Lys Thr His Leu Pro Leu Ala
            100                 105                 110

Leu Leu Pro Gln Thr Leu Leu Asp Gln Lys Val Lys Val Tyr Val
        115                 120                 125

Ala Arg Asn Ala Lys Asp Val Ala Val Ser Tyr Tyr His Phe Tyr His
    130                 135                 140

Met Ala Lys Val His Pro Glu Pro Gly Thr Trp Asp Ser Phe Leu Glu
145                 150                 155                 160

Lys Phe Met Val Gly Glu Val Ser Tyr Gly Ser Trp Tyr Gln His Val
                165                 170                 175

Gln Glu Trp Trp Glu Leu Ser Arg Thr His Pro Val Leu Tyr Leu Phe
            180                 185                 190

Tyr Glu Asp Met Lys Glu Asn Pro Lys Arg Glu Ile Gln Lys Ile Leu
        195                 200                 205

Glu Phe Val Gly Arg Ser Leu Pro Glu Glu Thr Val Asp Phe Met Val
    210                 215                 220

Gln His Thr Ser Phe Lys Glu Met Lys Lys Asn Pro Met Thr Asn Tyr
225                 230                 235                 240

Thr Thr Val Pro Gln Glu Phe Met Asp His Ser Ile Ser Pro Phe Met
                245                 250                 255

Arg Lys Gly Met Ala Gly Asp Trp Lys Thr Thr Phe Thr Val Ala Gln
            260                 265                 270

Asn Glu Arg Phe Asp Ala Asp Tyr Ala Glu Lys Met Ala Gly Cys Ser
        275                 280                 285

Leu Ser Phe Arg Ser Glu Leu
    290                 295
```

<210> SEQ ID NO 3
<211> LENGTH: 295
<212> TYPE: PRT
<213> ORGANISM: Equus caballus

<400> SEQUENCE: 3

```
Met Glu Leu Ile Gln Asp Thr Ser Arg Pro Leu Lys Tyr Val Lys
1               5                   10                  15

Gly Val Pro Leu Ile Lys Tyr Phe Ala Glu Ala Leu Gly Pro Leu Gln
            20                  25                  30

Ser Phe Gln Ala Arg Pro Asp Leu Leu Ile Ser Thr Tyr Pro Lys
        35                  40                  45

Ser Gly Thr Thr Trp Val Ser Glu Ile Leu Asp Met Ile Tyr His Gly
    50                  55                  60
```

Gly Asp Leu Glu Lys Cys Arg Arg Ala Pro Ile Phe Ile Arg Val Pro
65                  70                  75                  80

Phe Leu Glu Phe Lys Ala Pro Glu Ile Pro Ser Gly Val Glu Val Leu
                85                  90                  95

Lys Asp Thr Pro Ala Pro Arg Leu Leu Lys Thr His Leu Pro Leu Ser
            100                 105                 110

Leu Leu Pro Gln Thr Leu Leu Asp Gln Lys Val Lys Val Val Tyr Leu
        115                 120                 125

Ala Arg Asn Ala Lys Asp Val Ala Val Ser Tyr Tyr His Phe Tyr Arg
    130                 135                 140

Met Ala Lys Val His Pro Asp Pro Gly Thr Trp Asp Ser Phe Leu Glu
145                 150                 155                 160

Lys Phe Met Ala Gly Glu Val Ser Tyr Gly Ser Trp Tyr Lys His Val
                165                 170                 175

Gln Glu Trp Trp Glu Leu Ser His Thr His Pro Val Leu Tyr Leu Phe
            180                 185                 190

Tyr Glu Asp Met Lys Glu Asn Pro Lys Lys Glu Ile Gln Lys Ile Leu
        195                 200                 205

Glu Phe Val Gly Arg Ser Leu Pro Glu Glu Thr Leu Asp Arg Ile Val
    210                 215                 220

Gln His Thr Ser Phe Lys Glu Met Lys Lys Asn Pro Met Ala Asn Tyr
225                 230                 235                 240

Ser Thr Ile Pro Cys Asp Ile Met Asp His Asn Ile Ser Ala Phe Met
                245                 250                 255

Arg Lys Gly Ile Ala Gly Asp Trp Lys Asn Thr Phe Thr Val Ala Gln
            260                 265                 270

Asn Glu His Phe Asp Thr Asp Tyr Ala Glu Lys Met Ala Gly Cys Lys
        275                 280                 285

Leu Ser Phe Arg Ser Glu Val
        290                 295

<210> SEQ ID NO 4
<211> LENGTH: 295
<212> TYPE: PRT
<213> ORGANISM: Sus scrofa

<400> SEQUENCE: 4

Met Glu Pro Val Gln Asp Thr Tyr Arg Pro Pro Leu Glu Tyr Val Lys
1               5                   10                  15

Gly Val Pro Leu Ile Lys Tyr Phe Ala Glu Ala Leu Gly Pro Leu Glu
            20                  25                  30

Ser Phe Gln Ala Trp Pro Asp Asp Val Leu Ile Ser Thr Tyr Pro Lys
        35                  40                  45

Ser Gly Thr Thr Trp Val Ser Glu Ile Leu Asp Leu Ile Tyr Gln Gly
    50                  55                  60

Gly Asp Leu Gln Lys Cys Gln Arg Ala Pro Ile Phe Val Arg Val Pro
65                  70                  75                  80

Phe Leu Glu Phe Lys Ile Pro Gly Cys Pro Thr Gly Phe Glu Leu Leu
                85                  90                  95

Lys Asp Thr Pro Ala Pro Arg Leu Leu Lys Thr His Leu Pro Leu Ala
            100                 105                 110

Leu Leu Pro Gln Thr Leu Leu Asp Gln Lys Val Lys Val Val Tyr Val
        115                 120                 125

Ala Arg Asn Ala Lys Asp Val Ala Val Ser Tyr Tyr His Phe Tyr Arg
    130                 135                 140

```
Met Ala Lys Val His Pro Asn Pro Gly Thr Trp Asp Ser Phe Leu Glu
145                 150                 155                 160

Asp Phe Met Ala Gly Glu Val Ser Tyr Gly Ser Trp Tyr Gln His Val
                165                 170                 175

Gln Glu Trp Trp Glu Leu Arg His Thr His Pro Val Leu Tyr Leu Phe
            180                 185                 190

Tyr Glu Asp Met Lys Glu Asn Pro Lys Arg Glu Ile Gln Lys Ile Leu
        195                 200                 205

Glu Phe Val Gly Arg Ser Leu Pro Glu Glu Thr Val Glu Asp Ile Val
    210                 215                 220

Gln His Thr Ser Phe Gln Glu Met Lys Asn Asn Ala Met Thr Asn Tyr
225                 230                 235                 240

Arg Thr Leu Pro Ser Asp Leu Leu Asp His Ser Ile Ser Ala Phe Met
                245                 250                 255

Arg Lys Gly Ile Thr Gly Asp Trp Lys Ser Thr Phe Thr Val Ala Gln
                260                 265                 270

Asn Glu Arg Phe Glu Ala Asp Tyr Ala Glu Lys Met Ala Gly Cys Asn
            275                 280                 285

Leu Arg Phe Arg Ser Glu Leu
            290                 295

<210> SEQ ID NO 5
<211> LENGTH: 295
<212> TYPE: PRT
<213> ORGANISM: Canis lupus

<400> SEQUENCE: 5

Met Glu Asp Ile Pro Asp Thr Ser Arg Pro Pro Leu Lys Tyr Val Lys
1               5                   10                  15

Gly Ile Pro Leu Ile Lys Tyr Phe Ala Glu Ala Leu Glu Ser Leu Gln
                20                  25                  30

Asp Phe Gln Ala Gln Pro Asp Asp Leu Leu Ile Ser Thr Tyr Pro Lys
            35                  40                  45

Ser Gly Thr Thr Trp Val Ser Glu Ile Leu Asp Met Ile Tyr Gln Asp
    50                  55                  60

Gly Asp Val Glu Lys Cys Arg Arg Ala Pro Val Phe Ile Arg Val Pro
65                  70                  75                  80

Phe Leu Glu Phe Lys Ala Pro Gly Ile Pro Thr Gly Leu Glu Val Leu
                85                  90                  95

Lys Asp Thr Pro Ala Pro Arg Leu Ile Lys Thr His Leu Pro Leu Ala
            100                 105                 110

Leu Leu Pro Gln Thr Leu Leu Asp Gln Lys Val Lys Val Val Tyr Val
        115                 120                 125

Ala Arg Asn Ala Lys Asp Val Ala Val Ser Tyr Tyr His Phe Tyr Arg
    130                 135                 140

Met Ala Lys Val His Pro Asp Pro Asp Thr Trp Asp Ser Phe Leu Glu
145                 150                 155                 160

Lys Phe Met Ala Gly Glu Val Ser Tyr Gly Ser Trp Tyr Gln His Val
                165                 170                 175

Gln Glu Trp Trp Glu Leu Ser His Thr His Pro Val Leu Tyr Leu Phe
            180                 185                 190

Tyr Glu Asp Met Lys Glu Asn Pro Lys Arg Glu Ile Gln Lys Ile Leu
        195                 200                 205

Lys Phe Val Gly Arg Ser Leu Pro Glu Glu Thr Val Asp Leu Ile Val
    210                 215                 220
```

```
Gln His Thr Ser Phe Lys Glu Met Lys Asn Asn Ser Met Ala Asn Tyr
225                 230                 235                 240

Thr Thr Leu Ser Pro Asp Ile Met Asp His Ser Ile Ser Ala Phe Met
            245                 250                 255

Arg Lys Gly Ile Ser Gly Asp Trp Lys Thr Thr Phe Thr Val Ala Gln
        260                 265                 270

Asn Glu Arg Phe Asp Ala Asp Tyr Ala Lys Lys Met Glu Gly Cys Gly
    275                 280                 285

Leu Ser Phe Arg Thr Gln Leu
    290                 295

<210> SEQ ID NO 6
<211> LENGTH: 294
<212> TYPE: PRT
<213> ORGANISM: Gallus gallus

<400> SEQUENCE: 6

Met Gly Asn Asp Glu Val Ile Arg Gln Asp Leu Gly Cys Leu Tyr Asp
1               5                   10                  15

Ile Pro Leu Tyr Lys Cys Phe Val Ala Gly Trp Pro Gln Val Glu Ala
            20                  25                  30

Phe Gln Ala Arg Pro Asp Asp Leu Leu Ile Ala Thr Tyr Pro Lys Ser
        35                  40                  45

Gly Thr Thr Trp Leu Ser Glu Ile Leu Asp Ala Ile Tyr His Asp Gly
    50                  55                  60

Asp Leu Glu Lys Cys Arg Arg Asp Ala Ile Tyr Asn Arg Val Pro Phe
65                  70                  75                  80

Leu Glu Met Lys Ala Pro Gly Ile Leu Ser Gly Val Glu Gln Leu Glu
                85                  90                  95

Lys Ile Pro Ser Pro Arg Leu Val Lys Thr His Leu Pro Val His Leu
            100                 105                 110

Leu Pro Ala Ser Phe Gln Glu Lys Asp Cys Lys Val Ile Tyr Met Ala
        115                 120                 125

Arg Asn Ala Lys Asp Val Val Ile Ser Tyr Tyr Tyr Phe Tyr Gln Met
130                 135                 140

Ala Lys Ile His Pro Asp Pro Gly Thr Leu Ser Glu Phe Leu Gln Ala
145                 150                 155                 160

Phe Met Asp Gly Lys Val Ala Tyr Gly Ser Trp Tyr Lys His Val Lys
                165                 170                 175

Gly Trp Trp Glu Lys Arg His Glu Lys Arg Leu Leu Tyr Leu Phe Tyr
            180                 185                 190

Glu Asp Met Lys Lys Asp Pro Arg Arg Glu Ile Gln Lys Ile Leu Gln
        195                 200                 205

Phe Leu Gly Lys Glu Val Ala Glu Glu Thr Val Ala Arg Ile Leu His
210                 215                 220

His Thr Ser Phe Gln Glu Met Lys Lys Asn Pro Ala Thr Asn Tyr Glu
225                 230                 235                 240

Thr Met Pro Thr Glu Leu Met Asp His Ser Leu Ser Pro Phe Met Arg
                245                 250                 255

Lys Gly Ile Ser Gly Asp Trp Ala Asn His Phe Thr Val Ala Gln Asn
            260                 265                 270

Glu Arg Phe Asp Gln His Tyr Gln Gln Gln Met Ala Gly Ser Asp Leu
        275                 280                 285

Cys Phe Gln Met Glu Ala
    290
```

<210> SEQ ID NO 7
<211> LENGTH: 307
<212> TYPE: PRT
<213> ORGANISM: Gallus gallus

<400> SEQUENCE: 7

Met Ala Leu Asp Lys Met Glu Asn Leu Ser Leu Glu Glu Asn Met Leu
1               5                   10                  15

Arg Ser Glu Met Gly Glu Val Gln Gly Ile Pro Val Thr Lys Pro Thr
            20                  25                  30

Cys Asp Ile Trp Asp Gln Val Trp Asn Phe Lys Ala Arg Pro Asp Asp
        35                  40                  45

Leu Leu Val Ala Thr Tyr Ala Lys Ala Gly Thr Thr Trp Thr Gln Glu
    50                  55                  60

Ile Val Asp Met Ile Gln Gln Asn Gly Asp Ile Glu Lys Cys Arg Arg
65                  70                  75                  80

Ala Ser Thr Tyr Lys Arg His Pro Phe Leu Glu Trp Tyr Ile Pro Asp
                85                  90                  95

Ser Ser Pro Leu Gly Tyr Ser Gly Leu Lys Leu Ala Glu Ala Met Pro
            100                 105                 110

Ser Pro Arg Thr Met Lys Thr His Leu Pro Val Gln Leu Val Pro Pro
        115                 120                 125

Ser Phe Trp Glu Gln Asn Cys Lys Ile Ile Tyr Val Ala Arg Asn Ala
    130                 135                 140

Lys Asp Asn Leu Val Ser Tyr Tyr His Phe His Arg Met Asn Lys Val
145                 150                 155                 160

Leu Pro Asp Pro Gly Thr Ile Glu Glu Phe Thr Glu Lys Phe Met Asn
                165                 170                 175

Gly Glu Val Leu Trp Gly Ser Trp Tyr Asp His Val Lys Gly Trp Trp
            180                 185                 190

Lys Ala Lys Asp Lys His Arg Ile Leu Tyr Leu Phe Tyr Glu Asp Met
        195                 200                 205

Lys Glu Asn Pro Lys Arg Glu Ile Gln Lys Ile Met Lys Phe Leu Glu
    210                 215                 220

Lys Asp Leu Asp Glu Glu Val Leu Asn Lys Ile Ile Tyr Asn Thr Ser
225                 230                 235                 240

Phe Glu Ile Met Lys Asp Asn Pro Met Thr Asn Tyr Thr Lys Asp Phe
                245                 250                 255

Val Gly Val Met Asp His Ser Val Ser Pro Phe Met Arg Lys Gly Ser
            260                 265                 270

Val Gly Asp Trp Lys Asn Tyr Phe Thr Val Ala Leu Asn Lys Lys Phe
        275                 280                 285

Asp Gln Asp Tyr Lys Lys Met Ala Asp Thr Ser Leu Val Phe Arg
    290                 295                 300

Met Glu Leu
305

<210> SEQ ID NO 8
<211> LENGTH: 301
<212> TYPE: PRT
<213> ORGANISM: Danio rerio

```
<400> SEQUENCE: 8

Met Asp Leu Pro Asp Ile Ser Ser Ile Lys Leu Pro Ser Arg Pro Lys
1               5                   10                  15

Ile Phe Glu Phe Glu Gly Ile Ser Met Ile Ser Tyr Phe Thr Asp Asn
            20                  25                  30

Trp Glu Lys Leu Lys Asn Phe Gln Ala Arg Pro Asp Asp Ile Leu Ile
        35                  40                  45

Ala Thr Tyr Pro Lys Ala Gly Thr Thr Trp Val Ser Tyr Ile Leu Asp
    50                  55                  60

Leu Leu Tyr Phe Gly Lys Val Glu Pro Asn Gly Gln Ser Ser Leu Pro
65              70                  75                  80

Ile Tyr Met Arg Val Pro Phe Leu Glu Ser Cys Phe Pro Gly Met Pro
                85                  90                  95

Ser Gly Thr Glu Leu Ala Asp Asn Leu Pro Asn Ser Pro Arg Leu Ile
            100                 105                 110

Lys Thr His Leu Pro Val Gln Leu Val Pro Lys Ser Phe Trp Gly Gln
        115                 120                 125

Asn Ser Lys Val Val Tyr Val Ala Arg Asn Ala Lys Asp Asn Val Val
    130                 135                 140

Ser Phe Phe His Phe Asp Arg Met Asn His Gly Gln Pro Glu Pro Gly
145             150                 155                 160

Asp Trp Asp Thr Phe Leu Gln Ala Phe Ile Lys Gly Glu Arg Val Phe
                165                 170                 175

Gly Ser Trp Phe Asp His Val Cys Gly Trp Trp Glu Lys Lys Lys Thr
            180                 185                 190

Tyr Pro Asn Leu His Tyr Met Phe Tyr Glu Asp Ile Ala Lys Asp Ile
        195                 200                 205

Asn Gly Glu Val Glu Ser Leu Cys Thr Phe Leu Lys Leu Ser Arg Ser
    210                 215                 220

Asp Glu Glu Lys Glu Lys Ile Ile Asn Gly Val Gln Phe Asp Ala Met
225             230                 235                 240

Lys Gln Asn Val Met Thr Asn Tyr Ser Thr Ile Pro Thr Met Asp Phe
                245                 250                 255

Thr Ile Ser Pro Phe Met Arg Lys Gly Lys Val Gly Asp Trp Lys Asn
            260                 265                 270

His Phe Thr Val Ala Gln Asn Glu Gln Phe Asp Glu Asp Tyr Lys Glu
        275                 280                 285

Lys Met Lys Asn Thr Thr Leu Asn Phe Arg Thr Lys Ile
        290                 295                 300

<210> SEQ ID NO 9
<211> LENGTH: 300
<212> TYPE: PRT
<213> ORGANISM: Danio rerio

<400> SEQUENCE: 9

Met Glu Ile Gln Gly Lys Ser Ser Thr Asp Leu Pro Asp Arg Pro Glu
1               5                   10                  15

Ile Phe Glu Phe Glu Gly Ile Ser Met Val Glu His Phe Thr Lys Asn
            20                  25                  30

Trp Glu Asn Val Lys Asn Phe Gln Ala Arg Pro Asp Asp Ile Leu Ile
        35                  40                  45

Ala Thr Tyr Pro Lys Ala Gly Thr Thr Trp Val Ser Asn Ile Leu Asp
    50                  55                  60
```

```
Leu Leu Tyr Phe Gly Lys Glu Asp Pro Lys Arg Gln Thr Thr Lys Pro
 65                  70                  75                  80

Ile Tyr Lys Arg Val Pro Phe Leu Glu Ser Cys Phe Pro Glu Met Gln
                 85                  90                  95

Ser Gly Thr Glu Leu Ala Asn Asn Leu Pro Thr Ser Pro Arg Leu Ile
            100                 105                 110

Lys Thr His Leu Pro Val Gln Leu Val Pro Gln Ser Phe Trp Glu Lys
        115                 120                 125

Asn Ser Arg Val Ala Tyr Val Ala Arg Asn Ala Lys Asp Asn Ala Val
    130                 135                 140

Ser Tyr Phe His Phe Asn Arg Met Asn Lys Ala Gln Pro Glu Pro Gly
145                 150                 155                 160

Asp Trp Asn Thr Phe Leu Glu Glu Phe Met Lys Gly Lys Met Val Phe
                165                 170                 175

Gly Ser Trp Phe Asp His Val Cys Gly Trp Trp Glu Lys Lys Lys Thr
            180                 185                 190

Tyr Pro Asn Leu His Tyr Met Leu Tyr Glu Asp Met Ala Lys Asp Ile
        195                 200                 205

Lys Gly Glu Val Glu Ser Leu Cys Thr Phe Leu Lys Leu Ser Arg Ser
    210                 215                 220

Asp Glu Glu Lys Glu Lys Ile Ile Asn Gly Ile Gln Phe Asp Ala Met
225                 230                 235                 240

Lys Gln Asn Lys Met Thr Asn Tyr Ser Thr Val Leu Val Met Asp Phe
                245                 250                 255

Thr Ile Ser Pro Phe Met Arg Lys Gly Lys Val Gly Asp Trp Lys Asn
            260                 265                 270

His Phe Thr Val Ala Gln Asn Glu Gln Phe Asn Glu Asp Tyr Lys Gln
        275                 280                 285

Lys Met Lys Asn Ser Thr Leu Lys Phe Pro Thr Glu
    290                 295                 300

<210> SEQ ID NO 10
<211> LENGTH: 338
<212> TYPE: PRT
<213> ORGANISM: Drosophila melanogaster

<400> SEQUENCE: 10

Met Pro Gln Ser Ser Phe Phe Ala Lys Ser Val Pro Phe Glu Gln Ile
 1               5                  10                  15

Asp Lys Leu Ala Ile Ser Gly Gly Tyr Ser Ser Ile Phe Ala Ser Ser
             20                  25                  30

Lys Pro Ser Val Pro Val Val Gly Asn Trp Glu Gln Arg Phe Cys Arg
         35                  40                  45

Leu Ala Asp Thr Phe Gln Pro Val Leu Asp Arg Val Tyr Asp Phe Glu
     50                  55                  60

Val Arg Asp Asp Val Trp Ile Val Thr Leu Pro Lys Cys Gly Thr
 65                  70                  75                  80

Thr Trp Met Gln Glu Leu Ala Trp Leu Val Ile Asn Glu Cys Asp Phe
                 85                  90                  95

Glu Thr Ala Lys Ser Val Asp Leu Thr His Arg Ser Pro Phe Leu Glu
            100                 105                 110

Phe Asn Gly Val Val Pro Asn Val Pro His Asp Thr Ile Ala Ala Ala
        115                 120                 125

Asn Ala Leu Pro Ser Pro Arg Leu Ile Lys Ser His Leu Pro Ala Trp
    130                 135                 140
```

Met Leu Pro Arg Gln Ile Trp Ser Lys Arg Pro Lys Ile Ile Tyr Val
145                 150                 155                 160

Tyr Arg Asn Pro Lys Asp Ala Ala Ile Ser Tyr Phe His His Trp Arg
                165                 170                 175

Gly Met Val Gly Tyr Gln Gly Thr Lys Ser Asp Phe Met His Ser Phe
            180                 185                 190

Ile Asp Gly Tyr Val Asn Phe Thr Pro Cys Trp Pro His Ile Leu Asp
        195                 200                 205

Phe Trp Gln Leu Arg His Glu Pro Asn Ile Phe Phe Thr Ser Tyr Glu
    210                 215                 220

Arg Met Lys Gly Gln Leu Gly Gln Val Ile Ser Glu Val Ala Gln Phe
225                 230                 235                 240

Leu Glu Arg Ser Val Ser Gln Glu Gln Met Gln Gln Met Gln Arg His
                245                 250                 255

Leu Ser Phe Glu Ser Met Arg Asp Asn Pro Ala Cys Asn His Val Lys
            260                 265                 270

Glu Phe Glu Ser Met Lys Ala Ala Ala Gly Arg Glu Val Glu Glu Phe
        275                 280                 285

Arg Phe Val Arg Arg Gly Val Val Gly Ser His Lys Asp Glu Leu Thr
    290                 295                 300

Ala Asp Ile Ile Arg Glu Phe Asp Leu Trp Ser Asp Ser Asn Leu Arg
305                 310                 315                 320

Asp Phe Lys Leu Asn Met Asp Asp Phe Ala Asn Tyr Ser Lys Phe Ala
                325                 330                 335

Ser Thr

<210> SEQ ID NO 11
<211> LENGTH: 313
<212> TYPE: PRT
<213> ORGANISM: Drosophila melanogaster

<400> SEQUENCE: 11

Met Asn Arg Val Gln Val Thr Pro Arg Ser Tyr Pro Thr Asn Leu Ile
1               5                   10                  15

Asp Lys Asp Trp Gly Asn Arg Lys Leu Phe Tyr Thr Lys Asp Ser Glu
                20                  25                  30

Asn Phe Leu Arg Leu Val His Asp Met Lys Leu Arg Asp Asp Asp Val
            35                  40                  45

Trp Ile Val Thr Leu Pro Lys Cys Gly Thr Thr Trp Met Gln Glu Leu
        50                  55                  60

Leu Trp Leu Leu Leu Asn Asn Cys Asp Phe Glu Gly Ala Leu Ala Lys
65                  70                  75                  80

Asp Gln Glu Leu Arg Thr Pro Phe Leu Glu Phe Gly Tyr Ser Val Phe
                85                  90                  95

His Asp Pro Asn Arg Ser Phe Gly Pro Ile Glu Asp Leu Lys Ser Pro
            100                 105                 110

Arg Leu Ile Lys Ser His Leu Ser Leu Ala Leu Leu Pro Ser Lys Leu
        115                 120                 125

Trp Glu Gly Lys Asn Lys Val Ile Tyr Val Ser Arg Asn Pro Leu Asp
    130                 135                 140

Ser Tyr Val Ser Arg Tyr Tyr His Gly Val Ser Phe Gly Phe Asn Tyr
145                 150                 155                 160

Gly Lys Ser Leu His Gln Tyr Phe Asp Glu Val Leu Ala Ser Asp Asp
                165                 170                 175

```
Phe Pro Thr Glu Phe Ile Glu His Ala His Glu Phe Tyr Gln Leu Arg
            180                 185                 190

Asn Glu Pro Trp Val Phe Tyr Thr Ser Phe Glu Met Met Lys Lys Asp
        195                 200                 205

Leu Arg Gly Val Ile Asn Asp Val Ser Arg Phe Leu Asn Lys Pro Ile
    210                 215                 220

Asn Asp Gln Gln Met Glu Lys Leu Leu Lys His Leu Ser Phe Ala Glu
225                 230                 235                 240

Met Lys Lys Asn Pro Thr Thr Asn His Leu Trp Glu Leu Ala Gln Val
                245                 250                 255

Gln His Glu Asn Ala Gly Lys Glu Met His Pro Phe Val Arg Arg Gly
            260                 265                 270

Asp Val Asn Gly Tyr Lys Asp Glu Leu Lys Pro Glu Gln Ile Glu Lys
        275                 280                 285

Ala Asn Val Arg Ile Gln Glu Val Leu Ala Lys Asn Gly Val Thr Leu
    290                 295                 300

Asp Glu Leu Leu Leu Leu Lys Asp Gln
305                 310

<210> SEQ ID NO 12
<211> LENGTH: 346
<212> TYPE: PRT
<213> ORGANISM: Drosophila melanogaster

<400> SEQUENCE: 12

Met Glu Asn Thr Pro Leu Lys Phe Pro His Glu Ile Arg Asp Val Glu
1               5                   10                  15

Glu Ser Thr Asn Ala Glu Leu Leu Asp His Phe His Gly Glu Arg Thr
            20                  25                  30

Gly Phe Val Gln Val Gly Ser Glu Gly Tyr Phe Pro His Lys Tyr
        35                  40                  45

Lys Asp Glu Ala Glu Arg Tyr Tyr Asn Phe Glu Ala Arg Pro Asp Asp
50                  55                  60

Val Trp Ile Ala Thr Val Pro Arg Ser Gly Thr Thr Trp Thr Gln Glu
65                  70                  75                  80

Leu Ile Trp Leu Val Ala Asn Gly Leu Asp Phe Glu His Ala Gln Glu
                85                  90                  95

Arg Pro Leu Thr Glu Arg Phe Pro Phe Phe Glu Phe Pro Leu Phe Val
            100                 105                 110

His Pro Lys Ile Lys Glu Glu Leu Gln Glu Glu Asn Arg Asp Ser Ala
        115                 120                 125

Glu Ala Leu Glu Phe Ile Glu Lys Ile Ala Arg Pro Gly Tyr Glu Ala
    130                 135                 140

Leu Ser Glu Ile Pro Arg Ser Gln Arg Arg Phe Ile Lys Thr His Phe
145                 150                 155                 160

Pro Phe Ser Leu Met Pro Pro Ser Val Leu Glu Lys Lys Cys Lys Val
                165                 170                 175

Ile Tyr Val Val Arg Asp Pro Lys Asp Val Ala Val Ser Tyr Tyr His
            180                 185                 190

Leu Asn Arg Leu Phe Arg Thr Gln Gly Tyr Val Gly Asp Phe Glu Arg
        195                 200                 205

Tyr Trp His Tyr Phe Gln Asn Gly Leu Asn Pro Trp Leu Pro Tyr Tyr
    210                 215                 220

Ser His Val Lys Glu Ala Arg Glu His Ala His Leu Ser Asn Val Leu
225                 230                 235                 240
```

Phe Leu Arg Tyr Glu Asp Met Leu Ala Asp Leu Pro Gly Ala Ile Asn
                245                 250                 255

Ser Ile Ala Ser Phe Leu Glu Cys Pro Pro Lys Pro Glu Asp Met Asp
            260                 265                 270

Arg Leu Leu Asp His Leu Ser Ile Arg Ser Phe Arg Glu Asn Lys Ser
        275                 280                 285

Val Asn Met His Glu Met Ala Ser Val Gly Val Leu Asn Lys Gly Glu
    290                 295                 300

Ala Gly Phe Val Arg Ser Gly Ala Lys Thr Ala Tyr Gln Pro Gln Gln
305                 310                 315                 320

Glu Phe Val Glu Asn Pro Lys Leu Leu Lys Ser Ala Asn Glu Trp Val
                325                 330                 335

Glu Gln Asn Ile Lys Ser Phe Lys Thr Ile
            340                 345

<210> SEQ ID NO 13
<211> LENGTH: 323
<212> TYPE: PRT
<213> ORGANISM: Arabidopsis thaliana

<400> SEQUENCE: 13

Met Glu Met Asn Leu Arg Ile Glu Asp Leu Asn Glu Gly Thr Lys Thr
1               5                   10                  15

Leu Ile Ser Ser Leu Pro Ser Asp Lys Asp Phe Thr Gly Lys Thr Ile
            20                  25                  30

Cys Lys Tyr Gln Gly Cys Trp Tyr Thr His Asn Val Leu Gln Ala Val
        35                  40                  45

Leu Asn Phe Gln Lys Ser Phe Lys Pro Gln Asp Thr Asp Ile Ile Val
    50                  55                  60

Ala Ser Phe Pro Lys Cys Gly Thr Thr Trp Leu Lys Ala Leu Thr Phe
65                  70                  75                  80

Ala Leu Leu His Arg Ser Lys Gln Pro Ser His Asp Asp His Pro
                85                  90                  95

Leu Leu Ser Asn Asn Pro His Val Leu Val Pro Tyr Phe Glu Ile Asp
            100                 105                 110

Leu Tyr Leu Arg Ser Glu Asn Pro Asp Leu Thr Lys Phe Ser Ser Ser
        115                 120                 125

Pro Arg Leu Phe Ser Thr His Val Pro Ser His Thr Leu Gln Glu Gly
    130                 135                 140

Leu Lys Gly Ser Thr Cys Lys Ile Val Tyr Ile Ser Arg Asn Val Lys
145                 150                 155                 160

Asp Thr Leu Val Ser Tyr Trp His Phe Phe Thr Lys Gln Thr Asp
                165                 170                 175

Glu Lys Ile Ile Ser Ser Phe Glu Asp Thr Phe Glu Met Phe Cys Arg
            180                 185                 190

Gly Val Ser Ile Phe Gly Pro Phe Trp Asp His Val Leu Ser Tyr Trp
        195                 200                 205

Arg Gly Ser Leu Glu Asp Pro Asn His Val Leu Phe Met Lys Phe Glu
    210                 215                 220

Glu Met Lys Ala Glu Pro Arg Asp Gln Ile Lys Lys Phe Ala Glu Phe
225                 230                 235                 240

Leu Gly Cys Pro Phe Thr Lys Glu Glu Glu Ser Gly Ser Val Asp
                245                 250                 255

Glu Ile Ile Asp Leu Cys Ser Leu Arg Asn Leu Ser Ser Leu Glu Ile
            260                 265                 270

-continued

Asn Lys Thr Gly Lys Leu Asn Ser Gly Arg Glu Asn Lys Met Phe Phe
            275                 280                 285

Arg Lys Gly Glu Val Gly Asp Trp Lys Asn Tyr Leu Thr Pro Glu Met
290                 295                 300

Glu Asn Lys Ile Asp Met Ile Ile Gln Glu Lys Leu Gln Asn Ser Gly
305                 310                 315                 320

Leu Lys Phe

<210> SEQ ID NO 14
<211> LENGTH: 14
<212> TYPE: PRT
<213> ORGANISM: Artificial Sequence
<220> FEATURE:
<223> OTHER INFORMATION: His-Tag

<400> SEQUENCE: 14

Met Ala His His His His His His Glu Asn Leu Tyr Phe Gln
1               5                   10

<210> SEQ ID NO 15
<211> LENGTH: 302
<212> TYPE: PRT
<213> ORGANISM: Escherichia coli

<400> SEQUENCE: 15

Met Asp Gln Ile Arg Leu Thr His Leu Arg Gln Leu Glu Ala Glu Ser
1               5                   10                  15

Ile His Ile Ile Arg Glu Val Ala Ala Glu Phe Ser Asn Pro Val Met
            20                  25                  30

Leu Tyr Ser Ile Gly Lys Asp Ser Ser Val Met Leu His Leu Ala Arg
        35                  40                  45

Lys Ala Phe Tyr Pro Gly Thr Leu Pro Phe Pro Leu Leu His Val Asp
50                  55                  60

Thr Gly Trp Lys Phe Arg Glu Met Tyr Glu Phe Arg Asp Arg Thr Ala
65                  70                  75                  80

Lys Ala Tyr Gly Cys Glu Leu Leu Val His Lys Asn Pro Glu Gly Val
                85                  90                  95

Ala Met Gly Ile Asn Pro Phe Val His Gly Ser Ala Lys His Thr Asp
            100                 105                 110

Ile Met Lys Thr Glu Gly Leu Lys Gln Ala Leu Asn Lys Tyr Gly Phe
        115                 120                 125

Asp Ala Ala Phe Gly Gly Ala Arg Arg Asp Glu Glu Lys Ser Arg Ala
130                 135                 140

Lys Glu Arg Ile Tyr Ser Phe Arg Asp Arg Phe His Arg Trp Asp Pro
145                 150                 155                 160

Lys Asn Gln Arg Pro Glu Leu Trp His Asn Tyr Asn Gly Gln Ile Asn
                165                 170                 175

Lys Gly Glu Ser Ile Arg Val Phe Pro Leu Ser Asn Trp Thr Glu Gln
            180                 185                 190

Asp Ile Trp Gln Tyr Ile Trp Leu Glu Asn Ile Asp Ile Val Pro Leu
        195                 200                 205

Tyr Leu Ala Ala Glu Arg Pro Val Leu Glu Arg Asp Gly Met Leu Met
210                 215                 220

Met Ile Asp Asp Asn Arg Ile Asp Leu Gln Pro Gly Glu Val Ile Lys
225                 230                 235                 240

Lys Arg Met Val Arg Phe Arg Thr Leu Gly Cys Trp Pro Leu Thr Gly
                245                 250                 255

```
Ala Val Glu Ser Asn Ala Gln Thr Leu Pro Glu Ile Ile Glu Met
            260                 265                 270

Leu Val Ser Thr Thr Ser Glu Arg Gln Gly Arg Val Ile Asp Arg Asp
    275                 280                 285

Gln Ala Gly Ser Met Glu Leu Lys Lys Arg Gln Gly Tyr Phe
290                 295                 300
```

<210> SEQ ID NO 16
<211> LENGTH: 475
<212> TYPE: PRT
<213> ORGANISM: Escherichia coli

<400> SEQUENCE: 16

```
Met Asn Thr Ala Leu Ala Gln Gln Ile Ala Asn Glu Gly Gly Val Glu
1               5                   10                  15

Ala Trp Met Ile Ala Gln Gln His Lys Ser Leu Leu Arg Phe Leu Thr
            20                  25                  30

Cys Gly Ser Val Asp Asp Gly Lys Ser Thr Leu Ile Gly Arg Leu Leu
        35                  40                  45

His Asp Thr Arg Gln Ile Tyr Glu Asp Gln Leu Ser Ser Leu His Asn
    50                  55                  60

Asp Ser Lys Arg His Gly Thr Gln Gly Glu Lys Leu Asp Leu Ala Leu
65                  70                  75                  80

Leu Val Asp Gly Leu Gln Ala Glu Arg Glu Gln Gly Ile Thr Ile Asp
                85                  90                  95

Val Ala Tyr Arg Tyr Phe Ser Thr Glu Lys Arg Lys Phe Ile Ile Ala
            100                 105                 110

Asp Thr Pro Gly His Glu Gln Tyr Thr Arg Asn Met Ala Thr Gly Ala
        115                 120                 125

Ser Thr Cys Glu Leu Ala Ile Leu Leu Ile Asp Ala Arg Lys Gly Val
    130                 135                 140

Leu Asp Gln Thr Arg Arg His Ser Phe Ile Ser Thr Leu Leu Gly Ile
145                 150                 155                 160

Lys His Leu Val Val Ala Ile Asn Lys Met Asp Leu Val Asp Tyr Ser
                165                 170                 175

Glu Glu Thr Phe Thr Arg Ile Arg Glu Asp Tyr Leu Thr Phe Ala Gly
            180                 185                 190

Gln Leu Pro Gly Asn Leu Asp Ile Arg Phe Val Pro Leu Ser Ala Leu
        195                 200                 205

Glu Gly Asp Asn Val Ala Ser Gln Ser Glu Ser Met Pro Trp Tyr Ser
    210                 215                 220

Gly Pro Thr Leu Leu Glu Val Leu Glu Thr Val Glu Ile Gln Arg Val
225                 230                 235                 240

Val Asp Ala Gln Pro Met Arg Phe Pro Val Gln Tyr Val Asn Arg Pro
                245                 250                 255

Asn Leu Asp Phe Arg Gly Tyr Ala Gly Thr Leu Ala Ser Gly Arg Val
            260                 265                 270

Glu Val Gly Gln Arg Val Lys Val Leu Pro Ser Gly Val Glu Ser Asn
        275                 280                 285

Val Ala Arg Ile Val Thr Phe Asp Gly Asp Arg Glu Glu Ala Phe Ala
    290                 295                 300

Gly Glu Ala Ile Thr Leu Val Leu Thr Asp Glu Ile Asp Ile Ser Arg
305                 310                 315                 320

Gly Asp Leu Leu Leu Ala Ala Asp Glu Ala Leu Pro Ala Val Gln Ser
                325                 330                 335
```

-continued

```
Ala Ser Val Asp Val Val Trp Met Ala Glu Gln Pro Leu Ser Pro Gly
            340                 345                 350

Gln Ser Tyr Asp Ile Lys Ile Ala Gly Lys Lys Thr Arg Ala Arg Val
        355                 360                 365

Asp Gly Ile Arg Tyr Gln Val Asp Ile Asn Asn Leu Thr Gln Arg Glu
    370                 375                 380

Val Glu Asn Leu Pro Leu Asn Gly Ile Gly Leu Val Asp Leu Thr Phe
385                 390                 395                 400

Asp Glu Pro Leu Val Leu Asp Arg Tyr Gln Gln Asn Pro Val Thr Gly
                405                 410                 415

Gly Leu Ile Phe Ile Asp Arg Leu Ser Asn Val Thr Val Gly Ala Gly
            420                 425                 430

Met Val His Glu Pro Val Ser Gln Ala Thr Ala Ala Pro Ser Glu Phe
        435                 440                 445

Ser Ala Phe Glu Leu Glu Leu Asn Ala Leu Val Arg Arg His Phe Pro
    450                 455                 460

His Trp Gly Ala Arg Asp Leu Leu Gly Asp Lys
465                 470                 475

<210> SEQ ID NO 17
<211> LENGTH: 201
<212> TYPE: PRT
<213> ORGANISM: Escherichia coli

<400> SEQUENCE: 17

Met Ala Leu His Asp Glu Asn Val Val Trp His Ser His Pro Val Thr
1               5                   10                  15

Val Gln Gln Arg Glu Leu His His Gly His Arg Gly Val Val Leu Trp
            20                  25                  30

Phe Thr Gly Leu Ser Gly Ser Gly Lys Ser Thr Val Ala Gly Ala Leu
        35                  40                  45

Glu Glu Ala Leu His Lys Leu Gly Val Ser Thr Tyr Leu Leu Asp Gly
    50                  55                  60

Asp Asn Val Arg His Gly Leu Cys Ser Asp Leu Gly Phe Ser Asp Ala
65                  70                  75                  80

Asp Arg Lys Glu Asn Ile Arg Arg Val Gly Glu Val Ala Asn Leu Met
                85                  90                  95

Val Glu Ala Gly Leu Val Val Leu Thr Ala Phe Ile Ser Pro His Arg
            100                 105                 110

Ala Glu Arg Gln Met Val Arg Glu Arg Val Gly Glu Gly Arg Phe Ile
        115                 120                 125

Glu Val Phe Val Asp Thr Pro Leu Ala Ile Cys Glu Ala Arg Asp Pro
    130                 135                 140

Lys Gly Leu Tyr Lys Lys Ala Arg Ala Gly Glu Leu Arg Asn Phe Thr
145                 150                 155                 160

Gly Ile Asp Ser Val Tyr Glu Ala Pro Glu Ser Ala Glu Ile His Leu
                165                 170                 175

Asn Gly Glu Gln Leu Val Thr Asn Leu Val Gln Gln Leu Leu Asp Leu
            180                 185                 190

Leu Arg Gln Asn Asp Ile Ile Arg Ser
        195                 200

<210> SEQ ID NO 18
<211> LENGTH: 246
<212> TYPE: PRT
<213> ORGANISM: Escherichia coli
```

<400> SEQUENCE: 18

```
Met Leu Asp Gln Val Cys Gln Leu Ala Arg Asn Ala Gly Asp Ala Ile
1               5                   10                  15
Met Gln Val Tyr Asp Gly Thr Lys Pro Met Asp Val Val Ser Lys Ala
            20                  25                  30
Asp Asn Ser Pro Val Thr Ala Ala Asp Ile Ala Ala His Thr Val Ile
        35                  40                  45
Met Asp Gly Leu Arg Thr Leu Thr Pro Asp Val Pro Val Leu Ser Glu
    50                  55                  60
Glu Asp Pro Pro Gly Trp Glu Val Arg Gln His Trp Gln Arg Tyr Trp
65                  70                  75                  80
Leu Val Asp Pro Leu Asp Gly Thr Lys Glu Phe Ile Lys Arg Asn Gly
                85                  90                  95
Glu Phe Thr Val Asn Ile Ala Leu Ile Asp His Gly Lys Pro Ile Leu
            100                 105                 110
Gly Val Val Tyr Ala Pro Val Met Asn Val Met Tyr Ser Ala Ala Glu
        115                 120                 125
Gly Lys Ala Trp Lys Glu Glu Cys Gly Val Arg Lys Gln Ile Gln Val
    130                 135                 140
Arg Asp Ala Arg Pro Pro Leu Val Val Ile Ser Arg Ser His Ala Asp
145                 150                 155                 160
Ala Glu Leu Lys Glu Tyr Leu Gln Gln Leu Gly Glu His Gln Thr Thr
                165                 170                 175
Ser Ile Gly Ser Ser Leu Lys Phe Cys Leu Val Ala Glu Gly Gln Ala
            180                 185                 190
Gln Leu Tyr Pro Arg Phe Gly Pro Thr Asn Ile Trp Asp Thr Ala Ala
        195                 200                 205
Gly His Ala Val Ala Ala Ala Gly Ala His Val His Asp Trp Gln
    210                 215                 220
Gly Lys Pro Leu Asp Tyr Thr Pro Arg Glu Ser Phe Leu Asn Pro Gly
225                 230                 235                 240
Phe Arg Val Ser Ile Tyr
                245
```

<210> SEQ ID NO 19
<211> LENGTH: 58
<212> TYPE: DNA
<213> ORGANISM: Artificial Sequence
<220> FEATURE:
<223> OTHER INFORMATION: Primer CBJP472

<400> SEQUENCE: 19
tagaaataat tttgtttaac tttaagaagg agatatacca tggagttctc ccgtccac    58

<210> SEQ ID NO 20
<211> LENGTH: 49
<212> TYPE: DNA
<213> ORGANISM: Artificial Sequence
<220> FEATURE:
<223> OTHER INFORMATION: Primer CBJP473

<400> SEQUENCE: 20
taagcattat gcggccgcaa gcttgtcata gttcacaacg aaacttgaa    49

<210> SEQ ID NO 21
<211> LENGTH: 62
<212> TYPE: DNA
<213> ORGANISM: Artificial Sequence -continued

```
<220> FEATURE:
<223> OTHER INFORMATION: Primer CBJP470

<400> SEQUENCE: 21
tagaaataat tttgtttaac tttaagaagg agatatacca tggaactgat tcaggatacc      60
ag                                                                    62

<210> SEQ ID NO 22
<211> LENGTH: 47
<212> TYPE: DNA
<213> ORGANISM: Artificial Sequence
<220> FEATURE:
<223> OTHER INFORMATION: Primer CBJP471

<400> SEQUENCE: 22
taagcattat gcggccgcaa gcttgttaca gttcgctacg aaagctc                   47

<210> SEQ ID NO 23
<211> LENGTH: 60
<212> TYPE: DNA
<213> ORGANISM: Artificial Sequence
<220> FEATURE:
<223> OTHER INFORMATION: Primer CBJP499

<400> SEQUENCE: 23
tagaaataat tttgtttaac tttaagaagg agatatacca tggagctgat ccaggacacc     60

<210> SEQ ID NO 24
<211> LENGTH: 45
<212> TYPE: DNA
<213> ORGANISM: Artificial Sequence
<220> FEATURE:
<223> OTHER INFORMATION: Primer CBJP500

<400> SEQUENCE: 24
taagcattat gcggccgcaa gcttgtcaca cctctgagcg gaagc                     45

<210> SEQ ID NO 25
<211> LENGTH: 57
<212> TYPE: DNA
<213> ORGANISM: Artificial Sequence
<220> FEATURE:
<223> OTHER INFORMATION: Primer CBJP505

<400> SEQUENCE: 25
tagaaataat tttgtttaac tttaagaagg agatatacca tggagccggt ccaggac        57

<210> SEQ ID NO 26
<211> LENGTH: 45
<212> TYPE: DNA
<213> ORGANISM: Artificial Sequence
<220> FEATURE:
<223> OTHER INFORMATION: Primer CBJP506

<400> SEQUENCE: 26
taagcattat gcggccgcaa gcttgtcaca gctcagagcg gaagc                     45

<210> SEQ ID NO 27
<211> LENGTH: 57
<212> TYPE: DNA
<213> ORGANISM: Artificial Sequence
<220> FEATURE:
<223> OTHER INFORMATION: Primer CBJP503
```

<400> SEQUENCE: 27
tagaaataat tttgtttaac tttaagaagg agatatacca tggaggacat tcccgac    57

<210> SEQ ID NO 28
<211> LENGTH: 45
<212> TYPE: DNA
<213> ORGANISM: Artificial Sequence
<220> FEATURE:
<223> OTHER INFORMATION: Primer CBJP504

<400> SEQUENCE: 28
taagcattat gcggccgcaa gcttgtcaca gctgtgtgcg gaagc    45

<210> SEQ ID NO 29
<211> LENGTH: 62
<212> TYPE: DNA
<213> ORGANISM: Artificial Sequence
<220> FEATURE:
<223> OTHER INFORMATION: Primer CBJP501

<400> SEQUENCE: 29
tagaaataat tttgtttaac tttaagaagg agatatacca tggggaatga tgaggtgatc    60
ag    62

<210> SEQ ID NO 30
<211> LENGTH: 54
<212> TYPE: DNA
<213> ORGANISM: Artificial Sequence
<220> FEATURE:
<223> OTHER INFORMATION: Primer CBJP502

<400> SEQUENCE: 30
taagcattat gcggccgcaa gcttgttact ctgtctattg caatttatta cagg    54

<210> SEQ ID NO 31
<211> LENGTH: 65
<212> TYPE: DNA
<213> ORGANISM: Artificial Sequence
<220> FEATURE:
<223> OTHER INFORMATION: Primer CBJP491

<400> SEQUENCE: 31
catcttagta tattagttaa gtataagaag gagatataca tatggatcaa atacgactta    60
ctcac    65

<210> SEQ ID NO 32
<211> LENGTH: 46
<212> TYPE: DNA
<213> ORGANISM: Artificial Sequence
<220> FEATURE:
<223> OTHER INFORMATION: Primer CBJP492

<400> SEQUENCE: 32
tggccggccg atatccaatt gatcaggatc tgataatatc gttctg    46

<210> SEQ ID NO 33
<211> LENGTH: 24
<212> TYPE: DNA
<213> ORGANISM: Artificial Sequence
<220> FEATURE:
<223> OTHER INFORMATION: Primer CBJP497

<400> SEQUENCE: 33
tcaggatctg ataatatcgt tctg    24

```
<210> SEQ ID NO 34
<211> LENGTH: 59
<212> TYPE: DNA
<213> ORGANISM: Artificial Sequence
<220> FEATURE:
<223> OTHER INFORMATION: Primer CBJP498

<400> SEQUENCE: 34
cagaacgata ttatcagatc ctgataagtt aacaccgctc acagagacga ggtggagaa      59

<210> SEQ ID NO 35
<211> LENGTH: 46
<212> TYPE: DNA
<213> ORGANISM: Artificial Sequence
<220> FEATURE:
<223> OTHER INFORMATION: Primer CBJP496

<400> SEQUENCE: 35
tggccggccg atatccaatt gattagtaaa tagacactct gaaccc                    46

<210> SEQ ID NO 36
<211> LENGTH: 33
<212> TYPE: DNA
<213> ORGANISM: Artificial Sequence
<220> FEATURE:
<223> OTHER INFORMATION: Primer CBJP633

<400> SEQUENCE: 36
agtgcaggua aaacaatgga gttctcccgt cca                                  33

<210> SEQ ID NO 37
<211> LENGTH: 30
<212> TYPE: DNA
<213> ORGANISM: Artificial Sequence
<220> FEATURE:
<223> OTHER INFORMATION: Primier CBJP634

<400> SEQUENCE: 37
cgtgcgautc atagttcaca acgaaacttg                                      30

<210> SEQ ID NO 38
<211> LENGTH: 34
<212> TYPE: DNA
<213> ORGANISM: Artificial Sequence
<220> FEATURE:
<223> OTHER INFORMATION: Primer CBJP635

<400> SEQUENCE: 38
atctgtcaua aaacaatgga attttcacgt ccgc                                 34

<210> SEQ ID NO 39
<211> LENGTH: 32
<212> TYPE: DNA
<213> ORGANISM: Artificial Sequence
<220> FEATURE:
<223> OTHER INFORMATION: Primer CBJP636

<400> SEQUENCE: 39
cacgcgautc acagttcaca acgaaatttg aa                                   32

<210> SEQ ID NO 40
<211> LENGTH: 25
<212> TYPE: DNA
<213> ORGANISM: Artificial Sequence
<220> FEATURE:
<223> OTHER INFORMATION: Primer PTEF1_fw
```

-continued

<400> SEQUENCE: 40
cacgcgaugc acacaccata gcttc                                        25

<210> SEQ ID NO 41
<211> LENGTH: 25
<212> TYPE: DNA
<213> ORGANISM: Artificial Sequence
<220> FEATURE:
<223> OTHER INFORMATION: Primer PTEF1_rv

<400> SEQUENCE: 41
cgtgcgaugg aagtaccttc aaaga                                        25

<210> SEQ ID NO 42
<211> LENGTH: 58
<212> TYPE: DNA
<213> ORGANISM: Artificial Sequence
<220> FEATURE:
<223> OTHER INFORMATION: Primer CBJP517

<400> SEQUENCE: 42
tagaaataat tttgtttaac tttaagaagg agatatacca tggccctgga taaaatgg    58

<210> SEQ ID NO 43
<211> LENGTH: 49
<212> TYPE: DNA
<213> ORGANISM: Artificial Sequence
<220> FEATURE:
<223> OTHER INFORMATION: Primer CBJP518

<400> SEQUENCE: 43
taagcattat gcggccgcaa gcttgtcaca attccatgcg aaaaactag               49

<210> SEQ ID NO 44
<211> LENGTH: 56
<212> TYPE: DNA
<213> ORGANISM: Artificial Sequence
<220> FEATURE:
<223> OTHER INFORMATION: Primer CBJP533

<400> SEQUENCE: 44
tagaaataat tttgtttaac tttaagaagg agatatacca tggaattttc acgtcc      56

<210> SEQ ID NO 45
<211> LENGTH: 47
<212> TYPE: DNA
<213> ORGANISM: Artificial Sequence
<220> FEATURE:
<223> OTHER INFORMATION: Primer CBJP534

<400> SEQUENCE: 45
taagcattat gcggccgcaa gcttgttaca gttcacaacg aaatttg                 47

<210> SEQ ID NO 46
<211> LENGTH: 511
<212> TYPE: PRT
<213> ORGANISM: Saccharomyces cerevisiae

<400> SEQUENCE: 46

Met Pro Ala Pro His Gly Gly Ile Leu Gln Asp Leu Ile Ala Arg Asp
1               5                   10                  15

Ala Leu Lys Lys Asn Glu Leu Leu Ser Glu Ala Gln Ser Ser Asp Ile
            20                  25                  30

```
Leu Val Trp Asn Leu Thr Pro Arg Gln Leu Cys Asp Ile Glu Leu Ile
             35                  40                  45

Leu Asn Gly Gly Phe Ser Pro Leu Thr Gly Phe Leu Asn Glu Asn Asp
 50                  55                  60

Tyr Ser Ser Val Val Thr Asp Ser Arg Leu Ala Asp Gly Thr Leu Trp
 65                  70                  75                  80

Thr Ile Pro Ile Thr Leu Asp Val Asp Glu Ala Phe Ala Asn Gln Ile
                 85                  90                  95

Lys Pro Asp Thr Arg Ile Ala Leu Phe Gln Asp Glu Ile Pro Ile
                100                 105                 110

Ala Ile Leu Thr Val Gln Asp Val Tyr Lys Pro Asn Lys Thr Ile Glu
            115                 120                 125

Ala Glu Lys Val Phe Arg Gly Asp Pro Glu His Pro Ala Ile Ser Tyr
        130                 135                 140

Leu Phe Asn Val Ala Gly Asp Tyr Tyr Val Gly Gly Ser Leu Glu Ala
145                 150                 155                 160

Ile Gln Leu Pro Gln His Tyr Asp Tyr Pro Gly Leu Arg Lys Thr Pro
                165                 170                 175

Ala Gln Leu Arg Leu Glu Phe Gln Ser Arg Gln Trp Asp Arg Val Val
            180                 185                 190

Ala Phe Gln Thr Arg Asn Pro Met His Arg Ala His Arg Glu Leu Thr
        195                 200                 205

Val Arg Ala Ala Arg Glu Ala Asn Ala Lys Val Leu Ile His Pro Val
210                 215                 220

Val Gly Leu Thr Lys Pro Gly Asp Ile Asp His His Thr Arg Val Arg
225                 230                 235                 240

Val Tyr Gln Glu Ile Ile Lys Arg Tyr Pro Asn Gly Ile Ala Phe Leu
                245                 250                 255

Ser Leu Leu Pro Leu Ala Met Arg Met Ser Gly Asp Arg Glu Ala Val
            260                 265                 270

Trp His Ala Ile Ile Arg Lys Asn Tyr Gly Ala Ser His Phe Ile Val
        275                 280                 285

Gly Arg Asp His Ala Gly Pro Gly Lys Asn Ser Lys Gly Val Asp Phe
290                 295                 300

Tyr Gly Pro Tyr Asp Ala Gln Glu Leu Val Glu Ser Tyr Lys His Glu
305                 310                 315                 320

Leu Asp Ile Glu Val Val Pro Phe Arg Met Val Thr Tyr Leu Pro Asp
                325                 330                 335

Glu Asp Arg Tyr Ala Pro Ile Asp Gln Ile Asp Thr Thr Lys Thr Arg
            340                 345                 350

Thr Leu Asn Ile Ser Gly Thr Glu Leu Arg Arg Arg Leu Arg Val Gly
        355                 360                 365

Gly Glu Ile Pro Glu Trp Phe Ser Tyr Pro Glu Val Val Lys Ile Leu
370                 375                 380

Arg Glu Ser Asn Pro Pro Arg Pro Lys Gln Gly Phe Ser Ile Val Leu
385                 390                 395                 400

Gly Asn Ser Leu Thr Val Ser Arg Glu Gln Leu Ser Ile Ala Leu Leu
                405                 410                 415

Ser Thr Phe Leu Gln Phe Gly Gly Arg Tyr Tyr Lys Ile Phe Glu
            420                 425                 430

His Asn Asn Lys Thr Glu Leu Leu Ser Leu Ile Gln Asp Phe Ile Gly
        435                 440                 445
```

Ser Gly Ser Gly Leu Ile Ile Pro Asn Gln Trp Glu Asp Lys Asp
    450                 455                 460

Ser Val Val Gly Lys Gln Asn Val Tyr Leu Leu Asp Thr Ser Ser
465                 470                 475                 480

Ala Asp Ile Gln Leu Glu Ser Ala Asp Glu Pro Ile Ser His Ile Val
                485                 490                 495

Gln Lys Val Val Leu Phe Leu Glu Asp Asn Gly Phe Val Phe
            500                 505                 510

<210> SEQ ID NO 47
<211> LENGTH: 202
<212> TYPE: PRT
<213> ORGANISM: Saccharomyces cerevisiae

<400> SEQUENCE: 47

Met Ala Thr Asn Ile Thr Trp His Pro Asn Leu Thr Tyr Asp Glu Arg
1               5                   10                  15

Lys Ala Leu Arg Lys Gln Asp Gly Cys Thr Ile Trp Leu Thr Gly Leu
            20                  25                  30

Ser Ala Ser Gly Lys Ser Thr Ile Ala Cys Ala Leu Glu Gln Leu Leu
        35                  40                  45

Leu Gln Lys Asn Leu Ser Ala Tyr Arg Leu Asp Gly Asp Asn Ile Arg
    50                  55                  60

Phe Gly Leu Asn Lys Asp Leu Gly Phe Ser Glu Lys Asp Arg Asn Glu
65                  70                  75                  80

Asn Ile Arg Arg Ile Ser Glu Val Ser Lys Leu Phe Ala Asp Ser Cys
                85                  90                  95

Ala Ile Ser Ile Thr Ser Phe Ile Ser Pro Tyr Arg Val Asp Arg Asp
            100                 105                 110

Arg Ala Arg Glu Leu His Lys Glu Ala Gly Leu Lys Phe Ile Glu Ile
        115                 120                 125

Phe Val Asp Val Pro Leu Glu Val Ala Glu Gln Arg Asp Pro Lys Gly
    130                 135                 140

Leu Tyr Lys Lys Ala Arg Glu Gly Val Ile Lys Glu Phe Thr Gly Ile
145                 150                 155                 160

Ser Ala Pro Tyr Glu Ala Pro Lys Ala Pro Glu Leu His Leu Arg Thr
                165                 170                 175

Asp Gln Lys Thr Val Glu Glu Cys Ala Thr Ile Ile Tyr Glu Tyr Leu
            180                 185                 190

Ile Ser Glu Lys Ile Ile Arg Lys His Leu
        195                 200

<210> SEQ ID NO 48
<211> LENGTH: 357
<212> TYPE: PRT
<213> ORGANISM: Saccharomyces cerevisiae

<400> SEQUENCE: 48

Met Ala Leu Glu Arg Glu Leu Leu Val Ala Thr Gln Ala Val Arg Lys
1               5                   10                  15

Ala Ser Leu Leu Thr Lys Arg Ile Gln Ser Glu Val Ile Ser His Lys
            20                  25                  30

Asp Ser Thr Thr Ile Thr Lys Asn Asp Asn Ser Pro Val Thr Thr Gly
        35                  40                  45

Asp Tyr Ala Ala Gln Thr Ile Ile Ile Asn Ala Ile Lys Ser Asn Phe
    50                  55                  60

-continued

```
Pro Asp Asp Lys Val Val Gly Glu Glu Ser Ser Ser Gly Leu Ser Asp
65              70                  75                  80
Ala Phe Val Ser Gly Ile Leu Asn Glu Ile Lys Ala Asn Asp Glu Val
                85                  90                  95
Tyr Asn Lys Asn Tyr Lys Lys Asp Asp Phe Leu Phe Thr Asn Asp Gln
            100                 105                 110
Phe Pro Leu Lys Ser Leu Glu Asp Val Arg Gln Ile Ile Asp Phe Gly
        115                 120                 125
Asn Tyr Glu Gly Gly Arg Lys Gly Arg Phe Trp Cys Leu Asp Pro Ile
    130                 135                 140
Asp Gly Thr Lys Gly Phe Leu Arg Gly Glu Gln Phe Ala Val Cys Leu
145                 150                 155                 160
Ala Leu Ile Val Asp Gly Val Val Gln Leu Gly Cys Ile Gly Cys Pro
                165                 170                 175
Asn Leu Val Leu Ser Ser Tyr Gly Ala Gln Asp Leu Lys Gly His Glu
            180                 185                 190
Ser Phe Gly Tyr Ile Phe Arg Ala Val Arg Gly Leu Gly Ala Phe Tyr
        195                 200                 205
Ser Pro Ser Ser Asp Ala Glu Ser Trp Thr Lys Ile His Val Arg His
    210                 215                 220
Leu Lys Asp Thr Lys Asp Met Ile Thr Leu Glu Gly Val Glu Lys Gly
225                 230                 235                 240
His Ser Ser His Asp Glu Gln Thr Ala Ile Lys Asn Lys Leu Asn Ile
                245                 250                 255
Ser Lys Ser Leu His Leu Asp Ser Gln Ala Lys Tyr Cys Leu Leu Ala
            260                 265                 270
Leu Gly Leu Ala Asp Val Tyr Leu Arg Leu Pro Ile Lys Leu Ser Tyr
        275                 280                 285
Gln Glu Lys Ile Trp Asp His Ala Ala Gly Asn Val Ile Val His Glu
    290                 295                 300
Ala Gly Gly Ile His Thr Asp Ala Met Glu Asp Val Pro Leu Asp Phe
305                 310                 315                 320
Gly Asn Gly Arg Thr Leu Ala Thr Lys Gly Val Ile Ala Ser Ser Gly
                325                 330                 335
Pro Arg Glu Leu His Asp Leu Val Val Ser Thr Ser Cys Asp Val Ile
            340                 345                 350
Gln Ser Arg Asn Ala
            355
```

PROCESS FOR PRODUCING A FERMENTATION PRODUCT FROM A LIGNOCELLULOSE-CONTAINING MATERIAL

CROSS REFERENCE TO RELATED APPLICATIONS

This application is a U.S. National Phase Application of PCT International Application Number PCT/EP2015/069299, filed on Aug. 21, 2015, designating the United States of America and published in the English language, which is an International Application of and claims the benefit of priority to European Patent Application No. 14182040.7, filed on Aug. 22, 2014. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-ZACCO44-013APC.txt, the date of creation of the ASCII text file is Feb. 2, 2017, and the size of the ASCII text file is 60 KB.

TECHNICAL FIELD OF THE INVENTION

The present invention relates to the production of hydrolyzates from a lignocellulose-containing material, and to fermentation of the hydrolyzates. More specifically, the present invention relates to the detoxification of phenolic inhibitors and toxins formed during the processing of lignocellulose-containing material by sulfating the phenolic inhibitors and toxins.

BACKGROUND OF THE INVENTION

It is desired to change energy management increasingly from fossil fuels to renewable energies. The European Union, for instance, has established the serious ambition to increase the proportion of renewable energies to at least 10% in the traffic sector until the year 2020 (Directive 2009/28/EC of the European Parliament and of the Council). One renewable energy source of increasing importance is biofuel. In contrast to electric energy obtained from renewable energy sources, biofuel is well storable and universally usable. Biogas and biofuel are obtained from the conversion of biomass.

At present, the majority of biomass used for the production of biofuel predominantly originates from edible and forage crops. The production of biofuel by using edible and forage crops is designated as biofuel production of the first generation. In temperate climate zones such as, e.g., in Europe and in the U.S.A., mostly corn, wheat, rye and sugar beets are used. In the tropical climate zone such as, e.g., in Brazil, mostly sugar cane is used. Therefore, the production of biofuel by production methods of the first generation directly competes with the production of foodstuff. In the past years, this led to perceptible price rises of foodstuff with severe consequences for the nutrition of the population of the Third World. Exemplarily, from 2010 to 2011, the wheat price increased by 44% and the corn price even increased by 66%. Further, the production of biofuel by using forage crops is comparably ineffective and large cultivated farming areas are typically used. Further, extensive fertilization and manuring of large areas is required. For these reasons, several methods have been developed to generate biofuel by using lignocellulosic biomass. Here, not only crops, but also inedible plants and trees are used. Furthermore, the waste residues of the crops and trees are used, such as straw, leaves and bark. The production of biofuel by using lignocellulosic biomass is also designated as biofuel production of the second generation. The biofuel production of the second generation has the advantage that it is not in direct competition with food production and fertilizers are often abdicable. A large spectrum of biomass resources can be used, as overall biomass averagely comprises approximately 70% lignocellulose. Therefore, in principle, the production of biofuel by using lignocellulosic biomass is a promising approach to overcome many of the above-referenced problems.

However, the efficient production of fermentation products such as biofuel by using lignocellulosic biomass is still hampered by the poor conversion of lignocellulose into sugars, and by the generation of inhibitory phenolic compounds during the pre-processing and hydrolysis of the biomass. These compounds are inhibitory to the microorganisms that are used for producing biofuels and biochemicals from the biomass hydrolyzate.

SUMMARY OF THE INVENTION

The object of the present invention is to decrease the concentration of inhibitory phenolic compounds that are present in the biomass hydrolysate. The invention also focuses on improving the tolerance of the production organisms towards inhibitory phenolic compounds. This is done by modifying inhibitory compounds such as phenolic lignin derivatives formed during the processing of the biomass such to make them less toxic for the production organisms.

The present invention thus provides in a first aspect a process for producing a hydrolyzed product from a lignocellulose-containing material, comprising the steps of:
(a) pre-treating a lignocellulose-containing material;
(b) hydrolyzing the pre-treated lignocellulose-containing material to form a hydrolyzate; and
(c) enzymatically sulfating phenolic compounds produced during step a) and/or step b).

The present invention provides in a further aspect a process for the production of a fermentation product, from a lignocellulose-containing material, comprising the steps:
(a) pre-treating a lignocellulose-containing material;
(b) hydrolyzing the pre-treated lignocellulose-containing material to form a hydrolyzate;
(c) enzymatically sulfating phenolic compounds produced during step a) and/or step b).
(d) fermenting the hydrolyzate obtained in step (b) using a fermenting organism, thereby obtaining a fermentation product.

DETAILED DESCRIPTION OF THE INVENTION

Figure 1:
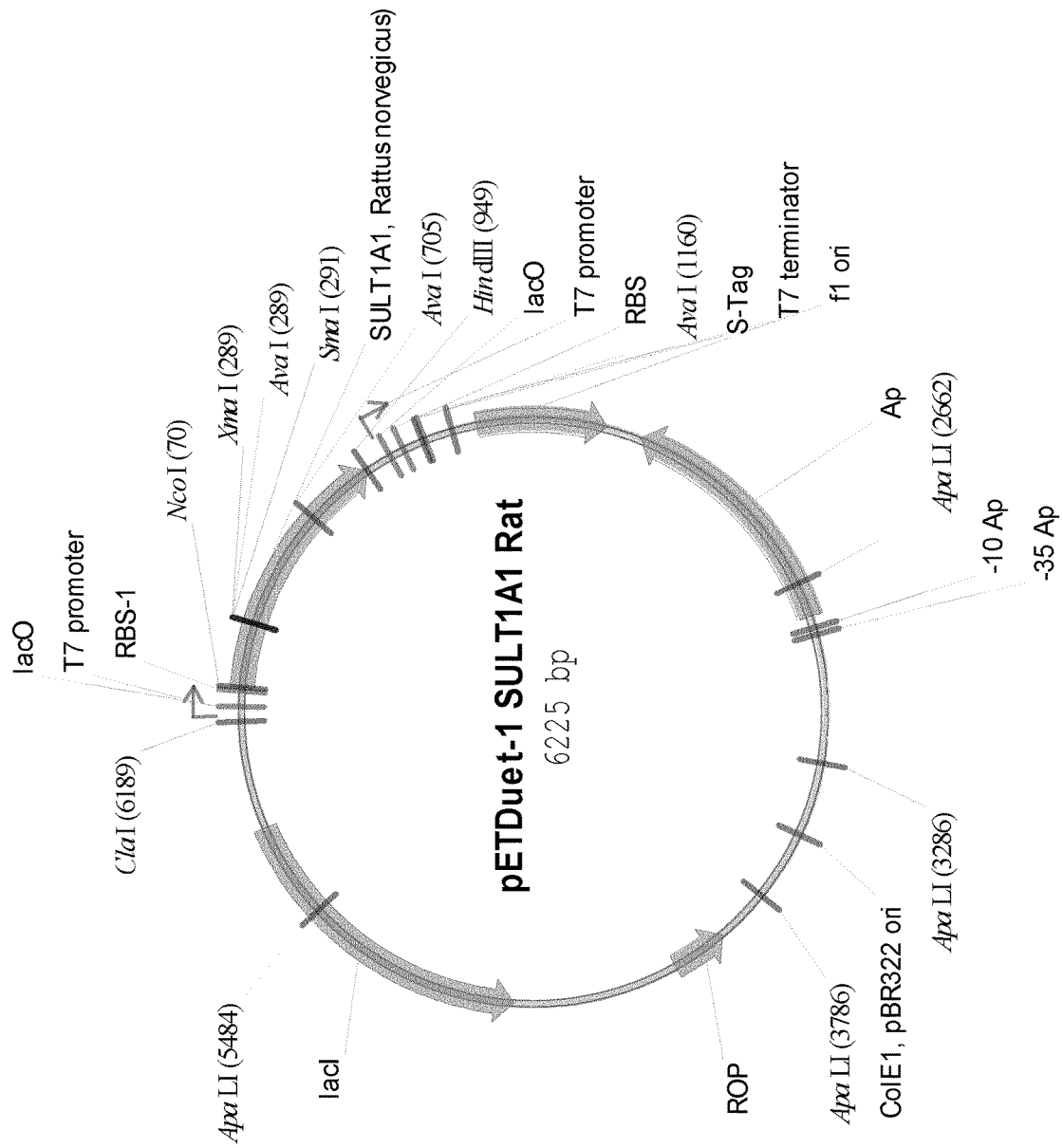
FIG. 1: Map of plasmid for expression of SULT1A1 from *Rattus norvegicus* in *Escherichia coli*

Lignocellulose is a mass of insoluble organic material. Typically, lignocellulose is composed of approximately 40-50% cellulose, approximately 20-30% hemicellulose and 20-30% lignin. Cellulose is a linear polymer composed of glucose polymerized by an alpha-1,4 glycosidic linkage. It typically forms microcrystalline structures which can only be poorly dissolved and hydrolyzed. Hemicellulose is a heteropolysaccharide that is composed of different hexoses, pentoses and glucuronic acid. The hemicellulose xylane is often found in grass and wood. Lignin is an insoluble polymer of aromatic alcohols known as monolignols, such as coniferyl alcohol, sinapyl alcohol and paracoumaryl alcohol. The cellulose microfibrils are conjugated with another by hemicellulose and/or lignin by covalent and non-covalent bonds. These bonds, in particular the covalent bonds, are highly stable and nearly inert against chemical and biological hydrolysis.

Lignocellulose is poorly accessible for most of the cellulose degrading enzymes. Therefore, a pretreatment of lignocellulose is an important step to obtain higher yields of sugars that can be further converted into downstream products.

However, during the pretreatment, undesirable fermentation inhibiting agents are generated. Further, lignin cannot be recovered by most of the methods employed in the art. The pretreatment of lignocellulose is typically the most expensive and laborious step of the production of bioethanol and the costs for said pretreatment step sums up to approximately 20-30% of the total costs of bioethanol. However, in comparison with bioethanol production with no pretreatment, the pretreatment of lignocellulose-containing biomass can still reduce the costs per liter bioethanol approximately 6-fold due to higher yields.

In general, the pretreatment can be enabled by physical, chemical and physicochemical means. Physical pretreatment may be, e.g., grinding, crushing, irradiation (e.g., gamma irradiation, cathode ray or microwave irradiation) and/or explosion (e.g., steam explosion, $CO_2$ explosion or $SO_2$ explosion). Chemical pretreatment may be, e.g., treatment with bases (basic hydrolysis) (e.g., sodium hydroxide solution and/or ammonia solution) or treatment with diluted acids (acidic hydrolysis) (e.g., sulfuric acid, hydrochloric acid, phosphoric acid and/or nitric acid). Physicochemical pretreatment may be, e.g., gas treatment (e.g., treatment with chlorine dioxide and/or sulfur dioxide), oxidation (e.g., hydrogen peroxide, active or oxygen or ozone treatment) and/or extraction of lignin (e.g., by a butyl alcohol solution and/or by an ethanol solution). Often, two or more of the aforementioned methods are also combined with another. Biomass subjected to grinding, crushing or the extraction of lignin is typically used for the production of biofuel, in particular ethanol. Biomass subjected to irradiation, explosion, any chemical treatment, gas treatment or oxidation is typically used for the production of biofuel. However, the pre-treatment methods described above, result in the generation of inhibitors that interfere with the further fermentation steps. These inhibitors typically have to be removed by costly and laborious means. Especially acidic and heat-based pretreatment often leads to the production of inhibitors of a following fermentation steps, which may severely hamper the production of biofuel or biochemical such as amino acids. These inhibitors are often weak acids (e.g., acetic acid, formic acid, ferulic acid), furan derivatives (e.g., furfural and 5-hydroxymethylfurfural) and/or lignin derivatives (phenolic compounds/phenol derivatives such as vanillin and 4-hydroxybenzaldehyde). It has been shown that many types of yeast are inhibited by phenol derivatives which may occur upon pretreatment with acids or steam. Therefore, it is an object of the present invention to convert the inhibitors to non-toxic compounds, or at least convert them to less toxic/inhibiting compounds.

Thus, the present invention provides in a first aspect a process for producing a hydrolyzed product from a lignocellulose-containing material, comprising the steps of:
(a) pre-treating a lignocellulose-containing material;
(b) hydrolyzing the pre-treated lignocellulose-containing material to form a hydrolyzate; and
(c) enzymatically sulfating phenolic compounds produced during step a) and/or step b).

The term "lignocellulose-containing material" used herein refers to material that comprises, or primarily consists of, cellulose, hemicellulose, and lignin. The term is synonymous with "lignocellulosic material". Such material is often referred to as "biomass".

The structure of lignocellulose is not directly accessible to hydrolysis, and in particular to enzymatic hydrolysis. Therefore, the lignocellulose-containing material has to be pre-treated, e.g., by acid hydrolysis under adequate conditions of pressure and temperature, in order to break the lignin seal and disrupt the crystalline structure of cellulose. This causes solubilization of the hemicellulose and cellulose fractions. The lignocellulose-containing material may be pre-treated in any suitable way. Pre-treatment may be carried out before and/or during hydrolysis and/or fermentation. According to certain embodiments, the pre-treated material is hydrolyzed, preferably enzymatically, before and/or during fermentation. The goal of pre-treatment is to separate and/or release cellulose; hemicellulose and/or lignin and this way improve the rate of hydrolysis. Pre-treatment methods such as wet-oxidation and alkaline pre-treatment targets lignin, while dilute acid and auto-hydrolysis targets hemicellulose. Steam explosion is an example of a pre-treatment that targets cellulose.

When lignocellulose-containing material is pre-treated, degradation products that may inhibit enzymes and/or may be toxic to fermenting organisms are produced. Many of the phenolic compounds are released from the degrading lignin. Examples of such phenolic compounds are 4-OH benzyl alcohol, 4-OH benzaldehyde, 4-OH benzoic acid, coumaric acid, ferulic acid, phenol, guaiacol, pyrogallol, pyrogallol mono methyl ether, vanillyl alcohol, vanillin, isovanillin, vanillic acid, isovanillic acid, homovanillic acid, gallic acid, 2-O-methyl gallic acid, syringyl alcohol, syringylaldehyde, syringic acid, homocatechol, ethyl vanillin, creosol, coniferyl aldehyde, isoeugenol, hydroquinone, eugenol or combinations thereof. Other inhibitory compounds can be found in, e.g., Luo et al., 2002, Biomass and Bioenergy 22: 125-138, which reference is hereby incorporated by reference.

According to the invention the pre-treatment applied in step (a) may be a conventional pre-treatment step using techniques well known in the art. Examples of suitable pre-treatments are disclosed above. In a preferred embodiment, pre-treatment takes place in aqueous slurry.

Any lignocellulose-containing material is contemplated according to the present invention. The lignocellulose-containing material may be any material containing lignocellulose. In a preferred embodiment the lignocellulose-containing material contains at least 30 wt. %, preferably at least 50 wt. %, more preferably at least 70 wt. %, even more preferably at least 90 wt. % lignocellulose. It is to be understood that the lignocellulose-containing material may also comprise other constituents such as proteinaceous material, starch, sugars, such as fermentable sugars and/or unfermentable sugars.

Lignocellulose-containing material is generally found, for example, in the stems, leaves, hulls, husks, and cobs of plants or leaves, branches, and wood of trees. Lignocellulose-containing material can also be, but is not limited to, herbaceous material, agricultural residues, forestry residues, municipal solid wastes, waste paper, and pulp and paper mill residues. It is understood herein that lignocellulose-containing material may be in the form of plant cell wall material containing lignin, cellulose, and hemi-cellulose in a mixed matrix.

According to certain embodiments, the lignocellulose-containing material comprises one or more of corn stover, corn fiber, rice straw, pine wood, wood chips, poplar, bagasse, paper and pulp processing waste.

Other examples of lignocellulose-containing material include hardwood, such as poplar and birch, softwood, cereal straw, such as wheat straw, switchgrass, municipal solid waste, industrial organic waste, office paper, or mixtures thereof.

The lignocellulose-containing material may according to the invention be chemically, mechanically and/or biologically pre-treated before hydrolysis and/or fermentation. Mechanical treatment (often referred to as physical treatment) may be used alone or in combination with subsequent or simultaneous hydrolysis, especially enzymatic hydrolysis.

Preferably, chemical, mechanical and/or biological pre-treatment is carried out prior to the hydrolysis and/or fermentation. Alternatively, the chemical, mechanical and/or biological pre-treatment may be carried out simultaneously with hydrolysis, such as simultaneously with addition of one or more cellulolytic enzymes, or other enzyme activities mentioned below, to release, e.g., fermentable sugars, such as glucose and/or maltose.

According to certain embodiments, the lignocellulose-containing material is pre-treated chemically. As used herein, the term "pre-treated chemically" or "chemical treatment" refers to any chemical pre-treatment which promotes the separation and/or release of cellulose, hemicellulose and/or lignin. Examples of suitable chemical pre-treatments include treatment with; for example, dilute acid, lime, alkaline, organic solvent, ammonia, sulfur dioxide, carbon dioxide. Further, wet oxidation and pH-controlled hydrothermolysis are also considered chemical pre-treatment. In a preferred embodiment the chemical pre-treatment is acid treatment, more preferably, a continuous dilute and/or mild acid treatment, such as, treatment with sulfuric acid, or another organic acid, such as acetic acid, citric acid, tartaric acid, succinic acid, hydrogen chloride or mixtures thereof. Other acids may also be used. Mild acid treatment means that the treatment pH lies in the range from about 1 to about 5, such as from about 1 to about 3. In a specific embodiment the acid concentration is in the range from about 0.1 to about 2.0 wt. % acid, preferably sulphuric acid. The acid may be contacted with the lignocellulose-containing material and the mixture may be held at a temperature in the range from about 160 to about 220° C., such as from about 165 to about 195° C., for periods ranging from minutes to seconds, e.g., from about 1 to about 60 minutes, such as from about 2 to about 30 minutes or about 3 to about 12 minutes. Addition of strong acids, such as sulphuric acid, may be applied to remove hemicellulose. This enhances the digestibility of cellulose.

Other techniques are also contemplated. Cellulose solvent treatment has been shown to convert about 90% of cellulose to glucose. It has also been shown that enzymatic hydrolysis could be greatly enhanced when the lignocellulose structure is disrupted. Alkaline $H_2O_2$, ozone, glycerol, dioxane, phenol, or ethylene glycol are among solvents known to disrupt cellulose structure and promote hydrolysis.

Alkaline chemical pre-treatment with base, e.g., NaOH, $Na_2CO_3$ and/or ammonia or the like, is also contemplated according to the invention. Pre-treatment methods using ammonia are described in, e.g., WO 2006/110891, WO 2006/110899, WO 2006/110900, and WO 2006/110901 (which are hereby incorporated by reference).

Wet oxidation techniques involve use of oxidizing agents, such as: sulphite based oxidizing agents or the like. Examples of solvent pre-treatments include treatment with DMSO (Dimethyl Sulfoxide) or the like. Chemical pre-treatment is generally carried out for 1 to 60 minutes, such as from 5 to 30 minutes, but may be carried out for shorter or longer periods of time dependent on the material to be pre-treated.

Other examples of suitable pre-treatment methods are described by Schell et al., 2003, Appl. Biochem and Biotechn. Vol. 105-108: 69-85, and Mosier et al., 2005, Bioresource Technology 96: 673-686, and U.S. Publication No. 2002/0164730, which references are hereby all incorporated by reference.

According to certain embodiments, the lignocellulose-containing material is pre-treated mechanically. As used herein, the term "pre-treated mechanically" or "mechanical pre-treatment" refers to any mechanical (or physical) treatment which promotes the separation and/or release of cellulose, hemicellulose and/or lignin from lignocellulose-containing material. For example, mechanical pre-treatment includes various types of milling, irradiation, steaming/steam explosion, and hydrothermolysis.

Mechanical pre-treatment includes comminution (mechanical reduction of the size). Comminution includes dry milling, wet milling and vibratory ball milling. Mechanical pre-treatment may involve high pressure and/or high temperature (steam explosion). In an embodiment of the invention high pressure means pressure in the range from about 300 to about 600 psi, such as from about 400 to about 500 psi, such as at about 450 psi. In an embodiment of the invention high temperature means temperatures in the range from about 100 to about 300° C., such as from about 140 to about 235° C. In a preferred embodiment, mechanical pre-treatment is a batch-process, steam gun hydrolyzer system which uses high pressure and high temperature as defined above. A Sunds Hydrolyzer (available from Sunds Defibrator AB (Sweden) may be used for this.

According to particular embodiments, both chemical and mechanical pre-treatments are carried out. For instance, the pre-treatment step may involve dilute or mild acid treatment and high temperature and/or pressure treatment. The chemical and mechanical pre-treatment may be carried out sequentially or simultaneously, as desired.

Accordingly, in a particular embodiment, the lignocellulose-containing material is subjected to both chemical and mechanical pre-treatment to promote the separation and/or release of cellulose, hemicellulose and/or lignin.

In one embodiment the pre-treatment is carried out as a dilute and/or mild acid steam explosion step. In another preferred embodiment pre-treatment is carried out as an ammonia fiber explosion step (or AFEX pre-treatment step).

According to certain embodiments, the lignocellulose-containing material is pre-treated biologically. As used herein, the term "pre-treated biologically" or "biological pre-treatment" refers to any biological pre-treatment which promotes the separation and/or release of cellulose, hemicellulose, and/or lignin from the lignocellulose-containing material. Biological pre-treatment techniques can involve applying lignin-solubilizing microorganisms (see, for example, Hsu, 1996, Pretreatment of biomass, in Handbook on Bioethanol: Production and Utilization, Wyman, ed., Taylor & Francis, Washington, D.C., 179-212; Ghosh and Singh, 1993, Physicochemical and biological treatments for enzymatic/microbial conversion of lignocellulosic biomass, Adv. Appl. Microbiol. 39: 295-333; McMillan, 1994, Pretreating lignocellulosic biomass: a review, in Enzymatic Conversion of Biomass for Fuels Production, Himmel, Baker, and Overend, eds., ACS Symposium Series 566, American Chemical Society, Washington, D.C., chapter 15; Gong, Cao, Du, and Tsao, 1999, Ethanol production from renewable resources, in Advances in Biochemical Engineering/Biotechnology, Scheper, ed., Springer-Verlag Berlin Heidelberg, Germany, 65: 207-241; Olsson and Hahn-Hagerdal, 1996, Fermentation of lignocellulosic hydrolysates for ethanol production, Enz. Microb. Tech. 18: 312-331; and Vallander and Eriksson, 1990, Production of ethanol from lignocellulosic materials: State of the art, Adv. Biochem. Eng J Biotechnol. 42: 63-95).

The pre-treated lignocellulose-containing material is then hydrolyzed to break down cellulose and/or hemicellulose. This process converts the carbohydrate polymers into fermentable sugars which, by using a fermenting organism, e.g. a bacterium or yeast, may be fermented into a desired fermentation product, such as ethanol.

According to certain embodiments, in step (b) the pre-treated lignocellulose-containing material is hydrolyzed chemically, e.g., by acid treatment, such as dilute acid treatment. Suitable conditions for chemical hydrolysis, and more particular acid hydrolysis, of lignocellulose-containing material are well known to one skilled in the art.

According to certain other embodiments, in step (b) the pre-treated lignocellulose-containing material is hydrolyzed enzymatically, e.g., by one or more cellulolytic enzymes, to form a hydrolyzate.

The enzyme(s) used for hydrolysis is (are) capable of directly or indirectly converting carbohydrate polymers into fermentable sugars which can be fermented into a desired fermentation product, such as ethanol.

Hydrolysis in step (b) may also be carried out in the presence of one or more cellulolytic enzymes and/or one or more hemicellulolytic enzymes. According to certain embodiments, hydrolysis in step (b) is carried out in the presence of at least one cellulolytic enzyme. According to certain other embodiments, hydrolysis in step (b) is carried out in the presence of at least one hemicellulolytic enzyme. According to certain embodiments, hydrolysis in step (b) is carried out in the presence of a combination of at least one cellulolytic enzyme and at least one hemicellulolytic enzyme.

The term "cellulolytic enzymes" as used herein are understood as comprising cellobiohydrolases (EC 3.2.1.91), e.g., cellobiohydrolase I and cellobiohydrolase II, as well as the endoglucanases (EC 3.2.1.4) and beta-glucosidases (EC 3.2.1.21).

1,4-beta-D-glucan cellobiohydrolases (E.C.3.2.1.91), also referred herein as "cellobiohydrolases", catalyze the hydrolysis of 1,4-beta-D-glucosidic linkages in cellulose, cello-oligosaccharides, or any beta-1,4-linked glucose containing polymer, releasing cellobiose from the reducing or non-reducing ends of the chain.

Endoglucanases (E.C.3.2.1.4) catalyze the endo hydrolysis of 1,4-beta-D-glycosidic linkages in cellulose, cellulose derivatives (such as carboxy methyl cellulose and hydroxy ethyl cellulose), lichenin, beta-1,4 bonds in mixed beta-1,3 glucans such as cereal beta-D-glucans or xyloglucans and other plant material containing cellulosic parts. The authorized name is endo-1,4-beta-D-glucan 4-glucanohydrolase, but the abbreviated term endoglucanase is used in the present specification. Endoglucanase activity may be determined using carboxy methyl cellulose (CMC) hydrolysis according to the procedure of Ghose, 1987, Pure and Appl. Chem. 59: 257-268.

"Beta-glucosidases" (E.C.3.2.1.21), also referred herein as "beta-D-glucoside glucohydrolases", catalyze the hydrolysis of terminal non-reducing beta-D-glucose residues with the release of beta-D-glucose. For purposes of the present invention, beta-glucosidase activity is determined according to the basic procedure described by Venturi et al., 2002, J. Basic Microbiol. 42: 55-66. One unit of beta-glucosidase activity is defined as 1.0 µmole of p-nitrophenol produced per minute at 50° C., pH 5 from 4 mM p-nitrophenyl-beta-D-glucopyranoside as substrate in 100 mM sodium citrate, 0.01% TWEEN® 20.

In order to be efficient, the digestion of cellulose may require several types of enzymes acting cooperatively. At least three categories of enzymes are often employed in converting cellulose into glucose: endoglucanases (EC 3.2.1.4) that cut the cellulose chains at random; cellobiohydrolases (EC 3.2.1.91) which cleave cellobiosyl units from the cellulose chain ends and beta-glucosidases (EC 3.2.1.21) that convert cellobiose and soluble cellodextrins into glucose. Among these three categories of enzymes involved in the biodegradation of cellulose, cellobiohydrolases are the key enzymes for the degradation of native crystalline cellulose.

The term "cellobiohydrolase I" is defined herein as a cellulose 1,4-beta-cellobiosidase (also referred to as Exo-glucanase, Exo-cellobiohydrolase or 1,4-beta-cellobiohydrolase) activity, as defined in the enzyme class EC 3.2.1.91, which catalyzes the hydrolysis of 1,4-beta-D-glucosidic linkages in cellulose and cellotetraose, by the release of cellobiose from the non-reducing ends of the chains. The definition of the term "cellobiohydrolase II activity" is identical, except that cellobiohydrolase II attacks from the reducing ends of the chains.

Hence, according to certain embodiments, at least one, such as at least two, at least three, at least four, at least five, at least six or at least seven, cellulolytic enzymes selected from the group consisting of endoglucanases, cellobiohydrolases, beta-glucosidases and combinations thereof is (are) employed in step (b).

The cellulolytic enzyme may comprise a carbohydrate-binding module (CBM) which enhances the binding of the enzyme to a lignocellulose-containing fiber and increases the efficacy of the catalytic active part of the enzyme. A CBM is defined as contiguous amino acid sequence within a carbohydrate-active enzyme with a discreet fold having carbohydrate-binding activity.

According to particular embodiments, the cellulolytic enzyme is a cellulolytic enzyme preparation, such as a preparation described in U.S. application No. 60/941,251, which is hereby incorporated by reference. According to more particular embodiments, the cellulolytic enzyme preparation comprises a polypeptide having cellulolytic enhancing activity (GH61A), such as the GH61A enzyme from *Thermoascus aurantiacus* as disclosed, e.g., in WO2005/074656 (hereby incorporated by reference). The cellulolytic enzyme preparation may further comprise a beta-glucosidase, such as a beta-glucosidase derived from a strain of the genus *Humicola, Trichoderma, Aspergillus* or *Penicillium*, including the *Humicola insolens* CEL45A endoglucanase core/*Aspergillus oryzae* beta-glucosidase fusion protein disclosed in, e.g., U.S. application Ser. No. 11/781,151 or PCT/US2007/074038 (Novozymes). According to certain embodiment, the cellulolytic enzyme preparation may also comprise a CBH II, such as *Thielavia terrestris* cellobiohydrolase II (CEL6A). According to other certain embodiments, the cellulolytic enzyme preparation also comprises a cellulase enzyme preparation, such as a cellulase enzyme preparation derived from *Trichoderma reesei*.

According to certain embodiments, the cellulolytic enzyme preparation comprises a polypeptide having cellulolytic enhancing activity (GH61A); a cellobiohydrolase, such as *Thielavia terrestris* cellobiohydrolase II (CEL6A), a beta-glucosidase (e.g., the fusion protein disclosed in U.S. application No. 60/832,511) and cellulolytic enzymes, e.g., derived from *Trichoderma reesei*.

The term "cellulolytic enhancing activity" is defined herein as a biological activity that enhances the hydrolysis of a lignocellulose derived material by proteins having cellulolytic activity. For purposes of the present invention, cellulolytic enhancing activity is determined by measuring the increase in reducing sugars or in the increase of the total of cellobiose and glucose from the hydrolysis of a lignocellulose derived material, e.g., pre-treated lignocellulose-containing material by cellulolytic protein under the following conditions: 1-50 mg of total protein/g of cellulose in PCS (pre-treated corn stover), wherein total protein is comprised of 80-99.5% w/w cellulolytic protein/g of cellulose in PCS and 0.5-20% w/w protein of cellulolytic enhancing activity for 1-7 day at 50° C. compared to a control hydrolysis with equal total protein loading without cellulolytic enhancing activity (1-50 mg of cellulolytic protein/g of cellulose in PCS).

According to certain embodiments, the hydrolysis in step (b) is carried out in the presence of at least one cellulolytic enzyme in combination with a polypeptide having enhancing activity. According to particular embodiments, the polypeptide having enhancing activity is a family GH61A polypeptide. For example, WO2005/074647 discloses isolated polypeptides having cellulolytic enhancing activity and polynucleotides thereof from *Thielavia terrestris*, WO2005/074656 discloses an isolated polypeptide having cellulolytic enhancing activity and a polynucleotide thereof from *Thermoascus aurantiacus*, and U.S. Application Publication No. 2007/0077630 discloses an isolated polypeptide having cellulolytic enhancing activity and a polynucleotide thereof from *Trichoderma reesei*.

According to certain embodiments, the cellulolytic enzyme is the commercially available product CELLUCLAST® 1.5 L or CELLUZYME™ available from Novozymes A/S, Denmark, or ACCELERASE™ 1000 available from Genencor Inc., USA.

The cellulolytic enzyme may, in accordance to particular embodiments, be derived from a fungal source, such as from a strain of the genus *Trichoderma*, such as from a strain of *Trichoderma reesei*; or from a strain of the genus *Humicola*, such as from a strain of *Humicola insolens*; or from a strain of the genus *Chrysosporium*, such as from a strain of *Chrysosporium lucknowense*.

According to certain embodiments, at least one endoglucanase is employed in step (b).

According to particular embodiments, the endoglucanase is derived from a strain of the genus *Trichoderma*, such as from a strain of *Trichoderma reesei*; from a strain of the genus *Humicola*, such as from a strain of *Humicola insolens*; or from a strain of the genus *Chrysosporium*, such as from a strain of *Chrysosporium lucknowense*.

According to certain embodiments, at least one beta-glucosidase is employed in step (b).

According to certain embodiments, the beta-glucosidase is of fungal origin, such as derived from a strain of the genus *Trichoderma, Aspergillus* or *Penicillium*. According to particular embodiments, the beta-glucosidase is a derived from *Trichoderma reesei*, such as the beta-glucosidase encoded by the bgl1 gene (see FIG. 1 of EP 562003). According to other particular embodiments, the beta-glucosidase is derived from *Aspergillus oryzae, Aspergillus fumigatus* (e.g., recombinantly produced in *Aspergillus oryzae* according to Example 22 of WO02/095014) or *Aspergillus niger.*

According to certain embodiments, at least one cellobiohydrolase is employed in step (b).

The one or more cellulolytic enzymes may be dosed in the range from 0.1-100 FPU per gram dry solids (DS), preferably 0.5-50 FPU per gram dry solids, especially 1-20 FPU per gram dry solids. The cellulolytic enzyme may be dosed in the range from 1-1000 EGU per gram dry solids, preferably 10-500 EGU per gram dry solids, especially 50 to 200 EGU per gram dry solids.

According to certain embodiments, at least 1 mg cellulolytic enzyme per gram dry solids, such as at least 2 mg or at least 3 mg cellulolytic enzyme per gram dry solids, such as between 5 and 10 mg cellulolytic enzyme(s) is(are) used for hydrolysis.

Hemicellulose polymers can be broken down by hemicellulases and/or acid hydrolysis to release its five and six carbon sugar components. The six carbon sugars (hexoses), such as glucose, galactose, arabinose, and mannose, can readily be fermented to, e.g., ethanol, acetone, butanol, glycerol, citric acid, fumaric acid, etc. by suitable fermenting organisms including yeast. Preferred for ethanol fermentation is yeast of the species *Saccharomyces cerevisiae*, preferably strains which are resistant towards high levels of ethanol, i.e., up to, e.g., about 10, about 12 or about 15 vol. % ethanol or more, such as about 20 vol. % ethanol.

Accordingly, in step (b) the pre-treated lignocellulose-containing material may be subjected to at least one, such as at least two or at least three, hemicellulolytic enzyme, such as a hemicellulase.

Any hemicellulase suitable for use in hydrolyzing hemicellulose, such as into xylose, may be used. Suitable hemicellulases include xylanases, arabinofuranosidases, acetyl xylan esterase, feruloyl esterase, glucuronidases, endo-galactanase, mannases, endo or exo arabinases, exo-galactanses, and mixtures of two or more thereof. The hemicellulase for use in the present invention may be an exo-acting hemicellulase, and more particularly an exo-acting hemicellulase which has the ability to hydrolyze hemicellulose under acidic conditions of below pH 7, preferably pH 3-7. An example of hemicellulase suitable for use in the present invention includes VISCOZYME™ (available from Novozymes A/S, Denmark).

According to certain embodiments, the hemicellulase is a xylanase. According to particular embodiments, the xylanase is of microbial origin, such as of fungal origin (e.g., derived from a strain of the genus *Trichoderma, Meripilus, Humicola, Aspergillus*, or *Fusarium*) or of bacterial origin (e.g., derived from a strain of the genus *Bacillus*). According to particular embodiments, the xylanase is derived from a filamentous fungus, such as from a strain of the genus *Aspergillus*, such as from an *Aspergillus aculeatus* strain; or from a strain of the genus *Humicola*, such as from an *Humicola lanuginose* strain. The xylanase may also be an endo-1,4-beta-xylanase, such as an endo-1,4-beta-xylanase of GH10 or GH11. Examples of commercial xylanases include SHEARZYME™ and BIOFEED WHEAT™ from Novozymes A/S, Denmark.

The hemicellulase may be added in an amount effective to hydrolyze hemicellulose, such as, in amounts from about 0.001 to 0.5 wt.-% of dry solids, more preferably from about 0.05 to 0.5 wt.-% of dry solids.

Xylanases may be added in amounts of 0.001-1.0 g/kg dry solids, preferably in the amounts of 0.005-0.5 g/kg dry solids, and most preferably from 0.05-0.10 g/kg dry solids.

Other hydrolytic enzymes may also be present during hydrolysis. Contemplated enzymes include alpha-amylases; glucoamylases or another carbohydrate-source generating enzymes, such as beta-amylases, maltogenic amylases and/or alpha-glucosidases; proteases; or mixtures of two of more thereof.

Hydrolysis may according to certain embodiment be carried out as a fed batch process where the pre-treated lignocellulose-containing material is fed gradually to an, e.g., enzyme containing hydrolysis solution.

Enzymatic hydrolysis may be carried out in a suitable aqueous environment under conditions which can readily be determined by one skilled in the art. According to particular embodiments, hydrolysis is carried out at suitable, preferably optimal conditions for the enzyme(s) in question.

Suitable process time, temperature and pH conditions can readily be determined by one skilled in the art. For example, hydrolysis in step (b) may be carried out at a temperature in the range from about 20° C. to about 80° C., such as from about 20° C. to about 70° C., from about 20° C. to about 60° C., from about 20° C. to about 50° C., from about 20° C. to about 40° C., from about 20° C. to about 37° C. from about 25° C. to about 60° C., from about 25° C. to about 50° C., from about 25° C. to about 40° C. or from about 25° C. to about 37° C. According to certain embodiments, hydrolysis in step (b) is carried out at a temperature in the range from about 25° C. to about 40° C.

Hydrolysis in step (b) may, for example, be carried out at a pH ranging from about pH 1 to about pH 9, but will normally range from about pH 5.0 to about pH 9.0, such as from about pH 5.5 to about pH 8.0, such as from about pH 6 to about pH 7.5, such as from about pH 6.5 to about pH 7, such as at about pH 6 or pH 7. According to certain embodiments, hydrolysis in step (b) is carried out at a pH ranging from about pH 5.5 to about pH 8.0. According to certain other embodiments, hydrolysis in step (b) is carried out at a pH ranging from about pH 6 to about pH 8, such as from about pH 6.5 to about pH 7.5.

Hydrolysis in step (b) may, for example, be carried out for at least about 4 hours, such as for at least about 8 hours, at least about 12 hours, at least about 18 hours, at least about 24 hours, at least about 48 hours, at least about 72 hours, at least about 96 hours, at least about one week, at least about two weeks, at least about one month or at least about 3 months. According to certain embodiments, hydrolysis in step (b) is carried out for at least about 8 hours.

Since a range of toxic/inhibiting phenolic compounds are produced (e.g. released) during the pre-treatment step (a) and/or the hydrolysis step (b) it is desirable to make them non-toxic, or at least less toxic, especially if the hydrolyzed product is to be further fermented by a fermenting organism. This is done by enzymatically sulfating the phenolic compounds produced (e.g. released) during the pre-treatment step (a) and/or the hydrolysis step (b).

In the present context, it should be understood that the phenolic compounds includes those compounds in which a hydroxyl group is directly attached to a benzenoid carbon atom, and which compounds may or may not contain other substituent groups.

A special group of enzymes that are suitable for sulfating phenolic compounds are aryl sulfotransferases (EC 2.8.2.1). The conversion of inhibitory or toxic phenolic compounds to their sulfated derivative has been shown by the inventors to result in detoxification. As an example, it has been shown that presence of an aryl sulfotransferase increases the tolerance of *E. coli* towards inhibitory or toxic phenolic compounds such as ferulic acid (Example 4).

The sulfating step (c) can be performed in several ways, e.g. by direct addition of a polypeptide having aryl sulfotransferase activity, or by addition of an organism, such as recombinant host cell, comprising (e.g., expressing) a polypeptide having aryl sulfotransferase activity.

The polypeptide having aryl sulfotransferase activity may be a sulfotransferase 1A1 enzyme, a sulfotransferase 1A2 enzyme, a sulfotransferase 1A3 enzyme, a sulfotransferase 1B1 enzyme, a sulfotransferase 1C1 enzyme, a sulfotransferase 1C2 enzyme, a sulfotransferase 1C4 enzyme, or a sulfotransferase 1E1 enzyme. According to certain embodiments, the polypeptide having aryl sulfotransferase activity is a sulfotransferase 1A1 enzyme. According to certain other embodiments, the polypeptide having aryl sulfotransferase activity is a sulfotransferase 1A2 enzyme. According to certain embodiments, the polypeptide having aryl sulfotransferase activity is a sulfotransferase 1B1 enzyme. According to certain embodiments, the polypeptide having aryl sulfotransferase activity is a sulfotransferase 1C1 enzyme. According to certain embodiments, the polypeptide having aryl sulfotransferase activity is a sulfotransferase 1C2 enzyme. According to certain embodiments, the polypeptide having aryl sulfotransferase activity is a sulfotransferase 1C4 enzyme. According to other certain embodiments, the polypeptide having aryl sulfotransferase activity is a sulfotransferase 1E1 enzyme (estrogen sulfotransferase), such as the sulfotransferase 1E1 from *Gallus gallus domesticus*.

According to certain embodiments, the polypeptide having aryl sulfotransferase activity is a mammalian aryl sulfotransferase, such as a mammalian sulfotransferase 1A1 enzyme.

According to certain embodiments, the polypeptide having aryl sulfotransferase activity is an aryl sulfotransferase from *Rattus norvegicus* or a variant thereof. Such variant may have at least about 70%, such as at least about 75%, at least about 80%, at least about 85%, at least about 90%, at least about 93%, at least 95%, at least 96%, at least 97%, at least 98%, or at least 99%, sequence identity to the amino acid sequence of the aryl sulfotransferase from *Rattus norvegicus*. Such variant may also have an amino acid sequence of the sulfotransferase from *Rattus norvegicus*, wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

It is understood that the foregoing values generally define the total number of alterations to the reference aryl sulfotransferase. The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

According to certain embodiments, the polypeptide having aryl sulfotransferase activity may be a polypeptide selected from the group consisting of:
i) a polypeptide comprising an amino acid sequence set forth in SEQ ID NO: 1, 2, 3, 4, 5, 6, 7, 8, 9, 10, 11, 12 or 13 (e.g., SEQ ID NO: 1);
ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1, 2, 3, 4, 5, 6, 7, 8, 9, 10, 11, 12 or 13 (e.g., SEQ ID NO: 1); or
iii) a polypeptide comprising an amino acid sequence set forth in SEQ ID NO: 1, 2, 3, 4, 5, 6, 7, 8, 9, 10, 11, 12 or 13 (e.g., SEQ ID NO: 1), wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

According to certain embodiments, a polypeptide having aryl sulfotransferase activity is a polypeptide according to i). Accordingly, a polypeptide having aryl sulfotransferase activity may be a polypeptide comprising an amino acid sequence set forth in SEQ ID NO: 1, 2, 3, 4, 5, 6, 7, 8, 9, 10, 11, 12 or 13 (e.g., SEQ ID NO: 1). According to particular embodiments, a polypeptide according to i) comprises an amino acid sequence set forth in SEQ ID NO: 1. According other particular embodiments, a polypeptide according to i) comprises an amino acid sequence set forth in SEQ ID NO: 2. According to yet other particular embodiments, a polypeptide according to i) comprises an amino acid sequence set forth in SEQ ID NO: 3. According to yet other particular embodiments, a polypeptide according to i) comprises an amino acid sequence set forth in SEQ ID NO: 4. According to yet other particular embodiments, a polypeptide according to i) comprises an amino acid sequence set forth in SEQ ID NO: 5. According other particular embodiments, a polypeptide according to i) comprises an amino acid sequence set forth in SEQ ID NO: 6. According other particular embodiments, a polypeptide according to i) comprises an amino acid sequence set forth in SEQ ID NO: 7. According other particular embodiments, a polypeptide according to i) comprises an amino acid sequence set forth in SEQ ID NO: 8. According other particular embodiments, a polypeptide according to i) comprises an amino acid sequence set forth in SEQ ID NO: 9. According other particular embodiments, a polypeptide according to i) comprises an amino acid sequence set forth in SEQ ID NO: 10. According other particular embodiments, a polypeptide according to i) comprises an amino acid sequence set forth in SEQ ID NO: 11. According other particular embodiments, a polypeptide according to i) comprises an amino acid sequence set forth in SEQ ID NO: 12. According other particular embodiments, a polypeptide according to i) comprises an amino acid sequence set forth in SEQ ID NO: 13.

According to other certain embodiments, a polypeptide having aryl sulfotransferase activity is a polypeptide according to ii). Accordingly, a polypeptide having aryl sulfotransferase activity may be a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1, 2, 3, 4, 5, 6, 7, 8, 9, 10, 11, 12 or 13 (e.g., SEQ ID NO: 1). According to particular embodiments, a polypeptide according to ii) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 1, 2, 3, 4, 5, 6, 7, 8, 9, 10, 11, 12 or 13 (e.g., SEQ ID NO: 1). According to other particular embodiments, a polypeptide according to ii) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 1, 2, 3, 4, 5, 6, 7, 8, 9, 10, 11, 12 or 13 (e.g., SEQ ID NO: 1). According to other particular embodiments, a polypeptide according to ii) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 1, 2, 3, 4, 5, 6, 7, 8, 9, 10, 11, 12 or 13 (e.g., SEQ ID NO: 1). According to other particular embodiments, a polypeptide according to ii) comprises an amino acid sequence which has at least about 95%, such as at least about 96%, at least about 97%, at least about 98%, or at least about 99%, sequence identity to the amino acid sequence set forth in SEQ ID NO: 1, 2, 3, 4, 5, 6, 7, 8, 9, 10, 11, 12 or 13 (e.g., SEQ ID NO: 1).

According to particular embodiments, a polypeptide according to ii) comprises an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1. According to more particular embodiments, a polypeptide according to ii) comprises an amino acid sequence which has at least about 80%, such as at least about 85%, at least about 90%, at least about 93%, at least about 95%, at least about 96%, at least about 97%, at least about 98%, or at least about 99%, sequence identity to the amino acid sequence set forth in SEQ ID NO: 1. According to other more particular embodiments, a polypeptide according to ii) comprises an amino acid sequence which has at least about 85%, such as at least about 90%, at least about 93%, at least about 95%, at least about 96%, at least about 97%, at least about 98%, or at least about 99%, sequence identity to the amino acid sequence set forth in SEQ ID NO: 1. According to other more particular embodiments, a polypeptide according to ii) comprises an amino acid sequence which has at least about 90%, such as at least about 93%, at least about 95%, at least about 96%, at least about 97%, at least about 98%, or at least about 99%, sequence identity to the amino acid sequence set forth in SEQ ID NO: 1. According to other more particular embodiments, a polypeptide according to ii) comprises an amino acid sequence which has at least about 95%, such as at least about 96%, at least about 97%, at least about 98%, or at least about 99%, sequence identity to the amino acid sequence set forth in SEQ ID NO: 1.

Preferably, a polypeptide according to i) has aryl sulfotransferase activity. More preferably, a polypeptide according to ii) has a aryl sulfotransferase activity similar to that of the polypeptide comprising an amino acid sequence set forth in SEQ ID NO: 1, 2, 3, 4, 5, 6, 7, 8, 9, 10, 11, 12 or 13 (e.g., SEQ ID NO: 1).

According to certain embodiment, a polypeptide according to ii) has aryl sulfotransferase activity similar to that of the polypeptide comprising the amino acid sequence set forth in SEQ ID NO: 1. According to certain other embodiments, a polypeptide according to ii) has aryl sulfotransferase activity similar to that of the polypeptide comprising the amino acid sequence set forth in SEQ ID NO: 2. According to certain other embodiments, a polypeptide according to ii) has aryl sulfotransferase activity similar to that of the polypeptide comprising the amino acid sequence set forth in SEQ ID NO: 3. According to certain other embodiments, a polypeptide according to ii) has aryl sulfotransferase activity similar to that of the polypeptide comprising the amino acid sequence set forth in SEQ ID NO: 4. According to certain other embodiments, a polypeptide according to ii) has aryl sulfotransferase activity similar to that of the polypeptide comprising the amino acid sequence set forth in SEQ ID NO: 5. According to certain other embodiments, a polypeptide according to ii) has aryl sulfotransferase activity similar to that of the polypeptide comprising the amino acid sequence set forth in SEQ ID NO: 6. According to certain other embodiments, a polypeptide according to ii) has aryl sulfotransferase activity similar to that of the polypeptide comprising the amino acid sequence set forth in SEQ ID NO: 7. According to certain other embodiments, a polypeptide according to ii) has aryl sulfotransferase activity similar to that of the polypeptide comprising the amino acid sequence set forth in SEQ ID NO: 8. According to certain other embodiments, a polypeptide according to ii) has aryl sulfotransferase activity similar to that of the polypeptide comprising the amino acid sequence set forth in SEQ ID NO: 9. According to certain other embodiments, a polypeptide according to ii) has aryl sulfotransferase activity similar to that of the polypeptide comprising the amino acid sequence set forth in SEQ ID NO: 10. According to certain other embodiments, a polypeptide according to ii) has aryl sulfotransferase activity similar to that of the polypeptide comprising the amino acid sequence set forth in SEQ ID NO: 11. According to certain other embodiments, a polypeptide according to ii) has aryl sulfotransferase activity similar to that of the polypeptide comprising the amino acid sequence set forth in SEQ ID NO: 12. According to certain other embodiments, a polypeptide according to ii) has aryl sulfotransferase activity similar to that of the polypeptide comprising the amino acid sequence set forth in SEQ ID NO: 13.

With "similar" aryl sulfotransferase activity, it is meant that the polypeptide according to ii) has at least about 10%, such as at least about 20%, at least about 30%, at least about 40%, at least about 50%, at least about 60, at least about 75%, at least about 80%, at least about 90%, at least about 95%, at least about 100%, at least about 200%, at least about 300%, at least about 400%, at least about 500%, at least about 800%, at least about 1000% or at least about 2000%, of the aryl sulfotransferase activity of the reference polypeptide (e.g., SEQ ID NO: 1).

The aryl sulfotransferase activity may for instance be determined in accordance to the following method: Aryl sulfotransferase activity may be determined by the reaction of radioactively sulfur labeled PAPS, [$^{35}$S]PAPS, with the substrate in presence of the polypeptide of interest. This is described previously, for example by Hattori et al (Biosci Biotechnol Biochem. 2008; 72(2):540-7). The reaction takes place in a buffer such as 250 μL 50 mM sodium phosphate pH 6.8 with 1 μM [$^{35}$S]PAPS (3.7 kBq) with 100 μM accepting compound for a period of 30 min at 30° C. The reaction is stopped by addition of 100 μL of a 1:1 mixture of 0.1 M barium acetate and barium hydroxide. 50 μL of 0.1 M zinc sulfate is added, followed by centrifugation at 1,200×g for 5 min. 300 μL of the supernatant is then transferred to a new container and 50 μL of an equal volume of 0.1 M barium hydroxide and 0.1 M zinc sulfate is added. The mixture is then centrifuged at 13,000×g for 5 min, and 300-μL aliquots of the supernatant are mixed with 2.5 mL of Cleasol I (Nacalai Tesque, Kyoto, Japan). The radioactivity is then measured by scintillation.

Alternatively, the activity of a sulfotransferase may be detected by direct measurement of the product by analytical methods such as high performance liquid chromatography (HPLC) or liquid chromatography in combination with mass spectrometry (LC-MS).

According to other certain embodiments, a polypeptide having aryl sulfotransferase activity is a polypeptide according to iii). Accordingly, a polypeptide having aryl sulfotransferase activity may be a polypeptide comprising an amino acid sequence set forth in SEQ ID NO: 1, 2, 3, 4, 5, 6, 7, 8, 9, 10, 11, 12 or 13 (e.g., SEQ ID NO: 1), wherein 1 or more, such as 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 25 or more, 30 or more, 35 or more, 40 or more, 45 or more, 50 or more, 60 or more, 70 or more, 80 or more, 90 or more, 100 or more, 110 or more, 120 or more, 130 or more, 140 or more, or 150 or more, amino acid residues are substituted, deleted, and/or inserted. According to particular embodiments, a polypeptide according to iii) comprises an amino acid sequence set forth in SEQ ID NO: 1, 2, 3, 4, 5, 6, 7, 8, 9, 10, 11, 12 or 13 (e.g., SEQ ID NO: 1), wherein about 1 to about 150, such as about 1 to about 140, about 1 to about 130, about 1 to about 120, about 1 to about 110, about 1 to about 100, about 1 to about 90, about 1 to about 80, about 1 to about 70, about 1 to about 60, about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to iii) comprises an amino acid sequence set forth in SEQ ID NO: 1, 2, 3, 4, 5, 6, 7, 8, 9, 10, 11, 12 or 13 (e.g., SEQ ID NO: 1), wherein about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to iii) comprises an amino acid sequence set forth in SEQ ID NO: 1, 2, 3, 4, 5, 6, 7, 8, 9, 10, 11, 12 or 13 (e.g., SEQ ID NO: 1), wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to iii) comprises an amino acid sequence set forth in SEQ ID NO: 1, 2, 3, 4, 5, 6, 7, 8, 9, 10, 11, 12 or 13 (e.g., SEQ ID NO: 1), wherein about 1 to about 25, such as about 1 to about 20, about 1 to about 15, about 1 to about 10, about 1 to about 5, or about 1 to about 3, amino acid residues are substituted, deleted and/or inserted.

According to particular embodiments, a polypeptide according to iii) comprises an amino acid sequence set forth in SEQ ID NO: 1, wherein about 1 to about 150, such as about 1 to about 140, about 1 to about 130, about 1 to about 120, about 1 to about 110, about 1 to about 100, about 1 to about 90, about 1 to about 80, about 1 to about 70, about 1 to about 60, about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to more particular embodiments, a polypeptide according to iii) comprises an amino acid sequence set forth in SEQ ID NO: 1, wherein about 1 to about 50, about 1 to about 40, about 1 to about 35, about 1 to about 30, about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to iii) comprises an amino acid sequence set forth in SEQ ID NO: 1, wherein about 1 to about 30, such as about 1 to about 25, about 1 to about 20, about 1 to about 15, about 1 to about 10, about 1 to about 5, or about 1 to about 3, amino acid residues are substituted, deleted and/or inserted. According to other more particular embodiments, a polypeptide according to iii) comprises an amino acid sequence set forth in SEQ ID NO: 1, wherein about 1 to about 25, such as about 1 to about 20, about 1 to about 15, about 1 to about 10, about 1 to about 5, or about 1 to about 3, amino acid residues are substituted, deleted and/or inserted.

It is understood that the foregoing values generally define the total number of alterations to the reference polypeptide (e.g., SEQ ID NO: 1). The alterations may solely be amino acid substitutions, be it conserved or non-conserved substitutions, or both. They may solely be amino acid deletions. They may solely be amino acid insertions. The alterations may be a mix of these specific alterations, such as amino acid substitutions and amino acid insertions.

Preferably, a polypeptide according to iii) has aryl sulfotransferase activity. More preferably, a polypeptide according to iii) has a aryl sulfotransferase activity similar to that of the polypeptide comprising an amino acid sequence set forth in SEQ ID NO: 1, 2, 3, 4, 5, 6, 7, 8, 9, 10, 11, 12 or 13 (e.g., SEQ ID NO: 1).

According to certain embodiment, a polypeptide according to iii) has aryl sulfotransferase activity similar to that of the polypeptide comprising the amino acid sequence set forth in SEQ ID NO: 1. According to certain other embodiments, a polypeptide according to iii) has aryl sulfotransferase activity similar to that of the polypeptide comprising the amino acid sequence set forth in SEQ ID NO: 2. According to certain other embodiments, a polypeptide according to iii) has aryl sulfotransferase activity similar to that of the polypeptide comprising the amino acid sequence set forth in SEQ ID NO: 3. According to certain other embodiments, a polypeptide according to iii) has aryl sulfotransferase activity similar to that of the polypeptide comprising the amino acid sequence set forth in SEQ ID NO: 4. According to certain other embodiments, a polypeptide according to iii) has aryl sulfotransferase activity similar to that of the polypeptide comprising the amino acid sequence set forth in SEQ ID NO: 5. According to certain other embodiments, a polypeptide according to iii) has aryl sulfotransferase activity similar to that of the polypeptide comprising the amino acid sequence set forth in SEQ ID NO: 6. According to certain other embodiments, a polypeptide according to iii) has aryl sulfotransferase activity similar to that of the polypeptide comprising the amino acid sequence set forth in SEQ ID NO: 7. According to certain other embodiments, a polypeptide according to iii) has aryl sulfotransferase activity similar to that of the polypeptide comprising the amino acid sequence set forth in SEQ ID NO: 8. According to certain other embodiments, a polypeptide according to iii) has aryl sulfotransferase activity similar to that of the polypeptide comprising the amino acid sequence set forth in SEQ ID NO: 9. According to certain other embodiments, a polypeptide according to iii) has aryl sulfotransferase activity similar to that of the polypeptide comprising the amino acid sequence set forth in SEQ ID NO: 10. According to certain other embodiments, a polypeptide according to iii) has aryl sulfotransferase activity similar to that of the polypeptide comprising the amino acid sequence set forth in SEQ ID NO: 11. According to certain other embodiments, a polypeptide according to iii) has aryl sulfotransferase activity similar to that of the polypeptide comprising the amino acid sequence set forth in SEQ ID NO: 12. According to certain other embodiments, a polypeptide according to iii) has aryl sulfotransferase activity similar to that of the polypeptide comprising the amino acid sequence set forth in SEQ ID NO: 13.

With "similar" aryl sulfotransferase activity it is meant that the polypeptide according to iii) has at least about 10%, such as at least about 20%, at least about 30%, at least about 40%, at least about 50%, at least about 60, at least about 75%, at least about 80%, at least about 90%, at least about 95%, at least about 100%, at least about 200%, at least about 300%, at least about 400%, at least about 500%, at least about 800%, at least about 1000% or at least about 2000%, of the aryl sulfotransferase activity of the reference polypeptide (e.g., SEQ ID NO: 1).

The aryl sulfotransferase activity may for instance be determined in accordance to the following method: Aryl sulfotransferase activity may be determined by the reaction of radioactively sulfur labeled PAPS, [$^{35}$S]PAPS, with the substrate in presence of the polypeptide of interest. This is described previously, for example by Hattori et al (Biosci Biotechnol Biochem. 2008; 72(2):540-7). The reaction takes place in a buffer such as 250 μL 50 mM sodium phosphate pH 6.8 with 1 μM [$^{35}$S]PAPS (3.7 kBq) with 100 μM accepting compound for a period of 30 min at 30° C. The reaction is stopped by addition of 100 μL of a 1:1 mixture of 0.1 M barium acetate and barium hydroxide. 50 μL of 0.1 M zinc sulfate is added, followed by centrifugation at 1,200×g for 5 min. 300 μL of the supernatant is then transferred to a new container and 50 μL of an equal volume of 0.1 M barium hydroxide and 0.1 M zinc sulfate is added. The mixture is then centrifuged at 13,000×g for 5 min, and 300-μL aliquots of the supernatant are mixed with 2.5 mL of Cleasol I (Nacalai Tesque, Kyoto, Japan). The radioactivity is then measured by scintillation.

Alternatively, the activity of a sulfotransferase may be detected by direct measurement of the product by analytical methods such as high performance liquid chromatography (HPLC) or liquid chromatography in combination with mass spectrometry (LC-MS).

The polypeptide having aryl sulfotransferase activity may be directly employed in step (c) in isolated form, such as in purified form. The polypeptides may for instance be expressed by a recombinant host cell, and then purified. Techniques and means for the purification of polypeptides produced by a recombinant host cell are well known in the art. For example, in order to facilitate purification, an amino acid motif comprising several histidine residues, such as at least 6, may be inserted at the C- or N-terminal end of the polypeptide. A non-limiting example of such amino acid motif is provided in SEQ ID NO: 14. Various purification kits for histidine-tagged polypeptides are available from commercial sources such as Qiagen, Hilden, Germany; Clontech, Mountain View, Calif., USA; Bio-Rad, Hercules, Calif., USA and others.

Alternatively, the polypeptides may be chemically synthesized. Techniques for chemical peptide synthesis are well known and include Liquid-phase synthesis and Solid-phase synthesis.

According to certain other embodiments, an organism, and more particularly a fermenting organism having aryl sulfotransferase activity, is employed in the sulfating step (c). Said organism, and more particularly said fermenting organism, may be a recombinant host cell comprising a heterologous polypeptide having sulfotransferase activity, preferably an aryl sulfotransferase activity.

A recombinant host cell utilized in accordance with the present invention may be a recombinant host cell comprising (e.g., expressing) a polypeptide having aryl sulfotransferase activity as detailed above. Generally, the polypeptide having aryl sulfotransferase activity will be heterologous to the host cells, which means that the polypeptide is normally not found in or made (i.e. expressed) by the host cells, but derived from a different species.

According to certain embodiments, in step (c) a recombinant host cell is employed comprising a heterologous polypeptide having an aryl sulfotransferase activity as detailed above. According to particular embodiments, the recombinant host cell comprises a heterologous polypeptide selected from the group consisting of:
i) a polypeptide comprising an amino acid sequence set forth in SEQ ID NO: 1, 2, 3, 4, 5, 6, 7, 8, 9, 10, 11, 12 or 13 (e.g., SEQ ID NO: 1);
ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 1, 2, 3, 4, 5, 6, 7, 8, 9, 10, 11, 12 or 13 (e.g., SEQ ID NO: 1); or
iii) a polypeptide comprising an amino acid sequence set forth in SEQ ID NO: 1, 2, 3, 4, 5, 6, 7, 8, 9, 10, 11, 12 or 13 (e.g., SEQ ID NO: 1), wherein 1 to 50, such as 1 to 40, 1 to 35, 1 to 30, 1 to 25, 1 to 20, 1 to 15, 1 to 10, 1 to 5, 1 to 3, amino acid residues are substituted, deleted and/or inserted.

Recombinant host cells in accordance with the invention can be produced from any suitable host organism, including single-celled or multicellular microorganisms such as bacteria, yeast, fungi and algae.

According to certain other embodiments, a recombinant host cells in accordance with the invention is selected from the group consisting of bacteria, yeast, fungi, and algae.

According to certain other embodiments, a recombinant host cells in accordance with the invention is selected from the group consisting of bacteria, yeast and fungi.

According to certain other embodiments, a recombinant host cells in accordance with the invention is selected from the group consisting of bacteria and yeast.

Bacterial host cells are selected from Gram-positive and Gram-negative bacteria. Non-limiting examples for Gram-negative bacterial host cells include species from the genera *Escherichia*, *Erwinia*, *Klebsiella* and *Citrobacter*. Non-limiting examples of Gram-positive bacterial host cells include species from the genera *Bacillus*, *Lactococcus*, *Lactobacillus*, *Clostridium*, *Corynebacterium*, *Streptomyces*, *Streptococcus*, and *Cellulomonas*.

According to certain embodiments, the recombinant host cell is a bacterium, which may be a bacterium of the genus *Bacillus*, *Lactococcus*, *Lactobacillus*, *Clostridium*, *Corynebacterium*, *Geobacillus*, *Thermoanaerobacterium*, *Streptococcus*, *Pseudomonas*, *Streptomyces*, *Escherichia*, *Shigella*, *Acinetobacter*, *Citrobacter*, *Salmonella*, *Klebsiella*, *Enterobacter*, *Erwinia*, *Kluyvera*, *Serratia*, *Cedecea*, *Morganella*, *Hafnia*, *Edwardsiella*, *Providencia*, *Proteus*, or *Yersinia*.

According to particular embodiments, the recombinant host cell is a bacterium of the genus *Bacillus*. Non-limiting examples of a bacterium of the genus *Bacillus* are *Bacillus subtitlis*, *Bacillus amyloliquefaciens*, *Bacillus licheniformis*, and *Bacillus mojavensis*. According to more particular embodiments, the recombinant host cell is *Bacillus subtitlis*. According to other more particular embodiments, the recombinant host cell is *Bacillus licheniformis*.

According to other particular embodiments, the recombinant host cell is a bacterium of the genus *Lactococcus*. A non-limiting example of a bacterium of the genus *Lactococcus* is *Lactococcus lactis*. According to more particular embodiments, the recombinant host cell is *Lactococcus lactis*.

According to other particular embodiments, the recombinant host cell is a bacterium of the genus *Corynebacterium*. A non-limiting example of a bacterium of the genus *Corynebacterium* is *Corynebacterium glutamicum*. According to more particular embodiments, the recombinant host cell is *Corynebacterium glutamicum*.

According to other particular embodiments, the recombinant host cell is a bacterium of the genus *Streptomyces*. Non-limiting examples of a bacterium of the genus *Streptomyces* are *Streptomyces lividans*, *Streptomyces coelicolor*, or *Streptomyces griseus*. According to more particular embodiments, the recombinant host cell is *Streptomyces lividans*. According to other more particular embodiments, the recombinant host cell is *Streptomyces coelicolor*. According to other more particular embodiments, the recombinant host cell is *Streptomyces griseus*.

According to other particular embodiments, the recombinant host cell is a bacterium of the genus *Pseudomonas*. A non-limiting example of a bacterium of the genus *Pseudomonas* is *Pseudomonas putida*. According to more particular embodiments, the recombinant host cell is *Pseudomonas putida*.

According to other particular embodiments, the recombinant host cell is a bacterium of the genus *Geobacillus*. A non-limiting examples of a bacterium of the genus *Geobacillus* are *Geobacillus thermoglucosidasius* and *Geobacillus stearothermophilus*. According to more particular embodiments, the recombinant host cell is *Geobacillus thermoglucosidasius*. According to other more particular embodiments, the recombinant host cell is *Geobacillus stearothermophilus*.

According to other particular embodiments, the recombinant host cell is a bacterium of the genus *Thermoanaerobacterium*. A non-limiting example of a bacterium of the genus *Pseudomonas* is *Thermoanaerobacterium thermosaccharolyticum*. According to more particular embodiments, the recombinant host cell is *Thermoanaerobacterium thermosaccharolyticum*.

According to other particular embodiments, the recombinant host cell is a bacterium of the genus *Escherichia*. A non-limiting example of a bacterium of the genus *Escherichia* is *Escherichia coli*. According to more particular embodiments, the recombinant host cell is *Escherichia coli*.

Yeast host cells may be derived from e.g., *Saccharomyces, Pichia, Schizosacharomyces, Zygosaccharomyces, Hansenula, Pachyosolen, Kluyveromyces, Debaryomyces, Yarrowia, Candida, Cryptococcus, Komagataella, Lipomyces, Rhodospiridium, Rhodotorula*, or *Trichosporon*.

According to certain embodiments, the recombinant host cell is a yeast, which may be a yeast is of the genus *Saccharomyces, Pichia, Schizosacharomyces, Zygosaccharomyces, Hansenula, Pachyosolen, Kluyveromyces, Debaryomyces, Yarrowia, Candida, Cryptococcus, Komagataella, Lipomyces, Rhodospiridium, Rhodotorula*, or *Trichosporon*.

According to particular embodiments, the recombinant host cell is a yeast of the genus *Saccharomyces*. A non-limiting example of a yeast of the genus *Saccharomyces* is *Saccharomyces cerevisiae*. According to more particular embodiments, the recombinant host cell is *Saccharomyces cerevisiae*.

According to particular embodiments, the recombinant host cell is a yeast of the genus *Pichia*. Non-limiting example of a yeast of the genus *Pichia* are *Pichia pastoris* and *pichia kudriavzevii*. According to more particular embodiments, the recombinant host cell is *Pichia pastoris*. According to other more particular embodiments, the recombinant host cell is *pichia kudriavzevii*.

Fungi host cells may be derived from, e.g., *Aspergillus*.

According to certain embodiments, the recombinant host cell is a fungus, such as a fungi of the genus *Aspergillus*. Non-limiting examples of a fungus of the genus *Aspergillus* are *Aspergillus Oryzae, Aspergillus niger* or *Aspergillus awamsii*. According to more particular embodiments, the recombinant host cell is *Aspergillus Oryzae*. According to other more particular embodiments, the recombinant host cell is *Aspergillus niger*. According to other more particular embodiments, the recombinant host cell is *Aspergillus awamsii*.

Algae host cells may be derived from, e.g., *Chlamydomonas, Haematococcus, Phaedactylum, Volvox* or *Dunaliella*.

According to certain embodiments, the recombinant host cell is an alga, which may be an algae of the genus *Chlamydomonas, Haematococcus, Phaedactylum, Volvox* or *Dunaliella*.

According to particular embodiments, the recombinant host cell is an alga cell of the genus *Chlamydomonas*. A non-limiting example of an alga of the genus *Chlamydomonas* is *Chlamydomonas reinhardtii*.

According to particular embodiments, the recombinant host cell is an alga cell of the genus *Haematococcus*. A non-limiting example of an alga of the genus *Haematococcus* is *Haematococcus pluvialis*.

According to other particular embodiments, the recombinant host cell is an alga cell of the genus *Phaedactylum*. A non-limiting example of an alga of the genus *Phaedactylum* is *Phaedactylum tricornatum*.

Generally, a recombinant host cell according to the invention has been genetically modified to express one or more polypeptides as detailed herein, which means that one or more exogenous nucleic acid molecules, such as DNA molecules, which comprise(s) a nucleotide sequence or nucleotide sequences encoding said polypeptide or polypeptides has been introduced in the host cell. Techniques for introducing exogenous nucleic acid molecule, such as a DNA molecule, into the various host cells are well-known to those of skill in the art, and include transformation (e.g., heat shock or natural transformation), transfection, conjugation, electroporation, microinjection and microparticle bombardment.

Accordingly, a recombinant host cell according to the invention comprises an exogenous nucleic acid molecule comprising a nucleotide sequence encoding a polypeptide as detailed herein.

In order to facilitate expression of the polypeptide in the host cell, the exogenous nucleic acid molecule may comprise suitable regulatory elements such as a promoter that is functional in the host cell to cause the production of an mRNA molecule and that is operably linked to the nucleotide sequence encoding said polypeptide.

Promoters useful in accordance with the invention are any known promoters that are functional in a given host cell to cause the production of an mRNA molecule. Many such promoters are known to the skilled person. Such promoters include promoters normally associated with other genes, and/or promoters isolated from any bacteria, yeast, fungi, alga or plant cell. The use of promoters for protein expression is generally known to those of skilled in the art of moleculer biology, for example, see Sambrook et al., Molecular cloning: A Laboratory Manual, Cold Spring Harbor Laboratory, Cold Spring Harbor, N.Y., 1989. The promoter employed may be inducible. The term "inducible" used in the context of a promoter means that the promoter only directs transcription of an operably linked nucleotide sequence if a stimulus is present, such as a change in temperature or the presence of a chemical substance ("chemical inducer"). As used herein, "chemical induction" according to the present invention refers to the physical application of a exogenous or endogenous substance (incl. macromolecules, e.g., proteins or nucleic acids) to a host cell. This has the effect of causing the target promoter present in the host cell to increase the rate of transcription. Alternatively, the promoter employed may be constitutive. The term "constitutive" used in the context of a promoter means that the promoter is capable of directing transcription of an operably linked nucleotide sequence in the absence of stimulus (such as heat shock, chemicals etc.).

Non-limiting examples of promoters functional in bacteria, such as *Bacillus subtilis, Lactococcus lactis* or *Escherichia coli*, include both constitutive and inducible promoters such as T7 promoter, the beta-lactamase and lactose promoter systems; alkaline phosphatase (phoA) promoter, a tryptophan (trp) promoter system, tetracycline promoter, lambda-phage promoter, ribosomal protein promoters; and hybrid promoters such as the tac promoter. Other bacterial and synthetic promoters are also suitable.

Non-limiting examples of promoters functional in yeast, such as *Saccharomyces cerevisiae*, include xylose promoter, GAL1 and GAL10 promoters, TEF1 promoter, and pgk1 promoter.

Non-limiting examples of promoters functional in fungi, such as *Aspergillus Oryzae* or *Aspergillus niger*, include promotors derived from the gene encoding *Aspergillus oryzae* TAKA amylase, *Aspergillus niger* neutral α-amylase,

*Aspergillus niger* acid stable α-amylase, *Aspergillus niger* or *Aspergillus awamsii* glucoamylase (gluA), *Aspergillus niger* acetamidase, *Aspergillus oryzae* alkaline protease, *Aspergillus oryzae* triose phosphatase isomerase, *Rhizopus meihei* aspartic proteinase, and *Rhizopus meihei* lipase.

Non-limiting examples of promoters functional in alga, such as *Haematococcus pluvialis*, include the CaMV35S promoter, the SV40 promoter, and promoter of the *Chlamydomonas reinhardtii* RBCS2 gene and the promoter of the *Volvox carteri* ARS gene.

Non-limiting examples of promoters functional in plant cells include the *Lactuca sative* psbA promoter, the tabacco psbA promoter, the tobacco rrn16 PEP+NEP promoter, the CaMV 35S promoter, the 19S promoter, the tomato E8 promoter, the nos promoter, the Mac promoter, and the pet E promoter or the ACT1 promoter.

Besides a promoter, the exogenous nucleic acid molecule may further comprise at least one regulatory element selected from a 5' untranslated region (5' UTR) and 3' untranslated region (3' UTR). Many such 5' UTRs and 3' UTRs derived from prokaryotes and eukaryotes are well known to the skilled person. Such regulatory elements include 5' UTRs and 3' UTRs normally associated with other genes, and/or 5' UTRs and 3' UTRs isolated from any bacteria, yeast, fungi, alga or plant cell.

If the host cell is a prokaryotic organism, the 5' UTR usually contains a ribosome binding site (RBS), also known as the Shine Dalgarno sequence which is usually 3-10 base pairs upstream from the initiation codon. Meanwhile, if the host cell is an eukaryotic organism the 5' UTR usually contains the Kozak consensus sequence. An eukaryotic 5' UTR may also contain cis-acting regulatory elements.

The exogenous nucleic acid molecule may be a vector or part of a vector, such as an expression vector. Normally, such a vector remains extrachromosomal within the host cell which means that it is found outside of the nucleus or nucleoid region of the host cell.

According to certain embodiments, a recombinant host cell employed according to the invention does not express an endogenous PAPS-dependent aryl sulfotransferase.

It is also contemplated by the present invention that the exogenous nucleic acid molecule is stably integrated into the genome of the host cell. Means for stable integration into the genome of a host cell, e.g., by homologous recombination, are well known to the skilled person.

The sulfation reaction depends on the supply of sulfate from 3'-phosphoadenosine 5'-phosphosulfate (PAPS) or transferred from another sulfated compound. The inventors have shown that the sulfation reaction can be enhanced by improving the supply of PAPS (3'-phosphoadenosine 5'-phosphosulfate) and, in addition, by the removal of the product 3'-phosphoadenosine 5'-phosphate (PAP). The improved supply is obtained by deregulation, mutation or overexpression of enzymes that increase PAPS concentration or similarly reduce PAP concentration. This is exemplified in Example 2, where an increased production of zosteric acid in *Escherichia coli* is obtained by increasing the expression of the genes cysD, cysN, and cysC which are responsible for production of PAPS. Without being bound to a specific theory, it is believed that an adenylyl moiety (AMP) of ATP is transferred to sulfate to form activated sulfate, or APS (adenosine 5'-phosphosulfate). This extremely unfavorable reaction is kinetically and energetically linked to the hydrolysis of GTP by the enzyme ATP sulfurylase, which is composed of two types of subunits: an adenylyl transferase (cysD) and a GTPase (cysN). APS is then phosphorylated at the 3'-hydroxyl to form PAPS (3'-phosphoadenosine 5'-phosphosulfate) in a reaction catalysed by APS kinase, which is encoded by cysC. Furthermore, the inventors have enhanced the production of zosteric acid even more by increasing the expression of the gene cysQ encoding a PAP phosphatase which is responsible for the removal of PAP.

Therefore, in order to further improve the production of a sulfated phenolic compound, such as zosteric acid, a recombinant host cell according to the present invention may be further modified to have an increased protein expression of an ATP sulfurylase compared to an identical host cell that does not carry said modification; may be further modified to have an increased protein expression of an APS kinase compared to an identical host cell that does not carry said modification; and/or may be further modified to have an increased protein expression of a PAP phosphatase compared to an identical host cell that does not carry said modification. By "increased protein expression" it is meant that the amount of the respective protein produced by the thus modified host cell is increased compared an identical host cell that does not carry said modification. More particularly, by "increase expression" it is meant that the amount of respective protein produced by the thus modified host cell is increased by at least 10%, such as at least 20%, at least 30%, at least 40%, at least 50% at least 60%, at least 70%, at least 80%, at least 90%, at least 100%, at least 150%, at least 200%, at least 300%, at least 400%, at least 500%, at least 600%, at least 700% at least 800%, at least about 900%, at least about 1000%, at least about 2000%, at least about 3000%, at least about 4000%, at least about 5000%, at least about 6000%, at least about 7000%, at least about 8000% at least about 9000% or at least about 10000%, compared an identical host cell that does not carry said modification. The amount of protein in a given cell can be determined by any suitable quantification technique known in the art, such as ELISA, Immunohistochemistry or Western Blotting.

According to certain embodiments, a recombinant host cell employed according to the invention has further been modified to have an increased protein expression an ATP sulfurylase compared to an identical host cell that does not carry said modification.

According to certain embodiments, a recombinant host cell employed according to the invention has further been modified to have an increased protein expression of an APS kinase compared to an identical host cell that does not carry said modification.

According to certain embodiments, a recombinant host cell according to the invention has further been modified to have an increased protein expression of a PAP phosphatase compared to an identical host cell that does not carry said modification.

An increase in protein expression may be achieved by any suitable means well-known to those skilled in the art. For example, an increase in protein expression may be achieved by increasing the number of copies of the gene or genes encoding the respective protein (e.g., ATP sulfurylase, APS kinase and/or PAP phosphatase) in the host cell, such as by using (e.g., introducing into the host cell) a vectors comprising the gene or genes operably linked to a promoter that is functional in the host cell to cause the production of an mRNA molecule. An increase in protein expression may also be achieved by integration of at least a second copy of the gene or genes encoding the respective protein into the genome of the host cell. An increase in protein expression may also be achieved by increasing the strength of the promoter(s) operably linked to the gene or genes. An increase in protein expression may also be achieved by modifying the ribosome binding site on the mRNA molecule encoding the respective protein (e.g., ATP sulfurylase, APS kinase and/or PAP phosphatase). By modifying the sequence of the ribosome binding site the translation initiation rate may be increased, thus increasing the translation efficiency.

ATP sulfurylase encoding genes for use according to the invention may for instance be the cysD and cysN genes from *Escherichia coli* (encoding SEQ ID NO: 15 and 16, respectively). Alternative ATP sulfurylase encoding genes include the Arabidopsis thaliana ATP sulfurylase ASAL gene (Gen-Bank Accession No. U40715, Logan et al. (1996) J Biol Chem 271: 12227); the Allium cepa ATP-sulfurylase gene (Gen-Bank Accession No AF21154); the Lotus japonicus ATP sulfurylase gene (GenBank Accession No. AW164083); the Arabidopsis thaliana met3-1 ATP sulfurylase gene (Gen-Bank Accession No. X79210).

According to certain embodiments, a recombinant host cell according to the invention comprises an exogenous nucleic acid molecule (such as a vector) comprising one or more nucleotide sequences encoding a ATP sulfurylase.

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 15 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 15, provide that the sequence identity is not 100%, and a nucleotide sequence encoding iii) a polypeptide comprising an amino acid sequence set forth in SEQ ID NO: 16 or iv) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 16, provide that the sequence identity is not 100%. Preferably, the polypeptides assemble to form a protein having ATP sulfurylase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 15 and a nucleotide sequence encoding a polypeptide comprising an amino acid sequence set forth in SEQ ID NO: 16.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 15, provide that the sequence identity is not 100%, and a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 16, provide that the sequence identity is not 100%. Preferably, the polypeptides assemble to form a protein having ATP sulfurylase activity.

According to particular embodiments, a recombinant host cell according to the invention comprises an exogenous nucleic acid molecule (such as vector) comprising a nucleotide sequence encoding a polypeptide comprising an amino acid sequence which has at least about about 85%, such as at least about 90%, at least about 93%, at least 95%, at least 96%, at least 97%, at least 98%, or at least 99%, sequence identity to the amino acid sequence set forth in SEQ ID NO: 15, provide that the sequence identity is not 100%, and a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 16, provide that the sequence identity is not 100%. Preferably, the polypeptides assemble to form a protein having ATP sulfurylase activity.

An alternative ATP sulfurylase encoding gene for use according to the invention may for instance be the MET3 gene from *Saccharomyces cerevisiae* (encoding SEQ ID NO: 46).

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 46 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 46. Preferably, the polypeptide according to ii) has ATP sulfurylase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 46.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 46. Preferably, the polypeptide has ATP sulfurylase activity.

According to particular embodiments, a recombinant host cell according to the invention comprises an exogenous nucleic acid molecule (such as vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 46. Preferably, the polypeptide has ATP sulfurylase activity.

In order to facilitate expression of the polypeptides in the host cell, the exogenous nucleic acid molecule may comprise suitable regulatory elements such as a promoter that is functional in the host cell to cause the production of an mRNA molecule and that is operably linked to the nucleotide sequences encoding said polypeptides.

An APS kinase encoding gene for use according to the invention may for instance be the cysC gene from *Escherichia coli* (encoding SEQ ID NO: 17).

In certain instances a single polypeptide has been shown to possess both an ATP sulfurylase and a 5'-adenylylsulfate kinase activity. For example, an ATP sulfurylase/APS kinase encoding gene has been isolated from mouse (GenBank Accession No. U34883, Li et al. (1995) J Biol Chem)70: 1945), and human (GenBank Accession No. AF033026, Yanagisawa (1998) Biosci Biotechnol Biochem 62: 1037) sources.

According to certain embodiments, a recombinant host cell according to the invention comprises an exogenous nucleic acid molecule (such as a vector) comprising a nucleotide sequence encoding an APS kinase.

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 17 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 17, provide that the sequence identity is not 100%. Preferably, said polypeptide according to ii) has APS kinase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 17.

According to particular embodiments, a recombinant host cell according to the invention comprises an exogenous nucleic acid molecule (such vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 17, provide that the sequence identity is not 100%. Preferably, said polypeptide has APS kinase activity.

According to particular embodiments, a recombinant host cell according to the invention comprises an exogenous nucleic acid molecule (such vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 17, provide that the sequence identity is not 100%. Preferably, said polypeptide has APS kinase activity.

An alternative APS kinase encoding gene for use according to the invention may for instance be the MET14 gene from *Saccharomyces cerevisiae* (encoding SEQ ID NO: 47).

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 47 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 47. Preferably, said polypeptide according to ii) has APS kinase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 47.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 47. Preferably, said polypeptide has APS kinase activity.

According to particular embodiments, a recombinant host cell according to the invention comprises an exogenous nucleic acid molecule (such as vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 47. Preferably, said polypeptide has APS kinase activity.

In order to facilitate expression of the polypeptide in the host cell, the exogenous nucleic acid molecule may comprise suitable regulatory elements such as a promoter that is functional in the host cell to cause the production of an mRNA molecule and that is operably linked to the nucleotide sequence encoding said polypeptide.

An PAP phosphatase encoding gene for use according to the invention may for instance be the cysQ gene from *Escherichia coli* (encoding SEQ ID NO: 18).

According to certain embodiments, a recombinant host cell according to the invention comprises an exogenous nucleic acid molecule (such as a vector) comprising a nucleotide sequence encoding an PAP phosphatase.

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 18 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 18, provide that the sequence identity is not 100%. Preferably, said polypeptide according to ii) has PAP phosphatase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 18.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 18, provide that the sequence identity is not 100%. Preferably, said polypeptide has PAP phosphatase activity.

According to particular embodiments, a recombinant host cell according to the invention comprises an exogenous nucleic acid molecule (such as vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 18, provide that the sequence identity is not 100%. Preferably, said polypeptide has PAP phosphatase activity.

An alternative PAP phosphatase encoding gene for use according to the invention may for instance be the MET22 gene from *Saccharomyces cerevisiae* (encoding SEQ ID NO: 48).

According to particular embodiments, a recombinant host cell according to the invention comprises an exogenous nucleic acid molecule (such as a vector) comprising a nucleotide sequence encoding i) a polypeptide comprising an amino acid sequence set forth in SEQ ID NO: 48 or ii) a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 48. Preferably, said polypeptide according to ii) has PAP phosphatase activity.

According to particular embodiments, a recombinant host cell according to the invention comprises an exogenous nucleic acid molecule (such as a vector) comprising a nucleotide sequence encoding a polypeptide comprising an amino acid sequence set forth in SEQ ID NO: 48.

According to particular embodiments, a recombinant host cell according to the invention comprises an exogenous nucleic acid molecule (such as vector) comprising a nucleotide sequence encoding a polypeptide comprising an amino acid sequence which has at least about 70%, such as at least about 75%, at least about 80%, at least about 85%, at least about 90%, at least about 93%, at least 95%, at least 96%, at least 97%, at least 98%, or at least 99%, sequence identity to the amino acid sequence set forth in SEQ ID NO: 48. Preferably, said polypeptide has PAP phosphatase activity.

According to particular embodiments, a recombinant host cell according to the invention comprises an exogenous nucleic acid molecule (such as vector) comprising a nucleotide sequence encoding a polypeptide comprising an amino acid sequence which has at least about 85%, such as at least about 90%, at least about 93%, at least 95%, at least 96%, at least 97%, at least 98%, or at least 99%, sequence identity to the amino acid sequence set forth in SEQ ID NO: 48. Preferably, said polypeptide has PAP phosphatase activity.

In order to facilitate expression of the polypeptide in the host cell, the exogenous nucleic acid molecule may comprise suitable regulatory elements such as a promoter that is functional in the host cell to cause the production of an mRNA molecule and that is operably linked to the nucleotide sequence encoding said polypeptide.

The sulfating step (c) may be carried out during or after the pre-treatment step (a) and/or during or after the hydrolysis step (b). According to certain embodiments, sulfating step (c) is carried out after the pre-treatment step (a). According to certain embodiments, sulfating step (c) is carried out after the hydrolysis step (b). According to certain embodiments, sulfating step (c) is carried out after the pre-treatment step (a) and after the hydrolysis step (b). According to certain embodiments, the pre-treatment step (a) and the sulfating step (c) are carried out simultaneously. According to certain embodiments, hydrolysis step (b) and the sulfating step (c) are carried out simultaneously. According to certain embodiments, the pre-treatment step (a), the hydrolysis step (b) and the sulfating step (c) are carried out simultaneously.

Suitable sulfate donor molecules metabolized by a polypeptide having aryl sulfotransferase activity are well-known to one skilled in the art. Non-limiting examples include 3'-phosphoadenosine 5'-phosphosulfate (PAPS), para-nitrophenyl sulfate (pNPS) and 4-methylumbelliferyl sulfate (MUS). Such sulfate donor molecules may be employed to facilitate the sulfation of phenolic compounds in accordance with the invention.

The medium employed for culturing the recombinant host cell may be any conventional medium suitable for culturing the host cell in question, and may be composed according to the principles of the prior art. The medium will usually contain all nutrients necessary for the growth and survival of the respective host cell, such as carbon and nitrogen sources and other inorganic salts, such as sulfate salts. Suitable media, e.g. minimal or complex media, are available from commercial suppliers, or may be prepared according to published receipts, e.g. the American Type Culture Collection (ATCC) Catalogue of strains. Non-limiting standard medium well known to the skilled person include Luria Bertani (LB) broth, Sabouraud Dextrose (SD) broth, MS broth, Yeast Peptone Dextrose, BMMY, GMMY, or Yeast Malt Extract (YM) broth, which are all commercially available. A non-limiting example of suitable media for culturing bacterial cells, such as *B. subtilis, L. lactis* or *E. coli* cells, including minimal media and rich media such as Luria Broth (LB), M9 media, M17 media, SA media, MOPS media, Terrific Broth, YT and others. Suitable media for culturing eukaryotic cells, such as yeast cells, are RPMI 1640, MEM, DMEM, all of which may be supplemented with serum and/or growth factors as required by the particular host cell being cultured. The medium for culturing eukaryotic cells may also be any kind of minimal media such as Yeast minimal media.

The hydrolyzed product obtained in accordance to the process as described above may be further fermented to obtain a fermentation product.

Therefore, present invention provides in a further aspect a process for the production of a fermentation product, from a lignocellulose-containing material, comprising the steps:
(a) pre-treating a lignocellulose-containing material;
(b) hydrolyzing the pre-treated lignocellulose-containing material to form a hydrolyzate;
(c) enzymatically sulfating phenolic compounds produced during step a) and/or step b).
(d) fermenting the hydrolyzate obtained in step (b) using a fermenting organism, thereby obtaining a fermentation product.

It is to be understood that the details given above in the context of the first aspect, in particular with respect to steps (a), (b) and (c), apply mutatis mutandis to this further aspect.

According to this further aspect of the invention, the pre-treated and hydrolyzed lignocellulose-containing material (the hydrolyzate) is fermented by at least one fermenting organism capable of fermenting fermentable sugars, such as glucose, xylose, mannose, and galactose directly or indirectly into a desired fermentation product.

Suitable process time, temperature and pH conditions for the fermentation are well-known to one skilled in the art. For example, fermentation may be carried out at a temperature in the range from about 20° C. to about 80° C., such as from about 20° C. to about 70° C., from about 20° C. to about 60° C., from about 20° C. to about 50° C., from about 20° C. to about 40° C., from about 20° C. to about 37° C. from about 25° C. to about 60° C., from about 25° C. to about 50° C., from about 25° C. to about 40° C. or from about 25° C. to about 37° C. According to certain embodiments, the fermentation is carried out at a temperature in the range from about 25° C. to about 40° C. According to certain embodiments, the fermentation is carried out at a temperature in the range from about 60° C. to about 80° C.

Fermentation may, for example, be carried out at a pH ranging from about pH 1 to about pH 9, but will normally range from about pH 5.0 to about pH 9.0, such as from about pH 5.5 to about pH 8.0, such as from about pH 6 to about 7.5, such as from about pH 6.5 to about pH 7, such as at about pH 6 or pH 7. According to certain embodiments, the fermentation is carried out at a pH ranging from about pH 5.5 to about pH 8.0. According to certain other embodiments, the fermentation is carried out at a pH ranging from about pH 6 to about pH 8, such as from about pH 6.5 to about pH 7.5.

Fermentation may, for example, be carried out for at least about 4 hours, such as for at least about 8 hours, at least about 12 hours, at least about 18 hours, at least about 24 hours, at least about 48 hours, at least about 72 hours, at least about 96 hours, at least about one week, at least about two weeks, at least about one month or at least about 3 months. According to certain embodiments, the fermentation is carried out for at least about 8 hours.

The hydrolysis step (b), the sulfating step (c), and the fermentation step (d) may be carried out simultaneously, sequentially, or as a hybrid. According to certain embodiments, hydrolysis step (b), sulfating step (c) and fermentation step (d) are carried out sequentially. According to certain embodiments, hydrolysis step (b), sulfating step (c) and fermentation step (d) are carried out simultaneously.

According to certain embodiments, sulfating step (c) is performed simultaneously with fermentation step (d). According to particular embodiments, the fermenting organism employed in step (d) is a recombinant host cell as detailed herein. In this case, fermenting organism not only expresses a polypeptide having aryl sulfotransferase activity, but also converts fermentable sugars, such as glucose, xylose, mannose, and galactose directly or indirectly into a desired fermentation product.

According to certain other embodiments, hydrolysis step (b) and fermentation step (d) are carried out as a separate hydrolysis and fermentation, where the hydrolysis is taken to completion before initiation of fermentation. This is often referred to as "SHF".

According to certain other embodiments, hydrolysis step (b) and fermentation step (d) are carried out as a simultaneous hydrolysis and fermentation, where the fermentation takes place while the pre-treated pre-treated lignocellulose-containing material is hydrolyzed. In general this means that a simultaneous hydrolysis and fermentation is carried out at conditions (e.g., temperature and/or pH) suitable, preferably optimal, for the fermenting organism(s) in question. When the fermentation (e.g., ethanol fermentation using, e.g., a Saccharomyces yeast) is performed simultaneously with hydrolysis, the temperature is suitably in the range from about 26° C. to about 35° C., such as from about 30° C. to 34° C., such as at about 32° C. However, higher temperatures, such as in the range from about 60° C. to about 80° C., are also envisioned if the fermenting organism is a thermophile.

According to certain other embodiments, hydrolysis step (b) and fermentation step (d) are carried out as hybrid hydrolysis and fermentation (HHF), which is a combination of the SHF and SSF processes. HHF typically begins with a separate partial hydrolysis step and ends with a simultaneous hydrolysis and fermentation step. The separate partial hydrolysis step is an enzymatic cellulose saccharification step typically carried out at conditions (e.g., at higher temperatures) suitable, preferably optimal, for the hydrolyzing enzyme(s) in question. The subsequent simultaneous hydrolysis and fermentation step is typically carried out at conditions suitable for the fermenting organism(s) (often at lower temperatures than the separate hydrolysis step).

One or more cellulolytic enzymes as detailed above may be employed in the fermentation step (d). Likewise, one or more hemicellulolytic enzymes as detailed above may be employed in the fermentation step (d).

Subsequent to fermentation the fermentation product may be separated from the fermentation medium/broth. The medium/broth may be distilled to extract the fermentation product or the fermentation product may be extracted from the fermentation medium/broth by micro or membrane filtration techniques. Alternatively, the fermentation product may be recovered by stripping. Recovery methods are well known in the art.

Especially contemplated fermentation products include, but are not limited to, alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones. Other, non-limiting examples of fermentation products are diamines, diols, triols, carboxylic acids, diacids, aromatic acids, dienes and isoprenoids.

According to certain embodiments, the fermentation product obtained in accordance with the invention is an alcohol, especially ethanol. The fermentation product, such as ethanol, obtained according to the invention, may preferably be fuel alcohol/ethanol. However, in the case of ethanol it may also be used as potable ethanol.

According to certain other embodiments, the fermentation product obtained in accordance with the invention is an organic acid.

According to certain other embodiments, the fermentation product obtained in accordance with the invention is a ketone.

According to certain other embodiments, the fermentation product obtained in accordance with the invention is an amino acid.

According to certain other embodiments, the fermentation product obtained in accordance with the invention is a diamine.

According to certain other embodiments, the fermentation product obtained in accordance with the invention is a diol.

According to certain other embodiments, the fermentation product obtained in accordance with the invention is a triol.

According to certain other embodiments, the fermentation product obtained in accordance with the invention is a carboxylic acid.

According to certain other embodiments, the fermentation product obtained in accordance with the invention is a diacid.

According to certain other embodiments, the fermentation product obtained in accordance with the invention is an aromatic acid.

The term "fermenting organism" as used herein refers to any organism, including bacterial and fungal organisms, suitable for producing a desired fermentation product. Especially suitable fermenting organisms according to the invention are able to ferment, i.e., convert, sugars, such as glucose, directly or indirectly into the desired fermentation product.

Examples of fermenting organisms include bacteria, yeast, fungi and algae.

According to certain embodiments, a fermenting organism in accordance with the invention is selected from the group consisting of bacteria, yeast, fungi, algae and plant.

According to certain other embodiments, a fermenting organism in accordance with the invention is selected from the group consisting of bacteria, yeast, fungi, and algae.

According to certain other embodiments, a fermenting organism in accordance with the invention is selected from the group consisting of bacteria, yeast and fungi.

According to certain other embodiments, a fermenting organism in accordance with the invention is selected from the group consisting of bacteria and yeast.

Bacterial host cells are selected from Gram-positive and Gram-negative bacteria. Non-limiting examples for Gram-negative bacterial host cells include species from the genera *Escherichia, Erwinia, Klebsiella* and *Citrobacter*. Non-limiting examples of Gram-positive bacterial host cells include species from the genera *Bacillus, Lactococcus, Lactobacillus, Clostridium, Corynebacterium, Streptomyces, Streptococcus*, and *Cellulomonas*.

According to certain embodiments, the fermenting organism is a bacterium, which may be a bacterium of the genus *Bacillus, Lactococcus, Lactobacillus, Clostridium, Corynebacterium, Geobacillus, Thermoanaerobacterium, Streptococcus, Pseudomonas, Streptomyces, Escherichia, Shigella, Acinetobacter, Citrobacter, Salmonella, Klebsiella, Enterobacter, Erwinia, Kluyvera, Serratia, Cedecea, Morganella, Hafnia, Edwardsiella, Providencia, Proteus*, or *Yersinia*.

According to particular embodiments, the fermenting organism is a bacterium of the genus *Bacillus*. Non-limiting examples of a bacterium of the genus *Bacillus* are *Bacillus subtitlis, Bacillus amyloliquefaciens, Bacillus licheniformis*, and *Bacillus mojavensis*. According to more particular embodiments, the fermenting organism is *Bacillus subtitlis*. According to other more particular embodiments, the fermenting organism is *Bacillus licheniformis*.

According to other particular embodiments, the fermenting organism is a bacterium of the genus *Lactococcus*. A non-limiting example of a bacterium of the genus *Lactococcus* is *Lactococcus lactis*. According to more particular embodiments, the fermenting organism is *Lactococcus lactis*.

According to other particular embodiments, the fermenting organism is a bacterium of the genus *Corynebacterium*. A non-limiting example of a bacterium of the genus *Corynebacterium* is *Corynebacterium glutamicum*. According to more particular embodiments, the fermenting organism is *Corynebacterium glutamicum*.

According to other particular embodiments, the fermenting organism is a bacterium of the genus *Streptomyces*. A non-limiting examples of a bacterium of the genus *Streptomyces* are *Streptomyces lividans, Streptomyces coelicolor*, or *Streptomyces griseus*. According to more particular embodiments, the fermenting organism is *Streptomyces lividans*. According to other more particular embodiments, the fermenting organism is *Streptomyces coelicolor*. According to other more particular embodiments, the fermenting organism is *Streptomyces griseus*.

According to other particular embodiments, the fermenting organism is a bacterium of the genus *Pseudomonas*. A non-limiting example of a bacterium of the genus *Pseudomonas* is *Pseudomonas putida*. According to more particular embodiments, the fermenting organism is *Pseudomonas putida*.

According to other particular embodiments, the fermenting organism is a bacterium of the genus *Geobacillus*. A non-limiting examples of a bacterium of the genus *Geobacillus* are *Geobacillus thermoglucosidasius* and *Geobacillus stearothermophilus*. According to more particular embodiments, the fermenting organism is *Geobacillus thermoglucosidasius*. According to other more particular embodiments, the fermenting organism is *Geobacillus stearothermophilus*.

According to other particular embodiments, the fermenting organism is a bacterium of the genus *Thermoanaerobacterium*. A non-limiting example of a bacterium of the genus *Pseudomonas* is *Thermoanaerobacterium thermosaccharolyticum*. According to more particular embodiments, the fermenting organism is *Thermoanaerobacterium thermosaccharolyticum*.

According to other particular embodiments, the fermenting organism is a bacterium of the genus *Escherichia*. A non-limiting example of a bacterium of the genus *Escherichia* is *Escherichia coli*. According to more particular embodiments, the fermenting organism is *Escherichia coli*.

Yeast host cells may be derived from e.g., *Saccharomyces, Pichia, Schizosacharomyces, Zygosaccharomyces, Hansenula, Pachyosolen, Kluyveromyces, Debaryomyces, Yarrowia, Candida, Cryptococcus, Komagataella, Lipomyces, Rhodospiridium, Rhodotorula*, or *Trichosporon*.

According to certain embodiments, the fermenting organism is a yeast, which may be a yeast is of the genus *Saccharomyces, Pichia, Schizosacharomyces, Zygosaccharomyces, Hansenula, Pachyosolen, Kluyveromyces, Debaryomyces, Yarrowia, Candida, Cryptococcus, Komagataella, Lipomyces, Rhodospiridium, Rhodotorula*, or *Trichosporon*.

According to particular embodiments, the fermenting organism is a yeast of the genus *Saccharomyces*. A non-limiting example of a yeast of the genus *Saccharomyces* is *Saccharomyces cerevisiae*. According to more particular embodiments, the fermenting organism is *Saccharomyces cerevisiae*.

According to particular embodiments, the fermenting organism is a yeast of the genus *Pichia*. Non-limiting example of a yeast of the genus *Pichia* are *Pichia pastoris* and *pichia kudriavzevii*. According to more particular embodiments, the fermenting organism is *Pichia pastoris*. According to other more particular embodiments, the fermenting organism is *pichia kudriavzevii*.

Fungi host cells may be derived from, e.g., *Aspergillus*.

According to certain embodiments, the fermenting organism is a fungus, such as a fungi of the genus *Aspergillus*. Non-limiting examples of a fungus of the genus *Aspergillus* are *Aspergillus Oryzae, Aspergillus niger* or *Aspergillus awamsii*. According to more particular embodiments, the fermenting organism is *Aspergillus Oryzae*. According to other more particular embodiments, the fermenting organism is *Aspergillus niger*. According to other more particular embodiments, the fermenting organism is *Aspergillus awamsii*.

Algae host cells may be derived from, e.g., *Chlamydomonas, Haematococcus, Phaedactylum, Volvox* or *Dunaliella*.

According to certain embodiments, the fermenting organism is an alga, which may be an algae of the genus *Chlamydomonas, Haematococcus, Phaedactylum, Volvox* or *Dunaliella*.

According to particular embodiments, the fermenting organism is an alga cell of the genus *Chlamydomonas*. A non-limiting example of an alga of the genus *Chlamydomonas* is *Chlamydomonas reinhardtii*.

According to particular embodiments, the fermenting organism is an alga cell of the genus *Haematococcus*. A non-limiting example of an alga of the genus *Haematococcus* is *Haematococcus pluvialis*.

According to other particular embodiments, the fermenting organism is an alga cell of the genus *Phaedactylum*. A non-limiting example of an alga of the genus *Phaedactylum* is *Phaedactylum tricornatum*.

As mentioned above, the fermenting organism may a recombinant host cell as detailed herein.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the invention.

It should be noted that embodiments and features described in the context of one of the aspects of the present invention also apply to the other aspects of the invention.

Certain Other Definitions

"Aryl sulfotransferase activity" as used herein refers to the ability of a polypeptide to catalyze the transfer of a sulfate group from a donor molecule to an aryl acceptor molecule.

"ATP sulfurylase" as used herein refers to an enzyme that catalyzes the reaction: ATP+sulfate=diphosphate+adenosine 5'-phosphosulfate (APS).

"APS kinase" as used herein refers to an enzyme that catalyzes the reaction: ATP+adenosine 5'-phosphosulfate (APS)=ADP+3'-phosphoadenosine 5'-phosphosulfate (PAPS).

"PAP phosphatase" as used herein refers to an enzyme that catalyzes the reaction: 3'-phosphoadenosine 5'-phosphate (PAP)+$H_2O$=AMP+phosphate.

"Polypeptide," or "protein" are used interchangeably herein to denote a polymer of at least two amino acids covalently linked by an amide bond, regardless of length or post-transiational modification (e.g., glycosylation, phosphorylation, lipidation, myristilation, ubiquitination, etc.). Included within this definition are D- and L-amino acids, and mixtures of D- and L-amino acids.

"Nucleic acid" or "polynucleotide" are used interchangeably herein to denote a polymer of at least two nucleic acid monomer units or bases (e.g., adenine, cytosine, guanine, thymine) covalently linked by a phosphodiester bond, regardless of length or base modification.

"Recombinant" or "non-naturally occurring" when used with reference to, e.g., a host cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant host cells expressing genes that are not found within the native (non-recombinant) form of the cell or express native genes that are otherwise expressed at a different level.

"Substitution" or "substituted" refers to modification of the polypeptide by replacing one amino acid residue with another, for instance the replacement of an Arginine residue with a Glutamine residue in a polypeptide sequence is an amino acid substitution.

"Conservative substitution" refers to a substitution of an amino acid residue with a different residue having a similar side chain, and thus typically involves substitution of the amino acid in the polypeptide with amino acids within the same or similar class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having an aromatic side chain is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

"Non-conservative substitution" refers to substitution of an amino acid in a polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" or "deleted" refers to modification of the polypeptide by removal of one or more amino acids in the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered enzyme. Deletions can be directed to the internal portions and/or terminal portions of the polypeptide, in various embodiments, the deletion can comprise a continuous segment or can be discontinuous.

"Insertion" or "inserted" refers to modification of the polypeptide by addition of one or more amino acids to the reference polypeptide. Insertions can comprise addition of 1 or more amino acids, 2 or more amino acids, 5 or more amino acids, 10 or more amino acids, 15 or more amino acids, or 20 or more amino acids. Insertions can be in the internal portions of the polypeptide, or to the carboxy or amino terminus. The insertion can be a contiguous segment of amino acids or separated by one or more of the amino acids in the reference polypeptide.

"Host cell" as used herein refers to a living cell or microorganism that is capable of reproducing its genetic material and along with it recombinant genetic material that has been introduced into it—e.g., via heterologous transformation.

"Expression" includes any step involved in the production of a polypeptide (e.g., encoded enzyme) including, but not limited to, transcription, post-transcriptional modification, translation, post-translational modification, and secretion.

As used herein, "vector" refers to a nucleic acid molecule capable of transporting another nucleic acid molecule to which it has been linked. One type of vector is a "plasmid", which refers to a circular double stranded nucleic acid loop into which additional nucleic acid segments can be ligated. Certain vectors are capable of directing the expression of genes to which they are operatively linked. Such vectors are referred to herein as "expression vectors". Certain other vectors are capable of facilitating the insertion of an exogenous nucleic acid molecule into a genome of a host cell. Such vectors are referred to herein as "transformation vectors". In general, vectors of utility in recombinant nucleic acid techniques are often in the form of plasmids. In the present specification, "plasmid" and "vector" can be used interchangeably as the plasmid is the most commonly used form of a vector. Large numbers of suitable vectors are known to those of skill in the art and commercially available.

As used herein, "promoter" refers to a sequence of DNA, usually upstream (5') of the coding region of a structural gene, which controls the expression of the coding region by providing recognition and binding sites for RNA polymerase and other factors which may be required for initiation of transcription. The selection of the promoter will depend upon the nucleic acid sequence of interest. A "promoter functional in a host cell" refers to a "promoter" which is capable of supporting the initiation of transcription in said cell, causing the production of an mRNA molecule.

As used herein, "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence. A promoter sequence is "operably-linked" to a gene when it is in sufficient proximity to the transcription start site of a gene to regulate transcription of the gene.

"Percentage of sequence identity," "% sequence identity" and "percent identity" are used herein to refer to comparisons between an amino acid sequence and a reference amino acid sequence. The "% sequence identify", as used herein, is calculated from the two amino acid sequences as follows: The sequences are aligned using Version 9 of the Genetic Computing Group's GAP (global alignment program), using the default BLOSUM62 matrix (see below) with a gap open penalty of –12 (for the first null of a gap) and a gap extension penalty of –4 (for each additional null in the gap). After alignment, percentage identity is calculated by expressing the number of matches as a percentage of the number of amino acids in the reference amino acid sequence.

The following BLOSUM62 matrix is used:

| | Ala | Arg | Asn | Asp | Cys | Gln | Glu | Gly | His | Ile | Leu | Lys | Met | Phe | Pro | Ser | Thr | Trp | Tyr | Val |
|---|---|---|---|---|---|---|---|---|---|---|---|---|---|---|---|---|---|---|---|---|
| Ala | 4 | | | | | | | | | | | | | | | | | | | |
| Arg | –1 | 5 | | | | | | | | | | | | | | | | | | |
| Asn | –2 | 0 | 6 | | | | | | | | | | | | | | | | | |
| Asp | –2 | –2 | 1 | 6 | | | | | | | | | | | | | | | | |
| Cys | 0 | –3 | –3 | –3 | 9 | | | | | | | | | | | | | | | |
| Gln | –1 | 1 | 0 | 0 | –3 | 5 | | | | | | | | | | | | | | |
| Glu | –1 | 0 | 0 | 2 | –4 | 2 | 5 | | | | | | | | | | | | | |
| Gly | 0 | –2 | 0 | –1 | –3 | –2 | –2 | 6 | | | | | | | | | | | | |
| His | –2 | 0 | 1 | –1 | –3 | 0 | 0 | –2 | 8 | | | | | | | | | | | |
| Ile | –1 | –3 | –3 | –3 | –1 | –3 | –3 | –4 | –3 | 4 | | | | | | | | | | |
| Leu | –1 | –2 | –3 | –4 | –1 | –2 | –3 | –4 | –3 | 2 | 4 | | | | | | | | | |
| Lys | –1 | 2 | 0 | –1 | –3 | 1 | 1 | –2 | –1 | –3 | –2 | 5 | | | | | | | | |
| Met | –1 | –1 | –2 | –3 | –1 | 0 | –2 | –3 | –2 | 1 | 2 | –1 | 5 | | | | | | | |
| Phe | –2 | –3 | –3 | –3 | –2 | –3 | –3 | –3 | –1 | 0 | 0 | –3 | 0 | 6 | | | | | | |
| Pro | –1 | –2 | –2 | –1 | –3 | –1 | –1 | –2 | –2 | –3 | –3 | –1 | –2 | –4 | 7 | | | | | |
| Ser | 1 | –1 | 1 | 0 | –1 | 0 | 0 | 0 | –1 | –2 | –2 | 0 | –1 | –2 | –1 | 4 | | | | |
| Thr | 0 | –1 | 0 | –1 | –1 | –1 | –1 | –2 | –2 | –1 | –1 | –1 | –1 | –2 | –1 | 1 | 5 | | | |
| Trp | –3 | –3 | –4 | –4 | –2 | –2 | –3 | –2 | –2 | –3 | –2 | –3 | –1 | 1 | –4 | –3 | –2 | 11 | | |
| Tyr | –2 | –2 | –2 | –3 | –2 | –1 | –2 | –3 | 2 | –1 | –1 | –2 | –1 | 3 | –3 | –2 | –2 | 2 | 7 | |
| Val | 0 | –3 | –3 | –3 | –1 | –2 | –2 | –3 | –3 | 3 | 1 | –2 | 1 | –1 | –2 | –2 | 0 | –3 | –1 | 4 |

"Reference sequence" or "reference amino acid sequence" refers to a defined sequence to which another sequence is compared. In the context of the present invention a reference amino acid sequence may be an amino acid sequence set forth in SEQ ID NO: 1, 2, 3, 4, 5, 6, 7, 8, 9, 10, 11, 12 or 13.

Where a numerical limit or range is stated herein, the endpoints are included. Also, all values and sub ranges within a numerical limit or range are specifically included as if explicitly written out.

Having generally described this invention, a further understanding can be obtained by reference to certain specific examples, which are provided herein for purposes of illustration only, and are not intended to be limiting unless otherwise specified.

EXAMPLES

Example 1—Production of Zosteric Acid in *E. coli*

A range of aryl sulfotransferases including SULT1A1 *Rattus norvegicus* (SEQ ID NO: 1), SULT1A1 *Homo sapiens* (SEQ ID NO: 2), SULT1A1 *Equus caballus* (SEQ ID NO: 3), SULT1A1 *Sus scrofa domesticus* (SEQ ID NO: 4), SULT1A1 *Canis lupus familiaris* (SEQ ID NO: 5) and SULT1E1 *Gallus gallus domesticus* (SEQ ID NO: 6) were expressed in *Escherichia coli*. The respective genes encoding SEQ ID NO. 1, 3, 4, 5, and 6 were cloned amplified from liver tissue cDNA (Zyagen) by PCR using the primers listed in Table 1. The nucleotide sequence of the gene encoding SEQ ID NO: 2 was codon optimized for expression in *Escherichia coli* (GeneArt, Life Technologies) and amplified by PCR using the primers in Table 1. The pETDuet-1 plasmid was digested with restriction endonucleases NcoI and Sa/1. The PCR products were then individually cloned into the plasmid pETDuet-1 using the Gibson reaction (New England Biolabs). The resulting plasmids were transformed into BL21(DE3)pLysS (Life Technologies). FIG. 1 shows the plasmid map of the plasmid encoding SULT1A1 *Rattus norvegicus* (SEQ ID NO: 1).

TABLE 1

Overview of enzymes and primers for cloning aryl sulfotransferases

| SEQ ID NO | Name | Fwd Primer | Rev Primer |
|---|---|---|---|
| 1 | SULT1A1 *Rattus norvegicus* | CBJP472 | CBJP473 |
| 2 | SULT1A1 *Homo sapiens* | CBJP470 | CBJP471 |
| 3 | SULT1A1 *Equus caballus* | CBJP499 | CBJP500 |
| 4 | SULT1A1 *Sus scrofa domesticus* | CBJP505 | CBJP506 |
| 5 | SULT1A1 *Canis lupus familiaris* | CBJP503 | CBJP504 |
| 6 | SULT1E1 *Gallus gallus domesticus* | CBJP501 | CBJP502 |

The strains were grown in M9 minimal media containing glucose as a carbon source, and 0.1 mM IPTG for induction of gene expression as well as 0.1 mM p-coumaric acid (pHCA). After four days of growth, samples were withdrawn by filtration and analyzed by HPLC.

The concentration of p-courmaric acid (pHCA) and zosteric acid in the supernatant was quantified by high performance (HPLC) and compared to chemical standards. HPLC was done on a Thermo setup using a HS-F5 column and mobile phases: 5 mM ammonium formate pH 4.0 (A) and acetonitrile (B) at 1.5 mL min-1, using a gradient elution starting at 5% B. From 0.5 min after injection to 7 min, the fraction of B increased linearly from 5% to 60%, and between 9.5 min and 9.6 the fraction of B decreased back to 5%, and remaining there until 12 min. pHCA and zosteric acid were quantified by measuring absorbance at 277 nm.

Table 2 shows the remaining pHCA and the produced zosteric acid in the culture media. Zosteric acid was formed with an aryl sulfotransferase heterologously expressed in a microorganism exemplified by *E. coli* supplied with the substrate.

TABLE 2

Production of zosteric acid in *E. coli* from pHCA through the heterologous expression of sulfotransferases.

| Enzyme | pHCA remaining (mM) | Zosteric acid formed (mM) |
|---|---|---|
| No enzyme | 0.10 | Not detectable |
| SULT1A1 *Rattus norvegicus* | 0.02 | 0.10 |
| SULT1A1 *Homo sapiens* | 0.08 | 0.02 |
| SULT1A1 *Equus caballus* | 0.09 | 0.01 |
| SULT1A1 *Sus scrofa domesticus* | 0.09 | 0.01 |
| SULT1A1 *Canis lupus familiaris* | 0.10 | 0.01 |
| SULT1E1 *Gallus gallus domesticus* | 0.08 | 0.01 |

Example 2—Increased Production of Zosteric Acid in *E. coli*

The addition of sulfated groups to targets is dependent on supply of the donor molecule 3'-Phosphoadenosine 5'-phosphosulfate (PAPS). We examined if we could increase the production of zosteric acid by overexpressing enzymes providing PAPS and an enzyme that removes the product 3'-Phosphoadenosine 5'-phosphate (PAP).

TABLE 3

Cloning of enzymes involved in activating sulfate and product removal.

| Genes | Fwd Primer | Rev Primer |
|---|---|---|
| cysDNC alone | CBJP491 | CBJP492 |
| cysDNC for artificial operon | CBJP491 | CBJP497 |
| cysQ for artificial operon | CBJP498 | CBJP496 |

In *E. coli*, the genes cysD and cysN encode the two subunits of ATP sulfurylase (EC:2.7.7.4), cysC encodes APS kinase (EC:2.7.1.25), and cysQ encode a PAP phosphatase.

Figure 2:
FIG. 2: Map of plasmid for over-expression of cysDNC in *E. coli*.
Figure 3:
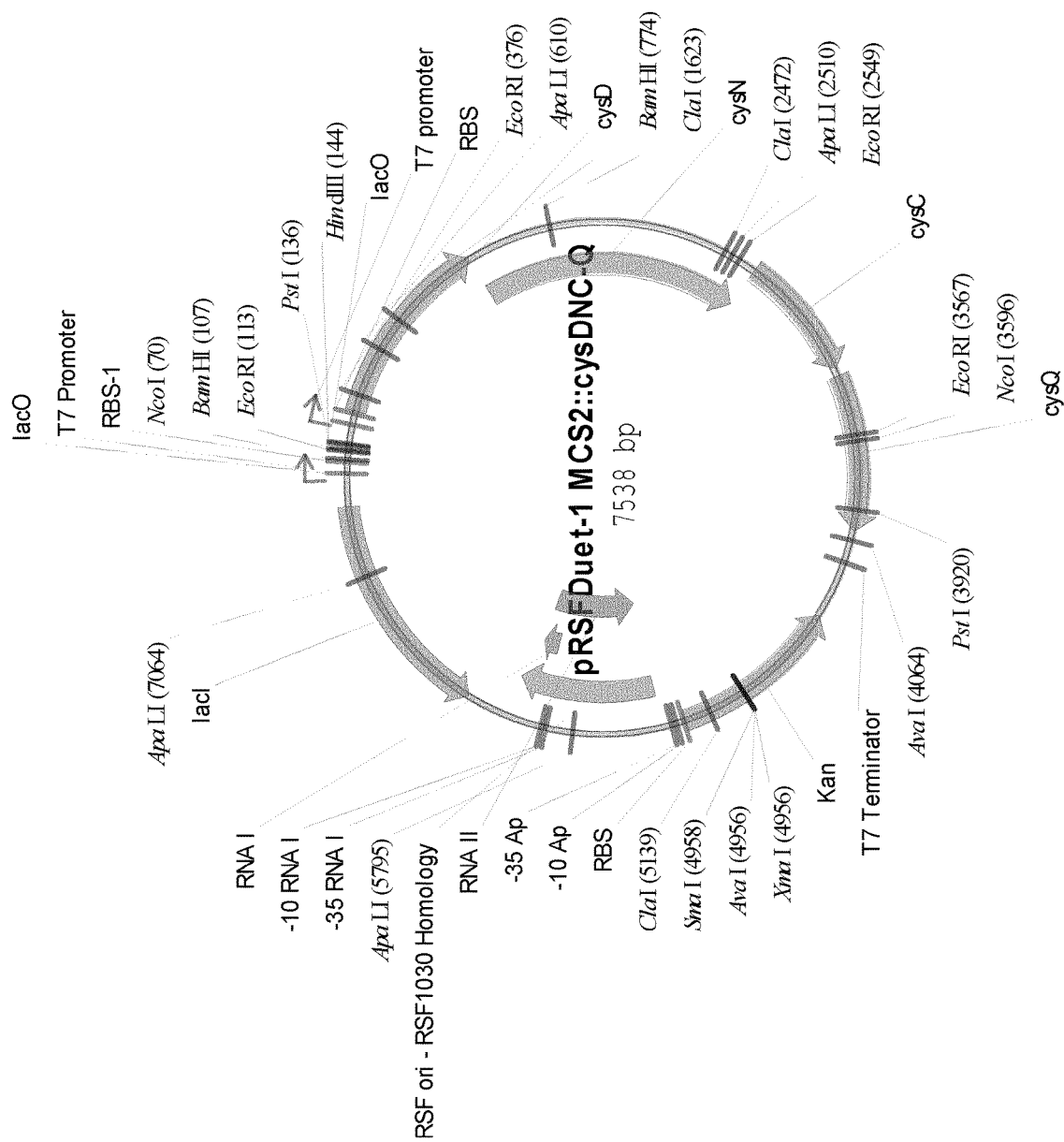
FIG. 3: Map of plasmid for over-expression of cysDNCQ in *E. coli*.
Figure 4:
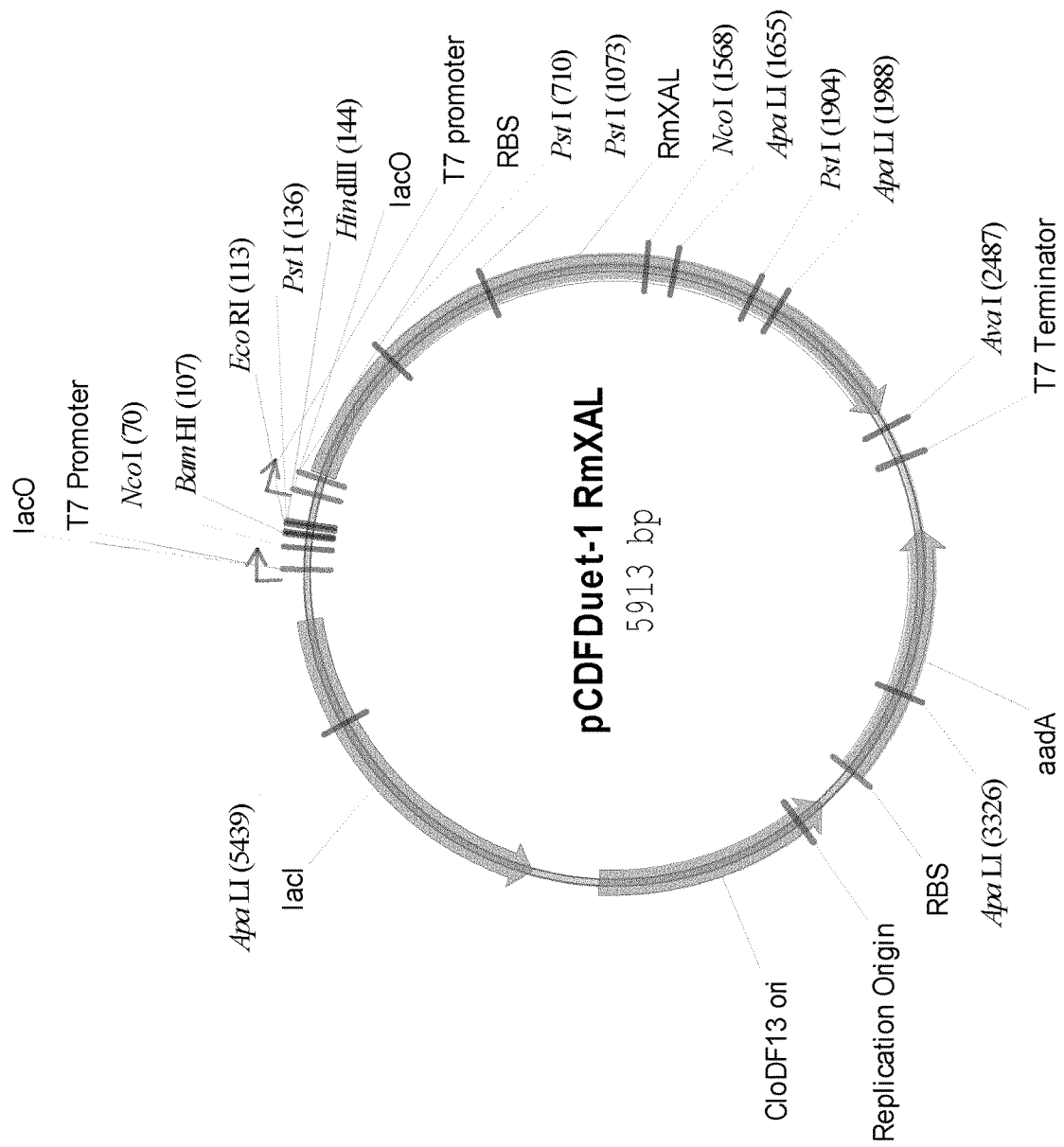
FIG. 4: Map of plasmid for expression of RmXAL from *Rhodotorula muciloginosa/Rhodotorula rubra* in *E. coli*.

The cysDNC cluster was amplified by PCR from *E. coli* MG1655 chromosomal DNA using the primers shown in table 3. The plasmid pRSFDuet-1 (Life Technologies) was digested by the restriction endonucleases NdeI and BglII. The gene cluster was inserted into the digested plasmid using the Gibson reaction (New England Biolabs). FIG. 2 shows the resulting plasmid. For the combined expression of cysDNC and cysQ in an artificial operon, cysDNCQ, the two parts were amplified by PCR from *E. coli* MG1655 chromosomal DNA using the primers shown in Table 3. Again the parts were inserted into the digested plasmid. FIG. 3 shows the resulting plasmids. The plasmid expressing SULT1A1 *Homo sapiens* (SEQ ID NO: 2) from example 1 was co-transformed into *E. coli* BL21(DE3)pLysS cells (Life Technologies) with either the plasmid expressing cysDNC or cysDNCQ.

Cells were grown as in Example 1 and the supernatants were analyzed for product formation as in example 1. The strain expressing SULT1A1 in combination with cysDNCQ was also grown without the addition of IPTIG for induction. Table 4 shows the concentrations of pHCA and zosteric acid.

TABLE 4

Concentrations of pHCA and zosteric acid in culture media with *E. coli* expressing an aryl sulfotransferase in combination with cysDNC and cysQ.

| Enzymes | Induction | pHCA remaining (mM) | Zosteric acid formed (mM) |
|---|---|---|---|
| SULT1A1 *Homo sapiens* | 0.1 mM IPTG | 0.08 | 0.02 |
| SULT1A1 *Homo sapiens*, CysDNC | 0.1 mM IPTG | 0.06 | 0.06 |
| SULT1A1 *Homo sapiens*, CysDNCQ | 0.1 mM IPTG | 0.04 | 0.09 |
| SULT1A1 *Homo sapiens*, CysDNCQ | None | 0.10 | Not detectable |

This shows that more of the pHCA is transformed into zosteric acid when the protein expression of cysDNC is increased. Even more zosteric acid is formed when the protein expression cysQ is additionally increased.

Example 3—Decreased Toxicity of Sulfated Product

Figure 5:
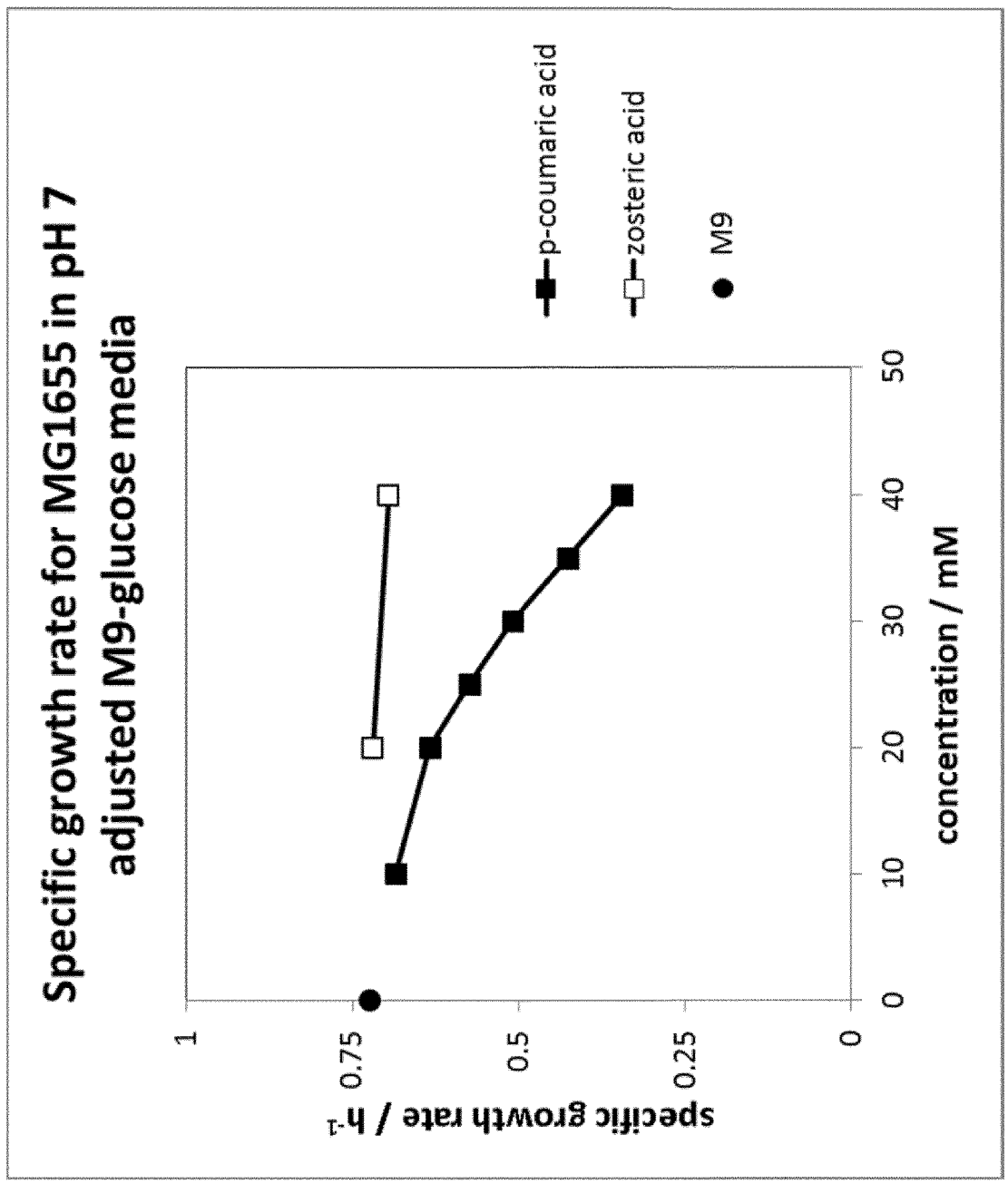
FIG. 5: Toxicity of unsulfated or sulfated products

*E. coli* MG1655 was grown in chemically defined M9 minimal media with 0.2% glucose as a carbon source without further addition or with the additions of either 10 mM, 20 mM, 25 mM, 30 mM, 35 mM or 40 mM p-coumaric acid (pHCA), or with 20 mM or 40 mM of the sulfate ester of pHCA (zosteric acid). All media preparations had been adjusted to pH 7. Cells were grown at 37° C. with 250 rpm shaking in an orbital shaker. The growth rates were examined by following the optical density at 600 nm. The resulting growth rates in exponential growth phase are shown in FIG. 5. Filled squares represent growth rates in media with pHCA. Open squares represent growth rates in media with zosteric acid. And the circle represents the growth rate in media without any of these additions. It is evident that the presence of pHCA is toxic to the cells, while the sulfate ester, zosteric acid is much less so.

Figure 6:
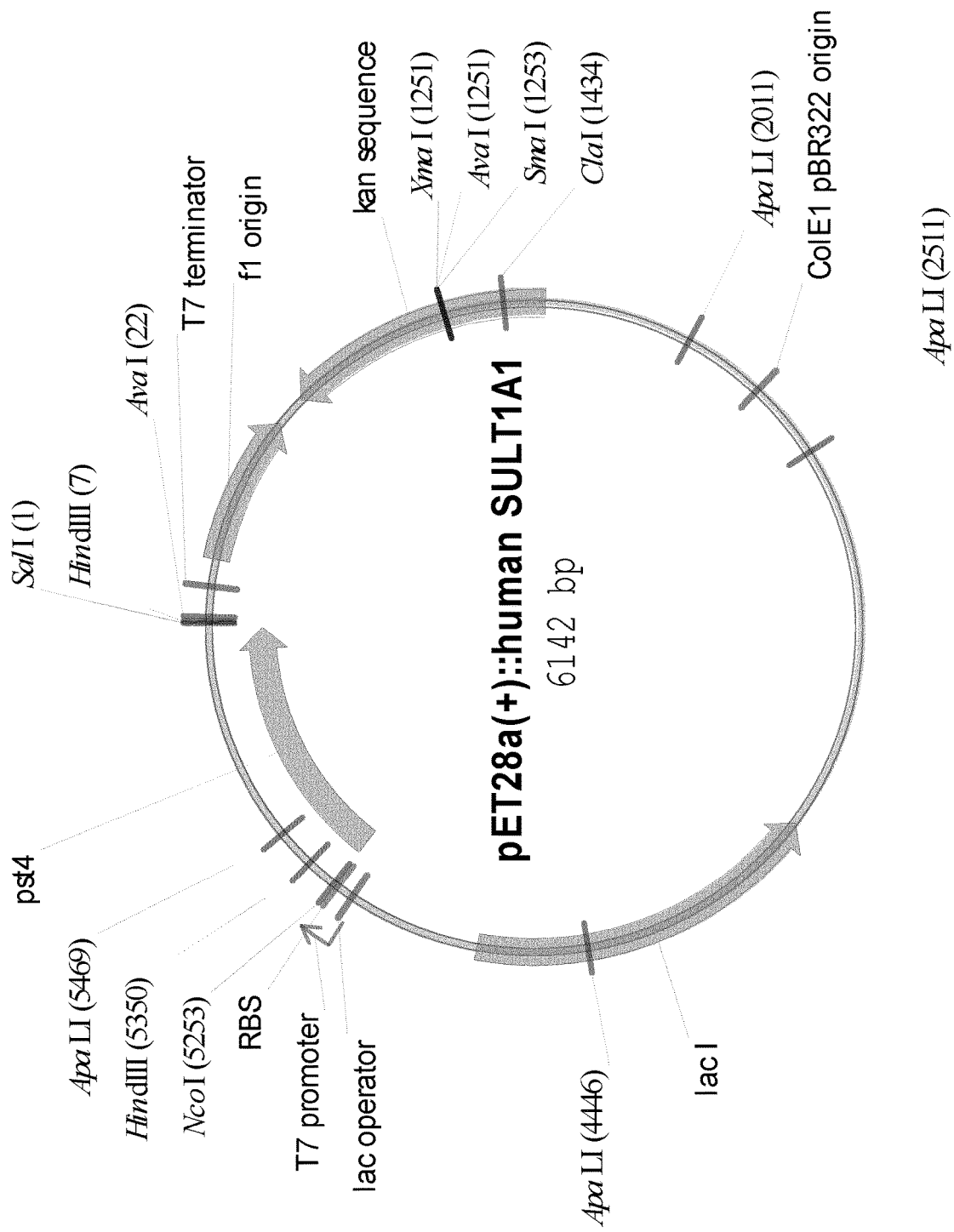
FIG. 6: Map of plasmid for expression of SULT1A1 from *Homo sapiens* in *E. coli*

Example 4—Decreased Growth Inhibition with the Expression of an Aryl Sulfotransferase SULT1A1 from *Homo sapiens* (SEQ ID NO: 2) mentioned in example 1 was cloned into the plasmid vector pET-28a(+) (Novagen, Life Technologies) as follows: The gene encoding the SULT1A1 was codon optimized for expression in *E. coli* by GeneArt (LifeTechnologies) and synthesized such that the start codon is an NcoI restriction site. The stop codon is immediately followed by a SalI site. The NcoI and SalI fragment of this DNA piece was cloned into the pET-28a(+) digested with NcoI and SalI using T4 DNA ligase. The resulting plasmid was transformed into *E. coli* BL21(DE3)pLysS (Life Technologies) selecting for resistance to 50 mg mL$^{-1}$ kanamycin. A map of the resulting plasmid is shown in FIG. 6.

The two strains BL21(DE3)pLysS and the strain carrying SULT1A1 were grown in M9 minimal media with 0.2% glucose, appropriate antibiotics for maintenance of the plasmids, and 0.1 mM IPTG for induction of expression of the sulfotransferase. We added ferulic acid to final concentration of either 2.5 mM or 5 mM (ferulic acid was dissolved in ethanol, which reached a final concentration of 2% in the media). Ferulic acid is a growth inhibitory compound found in lignocellulotic biomass hydrolysate. Cells were inoculated into the medium to an optical density at 600 nm (OD$_{600}$) of 0.002 in a 1 cm light path. Table 5 below shows the cell density reached after 17 h of growth at 37° C. with orbital shaking at 250 rpm for the two strains with or without SULT1A1. Presence of an aryl sulfotransferase removes the inhibition caused by ferulic acid.

TABLE 5

Cell densities of *E. coli* reached in media with the growth inhibitor ferulic acid with or without the expression of a sulfotransferase.

| | Optical density at 600 nm | |
|---|---|---|
| Concentration of inhibitor | Without SULT1A1 | With SULT1A1 |
| 2.5 mM ferulic acid | 0.680 | 1.410 |
| 5 mM ferulic acid | 0.370 | 1.340 |

Example 5—Production of Sulfated Products in Other Hosts

We have shown that zosteric acid can be produced in vivo in *Escherichia coli* by expression of an aryl sulfotransferase. To show that the reaction is possible in other microorganisms, we here show that the yeast *Saccharomyces cerevisiae* can also be used as a host for the production.

Figure 7:
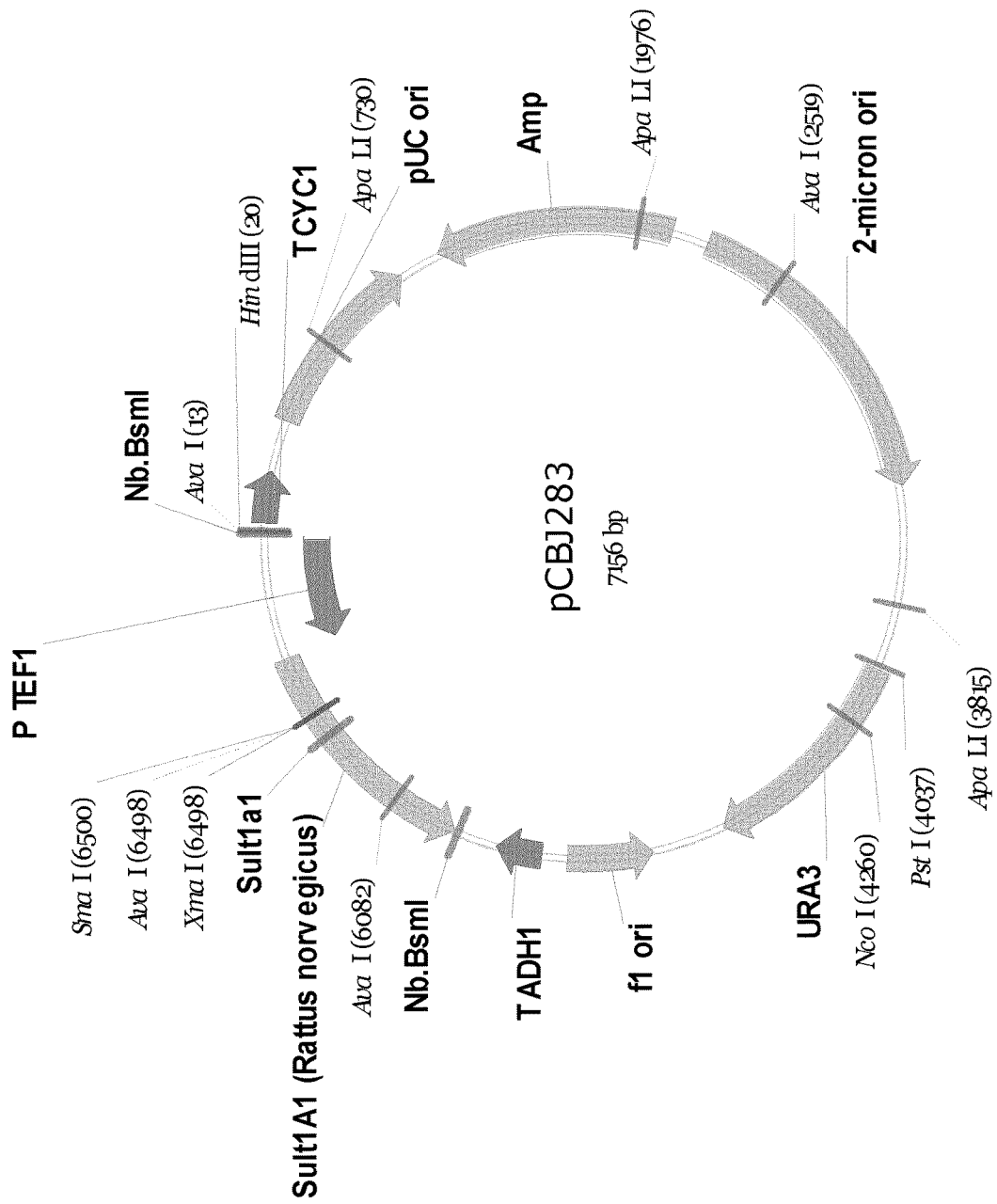
FIG. 7: Map of plasmid for expression of SULT1A1 from *Rattus norvegicus* in *Saccharomyces cerevisiae* (native gene).
Figure 8:
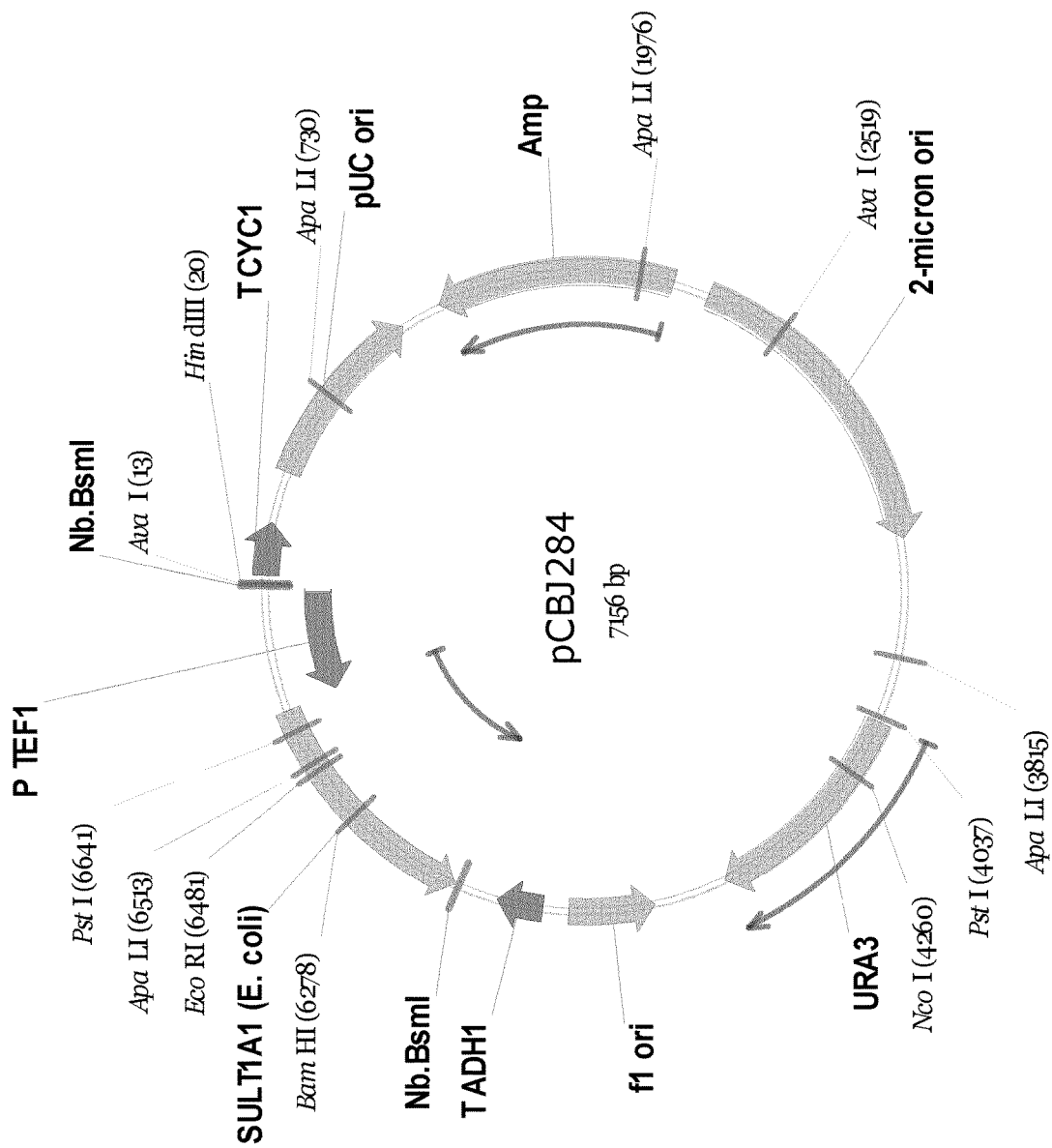
FIG. 8: Map of plasmid for expression of SULT1A1 from *Rattus norvegicus* in *Saccharomyces cerevisiae* (codon-optimized gene).

The gene encoding aryl sulfotransferase SULT1A (Example 1) was cloned after a TEF1 promoter into an episomal plasmid with a 2-micron origin of replication as follows. The gene was amplified by PCR using primers CBJP633 and CBJP634. Alternatively, the gene was codon-optimized for *E. coli* and synthesized by GeneArt and amplified by primers CBJP635 and CBJP636. The TEF1 promoter (Jensen et al., 2014, *FEMS Yeast Res* 14: 238-248) was amplified by PCR using the primers PTEF1_fw and PTEF1_rv. Plasmid pCfB132 (Jensen et al., supra) was digested by restriction enzymes AsiSI and Nt.BsmI. The three fragments—plasmid, TEF1 promotor and SULT1A1-encoding gene—were assembled using a uracil-excission cloning procedure, resulting in plasmids pCBJ283 and pCBJ284 (FIGS. 7 and 8, respectively, which was subsequently transformed into the *Saccharomyces cerevisiae* strain CEN.PK102-5B selecting for growth on synthetic dropout media plates lacking uracil. A control strain was also made by transformation of pCfB132 into CEN.PK102-5B.

Primers:

| Oligo-nucleotide | Gene/promoter | Direction | Sequence |
|---|---|---|---|
| CBJP633 | SULT1A1 rat | Forward | AGTGCAGGUAAAACAATGgagttctcccgtcca (SEQ ID NO: 36) |
| CBJP634 | SULT1A1 rat | Reverse | CGTGCGAUTCAtagttcacaacgaaacttg (SEQ ID NO: 37) |
| CBJP635 | SULT1A1 rat (*E. coli*) | Forward | ATCTGTCAUAAAACAATGgaattttcacgtccgc (SEQ ID NO: 38) |
| CBJP636 | SULT1A1 rat (*E. coli*) | Reverse | CACGCGAUTCAcagttcacaacgaaatttgaa (SEQ ID NO: 39) |
| PTEF1_fw | PTEF1 | Forward | Cacgcgaugcacacaccatagcttc (SEQ ID NO: 40) |
| PTEF1_rv | PTEF1 | Reverse | Cgtgcgauggaagtaccttcaaaga (SEQ ID NO: 41) |

The strains were grown in modified Delft medium (Jensen et al., supra) with 20 mg/mL histidine and 60 mg/mL leucine and 10 mM p-coumaric acid overnight at 30° C. with aeration. The supernatant was then isolated and examined by HPLC as described in Example 1. The table below shows that zosteric acid (ZA) was produced by the strain expressing SULT1A1 and not the control strain lacking a sulfotransferase.

| Sulfotransferase | µM ZA (averages and standard deviations of replicate experiments) |
|---|---|
| None | 0 ± 0 |
| SULT1A1 rat (native) | 37.8 ± 5.7 |
| SULT1A1 rat (codon optimized for E. coli) | 46.2 ± 3.5 |

It is evident that zosteric acid is formed only when a sulfotransferase is expressed in yeast, and that the gene encoding this may be natural or encoded by a synthetic gene with a specific codon-optimization. Conclusively, the sulfation reactions shown to be catalyzed by sulfotransferases in E. coli are also catalyzed when the sulfotransferases are expressed in other organisms, as demonstrated here for the yeast S. cerevisiae. The efficacy of production may be affected by means such as the codon-usage of the genes encoding the sulfotransferase. Thus yeast expressing sulfotransferases may be able to detoxify aromatic compounds such as p-coumaric acid, and form sulfated products such as zosteric acid.

Example 6—A Range of Compounds are Substrates for Sulfation In Vivo

Here we show that the expression of an aryl sulfotransferase may be able to convert several substrates. Some of these are inhibitors that can be found in biomass hydrolyzate used as a substrate for cell growth and production in biotechnology. The compounds also include some that are of biotechnological interest as products of a cell culture or be some whose sulfate ester is of economic interest.

Different sulfotransferases were examined for their substrate specificities against three substrates. We tested the sulfotransferases mentioned in example 1, as well as additional ones. The genes encoding these were cloned as described in example 1 using the primers shown in the table below from cDNA libraries of the respective organisms, except for the SULT1A1 from rat (Rattus norvegicus) codon-optimized for E. coli (described above). The resulting vectors were transformed into BL21(DE3)pLysS.

Primers:

The resulting strains were grown in M9 medium containing either 100 µM pHCA, 95 µM resveratrol or 87 µM kaempferol. The cultures were grown overnight at 37° C., 300 rpm. The following day the supernatants were isolated and examined by HPLC as described in example 1. BL21 (DE3)pLysS were used as a control strain and did not convert the substrates.

| Enzyme | pHCA 100 µM | resveratrol 95 µM | kaempferol 87 µM |
|---|---|---|---|
| SULT1A1 Rattus norvegicus | 93% | 93% | 95% |
| SULT1C1 Gallus gallus domesticus | 26% | 100% | 80% |
| SULT1A1 Rattus norvegicus (Codon-optimized for E. coli) | 73% | 58% | 38% |
| SULT1A1 human | 39% | 36% | 97% |
| SULT1A1 Equus caballus | 21% | 100% | 96% |
| SULT1E1 Gallus gallus domesticus | 17% | 100% | 47% |
| SULT1A1 Canis lupus familiaris | 34% | 61% | 60% |
| SULT1A1 Sus scrofa domesticus | 8% | 88% | 45% |

The table shows the percent conversion of the various substrates by cells expressing the different sulfotransferases. The results show that several sulfotransferases, and especially the aryl sulfotransferase from rat (Rattus norvegicus), may be employed in the sulfation of phenolic compounds.

To further test the range of substrates that can be sulfated, we used strains carrying plasmids expressing SULT1A1 from rat (Rattus norvegicus) and SULT1E1 from chicken (Gallus gallus domesticus) (Example 1) cloned into the expression vector pETDuet-1, and cysDNCQ from E. coli cloned into expression vector pRSFDuet-1 (Example 2). The plasmids were introduced into the E. coli expression strain BL21(DE3)pLysS as described previously, selecting for transformants with appropriate antibiotics, namely 34 µg mL$^{-1}$ chloramphenicol for pLysS, 100 µg mL$^{-1}$ ampicillin for pETDuet-1-based vectors, and 100 µg mL$^{-1}$ kanamycin for pRSFDuet-1-based vectors. The table below shows the combination of over-expressed genes on plasmids. A control strain without a sulfotransferase gene or cysDNCQ operon was also examined.

| E. coli strains | Sulfotransferase | Cys genes |
|---|---|---|
| Control strain | — | — |
| SULT1A1 rat | SULT1A1 rat | — |

| Oligo-nucleotide | Gene | Direction | Sequence |
|---|---|---|---|
| CBJP517 | SULT1C1 Gallus gallus domesticus | Forward | TAGAAATAATTTTGTTTAACTTTA AGAAGGAGATATACCatggccctgg ataaaatgg (SEQ ID NO: 42) |
| CBJP518 | SULT1C1 Gallus gallus domesticus | Reverse | TAAGCATTATGCGGCCGCAAGCT TGtcacaattccatgcgaaaaactag (SEQ ID NO: 43) |
| CBJP533 | SULT1A1 Rattus norvegicus (Codon-optimized for E. coli) | Forward | TAGAAATAATTTTGTTTAACTTTA AGAAGGAGATATACCatggaattttc acgtcc (SEQ ID NO: 44) |
| CBJP534 | SULT1A1 Rattus norvegicus (Codon-optimized for E. coli) | Reverse | TAAGCATTATGCGGCCGCAAGCT TGttacagttcacaacgaaatttg (SEQ ID NO: 45) |

-continued

| E. coli strains | Sulfotransferase | Cys genes |
|---|---|---|
| SULT1E1 chicken | SULT1E1 chicken | — |
| SULT1A1 rat + CysDNCQ | SULT1A1 rat | CysDNCQ |

The strains were precultured in 2×YT medium with appropriate antibiotics. 10 μL of these precultures were used to inoculate M9 media with 1 mM IPTG and none or a single substrate for sulfation. After overnight growth at 37° C., 300 rpm the supernatants were withdrawn and examined by HPLC as described in Example 1. The compounds were detected by UV absorbance. The table below shows the percent reduction in concentration in the strains expressing sulfotransferases alone or in combination with cysDNCQ genes when compared to the control strain.

| Compound | Start concentration in μM | SULT1A1 | SULT1E1 | SULT1A1 + CysDNCQ |
|---|---|---|---|---|
| Ferulic acid | 110 | 72% | 67% | 100% |
| Quercetin | 85 | 75% | 74% | 81% |
| 4-hydroxybenzoic acid | 287 | 5% | 4% | 6% |
| 4-acetamidophenol | 114 | 24% | 10% | 30% |
| 3-Hydroxy-4-methoxycinnamic acid | 132 | 51% | 24% | 62% |
| 4-Hydroxyphenylpyruvic acid | 255 | 47% | 100% | 64% |
| 3-(4-Hydroxyphenyl)propionic acid | 241 | 3% | 1% | 7% |
| Vanillic acid | 173 | 33% | 0% | 39% |
| Luteolin | 61 | 27% | 0% | 37% |
| Apigenin | 77 | 41% | 98% | 99% |
| fisetin | 81 | 98% | 98% | 100% |

Conclusively, a wide range of phenolic compounds are substrates for sulfotransferases. In the shown examples, the conversion is enhanced by the overexpression of cysDNCQ genes. Some of these compounds and their sulfate esters are of interest in biotechnology. Also, some of these compounds are inhibitors of cell growth and function, and thus conversion by sulfation is of interest for use in biological systems.

Example 7—Use of Sulfotransferases in Complex Biomass

A preferred source of carbon for cell growth and as substrates for manufacture of chemicals and other products in biotechnology is a complex carbon source, such as biomass hydrolysate. These complex carbon sources often contains phenolic compounds that are toxic to prokaryotic as well as eukaryotic organisms (Adeboye et al., 2014, *AMB Express* 4: 46-014-0046-7. eCollection 2014)

Here, we examine pre-treated wheat straw biomass hydrolysate in growth medium for a biotechnological relevant organism, exemplified by *E. coli*. Specifically, we used strains carrying plasmids expressing SULT1A1 from rat (*Rattus norvegicus*) and SULT1E1 from chicken (*Gallus gallus domesticus*) (Example 1) cloned into the expression vector pETDuet-1, and cysDNCQ from *E. coli* cloned into expression vector pRSFDuet-1 (Example 2) as described previously.

Figure 9:
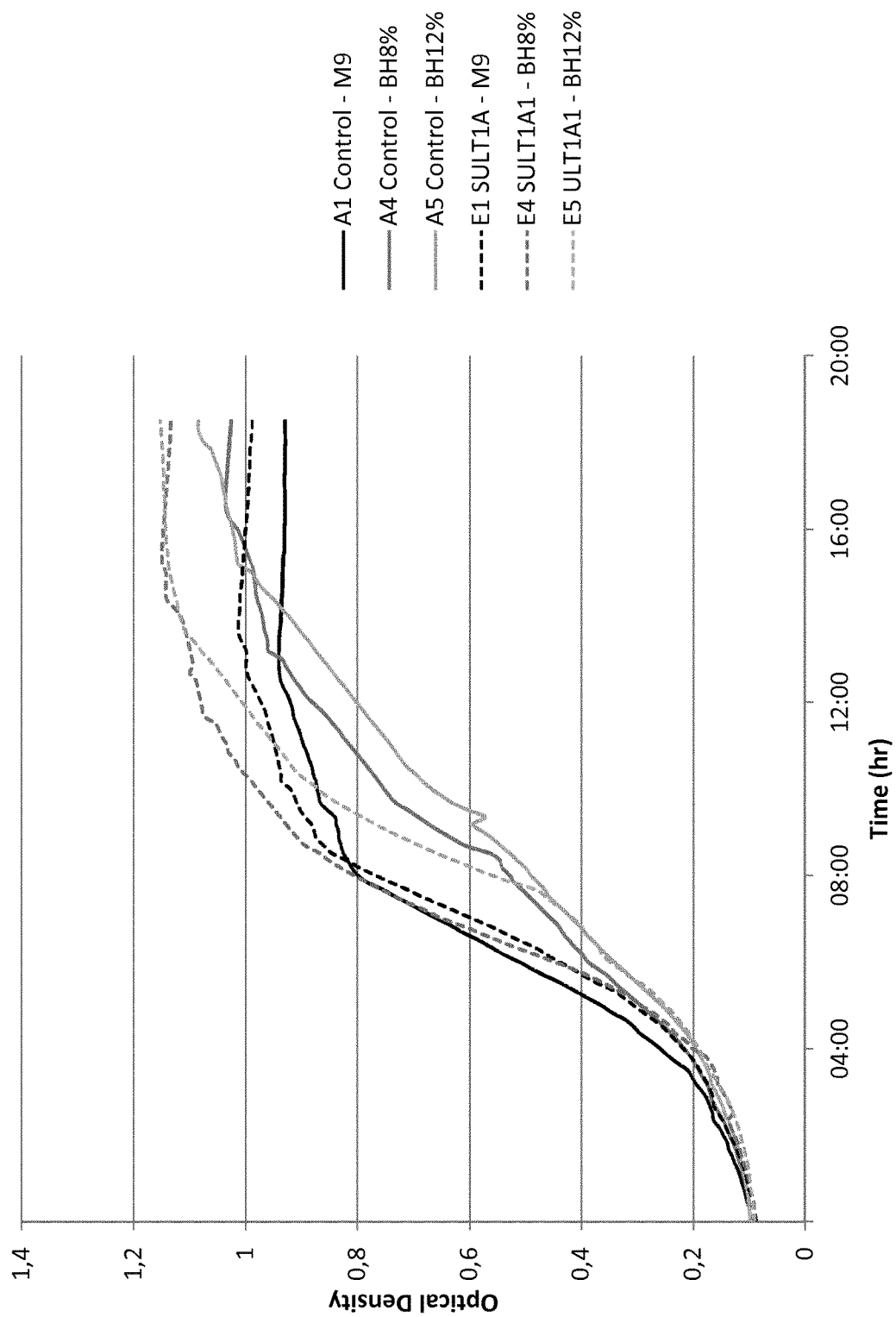
FIG. 9: Growth curves of cultures without sulfotransferase (solid lines) or with SULT1A1 (dotted lines) growing in M9 without supplements (black), with 8% biomass hydrolysate (BH8%, dark grey), or with 12% biomass hydrolysate (BH12%, light grey).

Cells expressing no sulfotransferase or SULT1A1 from rat were grown in M9 media with 1 mM IPTG with or without inhibitors of growth. Biomass hydrolysate was prepared by mixing 100 g biomass hydrolysate with 200 g of water for 2 h at 37° C., followed by centrifugation and filtration through a 0.2 μL-filter. FIG. 9 shows the growth curves of cultures without sulfotransferase (solid lines) or with SULT1A1 (dotted lines) growing in M9 without supplements (black), with 8% biomass hydrolysate (BH8%, dark grey), or with 12% biomass hydrolysate (BH12%, light grey).

There is no difference in growth rate between cultures in M9, but with biomass hydrolysate the growth rate of the strain expressing a gene encoding SULT1A1 is significantly higher. Conclusively, cells expressing sulfotransferase have a growth advantage in media containing phenolic compounds that inhibit the growth cells, such as biomass hydrolysate being used as a carbon source for biotechnological production of chemicals.

The invention claimed is:

1. A process for producing a hydrolyzed product from a lignocellulose-containing material, comprising:
   (a) pre-treating a lignocellulose-containing material;
   (b) hydrolyzing the pre-treated lignocellulose-containing material to form a hydrolyzate; and
   (c) contacting phenolic compounds produced during step a) or step b) with a recombinant host cell comprising a heterologous aryl sulfotransferase, wherein the recombinant host cell has been further modified to have an increased protein expression of (i) an APS kinase or (ii) a PAP phosphatase compared to an identical host cell that does not carry said modifications.

2. The process according to claim 1, wherein step (c) is performed using an isolated recombinant host cell comprising a heterologous aryl sulfotransferase.

3. The process according to claim 2, wherein the heterologous aryl sulfotransferase is selected from the group consisting of:
   i) a polypeptide comprising an amino acid sequence set forth in SEQ ID NO: 1, 6, 7, 8 or 10; and
   ii) a polypeptide comprising an amino acid sequence which has at least 95% sequence identity to the amino acid sequence set forth in SEQ ID NO: 1, 6, 7, 8 or 10, wherein the polypeptide has an aryl sulfotransferase activity.

4. The process according to claim 2, wherein the heterologous aryl sulfotransferase is selected from the group consisting of:
   i) a polypeptide comprising the amino acid sequence set forth in SEQ ID NO: 1; and
   ii) a polypeptide comprising an amino acid sequence which has at least 95% sequence identity to the amino acid sequence set forth in SEQ ID NO: 1, wherein the polypeptide has aryl sulfotransferase activity.

5. The process according to claim 1, wherein the recombinant host cell has been further modified to have an increased protein expression of an ATP sulfurylase compared to an identical host cell that does not carry said modification.

6. The process according to claim 5, wherein the recombinant host cell is *Escherichia coli* and the ATP sulfurylase is encoded by the genes cysD and cysN.

7. The process according to claim 2, wherein said recombinant host cell has been further modified to have an increased protein expression of an APS kinase compared to an identical host cell that does not carry said modification.

8. The process according to claim 7, wherein the recombinant host cell is *Escherichia coli* and said APS kinase is encoded by the gene cysC.

9. The process according to claim 2, wherein said recombinant host cell has been further modified to have an increased protein expression of a PAP phosphatase compared to an identical host cell that does not carry said modification.

10. The process according to claim 9, wherein the recombinant host cell is *Escherichia coli* and said PAP phosphatase is encoded by the gene cysQ.

11. The process according to claim 2, wherein the recombinant host cell is selected from the group consisting of bacteria, yeasts, fungi, and algae.

12. The process according to claim 2, wherein the recombinant host cell is a bacterium.

13. The process according to claim 2, wherein the recombinant host cell is a yeast.

14. The process according to claim 1, wherein in step (b) the pre-treated lignocellulose containing material is enzymatically hydrolyzed.

15. The process according to claim 1, wherein in step a) said lignocellulose-containing material is pre-treated chemically, mechanically or biologically.

* * * * *